US009011509B2

(12) United States Patent
Stafford et al.

(10) Patent No.: US 9,011,509 B2
(45) Date of Patent: *Apr. 21, 2015

(54) INDIVIDUALLY OPTIMIZED PERFORMANCE OF OPTICALLY STIMULATING COCHLEAR IMPLANTS

(75) Inventors: Ryan C. Stafford, Monroe, WA (US); Jonathon D. Wells, Seattle, WA (US); James W. Stafford, Redmond, WA (US); Bryan J. Norton, Seattle, WA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/555,093

(22) Filed: Jul. 21, 2012

(65) Prior Publication Data
US 2013/0023961 A1 Jan. 24, 2013

Related U.S. Application Data

(60) Provisional application No. 61/511,020, filed on Jul. 22, 2011, provisional application No. 61/511,048, filed on Jul. 23, 2011, provisional application No. 61/511,050, filed on Jul. 23, 2011.

(51) Int. Cl.
*A61N 5/067* (2006.01)
*A61N 5/06* (2006.01)
(Continued)

(52) U.S. Cl.
CPC .............. *A61N 5/0622* (2013.01); *A61N 1/0541* (2013.01); *A61N 1/36032* (2013.01);
(Continued)

(58) Field of Classification Search
None
See application file for complete search history.

(56) References Cited

U.S. PATENT DOCUMENTS 4,215,694 A 8/1980 Isakov et al.
4,400,590 A 8/1983 Michelson
(Continued)

FOREIGN PATENT DOCUMENTS

WO WO 0025112 5/2000
WO WO-2010006049 1/2010
(Continued)

OTHER PUBLICATIONS

Richter et al., Optical Stimulation of auditory neurons: Effects of acute and chronic deafening, Hear Res. 242, Aug. 2008.*
(Continued)

*Primary Examiner* — Lynsey Crandall
*Assistant Examiner* — Manolis Pahakis
(74) *Attorney, Agent, or Firm* — Charles A. Lemaire; Jonathan M. Rixen; Lemaire Patent Law Firm, P.L.L.C.

(57) ABSTRACT

Method and apparatus for optically stimulating neurons of a plurality of auditory nerve pathways of a person to provide auditory sensations for the person including generating a plurality of pulsed light signals having one or more successive pulses; delivering the plurality of pulsed light signals to one or more auditory nerve pathways of the cochlea of the person; selectively controlling the plurality of light signals to optically stimulate and trigger nerve action potentials (NAPs) in the one or more auditory nerve pathways, wherein the selectively controlling includes empirically testing the delivering of the plurality of light signals and determining which optical-stimulation parameters used during the testing are most effective for optically stimulating the auditory nerve pathways of the person, and using results of the testing such that the delivering includes delivering the plurality of light signals with the optical-stimulation parameters that were determined to be most effective for optically stimulating.

20 Claims, 17 Drawing Sheets

(51) Int. Cl.
*A61N 1/05* (2006.01)
*A61N 1/36* (2006.01)

(52) U.S. Cl.
CPC . *A61N2005/0605* (2013.01); *A61N 2005/0652* (2013.01); *A61N 2005/0659* (2013.01); *A61N 2005/067* (2013.01); *A61N 2005/0626* (2013.01)

(56) References Cited

U.S. PATENT DOCUMENTS

| | | | |
|---|---|---|---|
| 4,558,703 A | 12/1985 | Mark | |
| 4,566,935 A | 1/1986 | Hornbeck | |
| 4,596,992 A | 6/1986 | Hornbeck | |
| 4,671,285 A | 6/1987 | Walker | |
| 4,724,835 A | 2/1988 | Liss et al. | |
| 4,757,515 A | 7/1988 | Hughes | |
| 4,768,516 A | 9/1988 | Stoddart et al. | |
| 4,813,418 A | 3/1989 | Harris | |
| 4,928,695 A | 5/1990 | Goldman et al. | |
| 4,930,504 A | 6/1990 | Diamantopoulos et al. | |
| 4,972,331 A | 11/1990 | Chance | |
| 4,989,605 A | 2/1991 | Rossen | |
| 5,062,428 A | 11/1991 | Chance | |
| 5,088,493 A | 2/1992 | Giannini et al. | |
| 5,122,974 A | 6/1992 | Chance | |
| 5,139,025 A | 8/1992 | Lewis et al. | |
| 5,150,704 A | 9/1992 | Tatebayashi et al. | |
| 5,151,909 A | 9/1992 | Davenport et al. | |
| 5,152,278 A | 10/1992 | Clayman | |
| 5,187,672 A | 2/1993 | Chance et al. | |
| 5,192,278 A | 3/1993 | Hayes et al. | |
| 5,212,386 A | 5/1993 | Gratton et al. | |
| 5,213,093 A | 5/1993 | Swindle | |
| 5,213,105 A | 5/1993 | Gratton et al. | |
| 5,257,202 A | 10/1993 | Feddersen et al. | |
| 5,259,382 A | 11/1993 | Kronberg | |
| 5,323,010 A | 6/1994 | Gratton et al. | |
| 5,327,902 A | 7/1994 | Lemmen | |
| 5,353,799 A | 10/1994 | Chance | |
| 5,386,827 A | 2/1995 | Chance et al. | |
| 5,391,081 A * | 2/1995 | Lampotang et al. | 434/262 |
| 5,402,778 A | 4/1995 | Chance | |
| 5,419,312 A | 5/1995 | Arenberg et al. | |
| 5,445,146 A | 8/1995 | Bellinger | |
| 5,548,604 A | 8/1996 | Toepel | |
| 5,553,614 A | 9/1996 | Chance | |
| 5,564,417 A | 10/1996 | Chance | |
| 5,608,519 A | 3/1997 | Gourley et al. | |
| 5,664,574 A | 9/1997 | Chance | |
| 5,754,578 A | 5/1998 | Jayaraman | |
| 5,755,752 A | 5/1998 | Segal | |
| 5,791,231 A | 8/1998 | Cohn et al. | |
| 5,792,051 A | 8/1998 | Chance | |
| 5,796,889 A | 8/1998 | Xu et al. | |
| 5,799,030 A | 8/1998 | Brenner | |
| 5,827,265 A | 10/1998 | Glinsky et al. | |
| 5,851,223 A | 12/1998 | Liss et al. | |
| 5,913,884 A | 6/1999 | Trauner et al. | |
| 5,957,960 A | 9/1999 | Chen et al. | |
| 6,033,431 A | 3/2000 | Segal | |
| 6,048,359 A | 4/2000 | Biel | |
| 6,066,127 A | 5/2000 | Abe | |
| 6,074,411 A | 6/2000 | Lai et al. | |
| 6,104,957 A | 8/2000 | Alo et al. | |
| 6,110,195 A | 8/2000 | Xie et al. | |
| 6,152,882 A | 11/2000 | Prutchi | |
| 6,171,239 B1 | 1/2001 | Humphrey | |
| 6,240,308 B1 | 5/2001 | Hardy et al. | |
| 6,246,892 B1 | 6/2001 | Chance | |
| 6,263,221 B1 | 7/2001 | Chance et al. | |
| 6,267,779 B1 | 7/2001 | Gerdes | |
| 6,272,367 B1 | 8/2001 | Chance | |
| 6,301,279 B1 | 10/2001 | Garbuzov et al. | |
| 6,312,451 B1 | 11/2001 | Streeter | |
| 6,314,324 B1 | 11/2001 | Lattner et al. | |
| 6,324,429 B1 | 11/2001 | Shire et al. | |
| 6,330,388 B1 | 12/2001 | Bendett et al. | |
| 6,339,606 B1 | 1/2002 | Alphonse | |
| 6,358,272 B1 | 3/2002 | Wilden | |
| 6,363,188 B1 | 3/2002 | Alphonse | |
| 6,417,524 B1 | 7/2002 | Alphonse | |
| 6,421,474 B2 | 7/2002 | Jewell et al. | |
| 6,456,866 B1 | 9/2002 | Tyler et al. | |
| 6,488,704 B1 | 12/2002 | Connelly et al. | |
| 6,493,476 B2 | 12/2002 | Bendett | |
| 6,505,075 B1 | 1/2003 | Weiner | |
| 6,542,530 B1 | 4/2003 | Shieh et al. | |
| 6,542,772 B1 | 4/2003 | Chance | |
| 6,546,291 B2 | 4/2003 | Merfeld et al. | |
| 6,556,611 B1 | 4/2003 | Khalfin et al. | |
| 6,564,076 B1 | 5/2003 | Chance | |
| 6,585,722 B1 | 7/2003 | Abe | |
| 6,592,611 B1 | 7/2003 | Zawada | |
| 6,636,678 B1 | 10/2003 | Bendett et al. | |
| 6,639,930 B2 | 10/2003 | Griffel et al. | |
| 6,669,379 B2 | 12/2003 | Janosik et al. | |
| 6,688,783 B2 | 2/2004 | Janosik et al. | |
| 6,690,873 B2 | 2/2004 | Bendett et al. | |
| 6,735,474 B1 | 5/2004 | Loeb et al. | |
| 6,735,475 B1 | 5/2004 | Whitehurst et al. | |
| 6,736,807 B2 | 5/2004 | Yamazaki et al. | |
| 6,744,548 B2 | 6/2004 | Abeles | |
| 6,746,473 B2 | 6/2004 | Shanks et al. | |
| 6,748,275 B2 | 6/2004 | Lattner et al. | |
| 6,823,109 B2 | 11/2004 | Sasaki et al. | |
| RE38,670 E | 12/2004 | Asah et al. | |
| 6,836,685 B1 | 12/2004 | Fitz | |
| 6,871,084 B1 | 3/2005 | Kingsley et al. | |
| 6,902,528 B1 | 6/2005 | Garibaldi et al. | |
| 6,909,826 B2 | 6/2005 | Cai et al. | |
| 6,921,413 B2 | 7/2005 | Mahadevan-Jansen et al. | |
| 6,953,341 B2 | 10/2005 | Black | |
| 6,956,650 B2 | 10/2005 | Boas et al. | |
| 6,980,579 B2 | 12/2005 | Jewell | |
| 6,989,023 B2 | 1/2006 | Black | |
| 7,003,353 B1 | 2/2006 | Parkhouse | |
| 7,004,645 B2 | 2/2006 | Lemoff et al. | |
| 7,006,749 B2 | 2/2006 | Illich et al. | |
| 7,010,341 B2 | 3/2006 | Chance | |
| 7,010,356 B2 | 3/2006 | Jog et al. | |
| 7,031,363 B2 | 4/2006 | Biard et al. | |
| 7,068,878 B2 | 6/2006 | Crossman-Bosworth et al. | |
| 7,069,083 B2 | 6/2006 | Finch | |
| 7,079,900 B2 | 7/2006 | Greenburg et al. | |
| 7,095,770 B2 | 8/2006 | Johnson | |
| 7,116,886 B2 | 10/2006 | Colgan et al. | |
| 7,131,968 B2 | 11/2006 | Bendett et al. | |
| 7,139,603 B2 | 11/2006 | Chance | |
| 7,156,866 B1 | 1/2007 | Riggs et al. | |
| 7,160,289 B2 | 1/2007 | Cohen | |
| 7,177,081 B2 | 2/2007 | Tomita et al. | |
| 7,190,993 B2 | 3/2007 | Sharma et al. | |
| 7,194,063 B2 | 3/2007 | Dilmanian et al. | |
| 7,225,028 B2 | 5/2007 | Della Santina et al. | |
| 7,231,256 B2 | 6/2007 | Wahlstrand et al. | |
| 7,244,253 B2 | 7/2007 | Neev | |
| 7,302,296 B1 | 11/2007 | Hoffer | |
| 7,309,335 B2 | 12/2007 | Altshuler et al. | |
| 7,311,722 B2 | 12/2007 | Larsen | |
| 7,324,852 B2 | 1/2008 | Barolat et al. | |
| 7,329,251 B2 | 2/2008 | Yamada et al. | |
| 7,337,004 B2 | 2/2008 | Classen et al. | |
| 7,351,241 B2 | 4/2008 | Bendett et al. | |
| 7,391,561 B2 | 6/2008 | Di Teodoro et al. | |
| 7,402,167 B2 | 7/2008 | Nemenov | |
| RE40,587 E | 11/2008 | McKinnon | |
| 7,488,341 B2 | 2/2009 | Merfeld | |
| 7,598,088 B2 | 10/2009 | Balas | |
| 7,647,112 B2 | 1/2010 | Tracey et al. | |
| 7,654,750 B2 | 2/2010 | Brenner et al. | |
| 7,736,382 B2 | 6/2010 | Webb et al. | |
| 7,747,318 B2 | 6/2010 | John et al. | |
| 7,756,588 B2 | 7/2010 | Jog et al. | |

(56) References Cited

U.S. PATENT DOCUMENTS

| | | | |
|---|---|---|---|
| 7,771,374 B2 | 8/2010 | Slatkine | |
| 7,787,170 B2 | 8/2010 | Patel et al. | |
| 7,792,588 B2 | 9/2010 | Harding | |
| 7,797,029 B2 | 9/2010 | Gibson et al. | |
| 7,801,601 B2 | 9/2010 | Maschino et al. | |
| 7,833,257 B2* | 11/2010 | Walsh et al. | 607/88 |
| 7,865,236 B2 | 1/2011 | Cory et al. | |
| 7,873,085 B2 | 1/2011 | Babushkin et al. | |
| 7,883,535 B2 | 2/2011 | Cantin et al. | |
| 7,883,536 B1* | 2/2011 | Bendett et al. | 607/89 |
| 7,894,905 B2 | 2/2011 | Pless et al. | |
| 7,899,512 B2 | 3/2011 | Labadie et al. | |
| 7,904,139 B2 | 3/2011 | Chance | |
| 7,914,842 B1 | 3/2011 | Greenberg et al. | |
| 7,951,181 B2* | 5/2011 | Mahadevan-Jansen et al. | 607/89 |
| 7,962,192 B2 | 6/2011 | Bodduluri | |
| 7,988,688 B2 | 8/2011 | Webb et al. | |
| 8,012,189 B1* | 9/2011 | Webb et al. | 607/89 |
| 8,078,263 B2 | 12/2011 | Zeman et al. | |
| 8,136,531 B2 | 3/2012 | Chariff | |
| 8,160,696 B2* | 4/2012 | Bendett et al. | 607/3 |
| 8,197,539 B2 | 6/2012 | Nasiatka et al. | |
| 8,207,211 B2 | 6/2012 | Wharton et al. | |
| 8,355,793 B2* | 1/2013 | Dadd et al. | 607/57 |
| 8,357,187 B1* | 1/2013 | Bendett et al. | 607/89 |
| 8,396,570 B2* | 3/2013 | Dadd et al. | 607/137 |
| 2002/0002391 A1 | 1/2002 | Gerdes | |
| 2003/0236458 A1 | 12/2003 | Hochman | |
| 2004/0143190 A1 | 7/2004 | Schnitzer | |
| 2005/0099824 A1 | 5/2005 | Dowling et al. | |
| 2005/0143789 A1 | 6/2005 | Whitehurst et al. | |
| 2006/0129210 A1* | 6/2006 | Cantin et al. | 607/88 |
| 2006/0161218 A1 | 7/2006 | Danilov | |
| 2006/0161227 A1* | 7/2006 | Walsh et al. | 607/88 |
| 2006/0167564 A1 | 7/2006 | Flaherty et al. | |
| 2006/0178711 A1* | 8/2006 | Patrick et al. | 607/57 |
| 2006/0235500 A1* | 10/2006 | Gibson et al. | 607/137 |
| 2006/0276861 A1 | 12/2006 | Lin | |
| 2007/0053996 A1 | 3/2007 | Boyden et al. | |
| 2007/0054319 A1 | 3/2007 | Boyden et al. | |
| 2007/0093798 A1* | 4/2007 | DeBenedictis et al. | 606/12 |
| 2007/0191906 A1 | 8/2007 | Iyer et al. | |
| 2007/0261127 A1 | 11/2007 | Boyden et al. | |
| 2008/0009748 A1 | 1/2008 | Gratton et al. | |
| 2008/0077200 A1 | 3/2008 | Bendett et al. | |
| 2008/0161697 A1 | 7/2008 | Chance | |
| 2008/0221640 A1* | 9/2008 | Overstreet et al. | 607/48 |
| 2008/0299201 A1 | 12/2008 | Kozloski et al. | |
| 2008/0306576 A1 | 12/2008 | Boyden et al. | |
| 2009/0030327 A1 | 1/2009 | Chance | |
| 2009/0043359 A1* | 2/2009 | Smoorenburg | 607/57 |
| 2009/0054954 A1 | 2/2009 | Foley | |
| 2009/0062685 A1 | 3/2009 | Bergethon et al. | |
| 2009/0069871 A1* | 3/2009 | Mahadevan-Jansen et al. | 607/89 |
| 2009/0076569 A1* | 3/2009 | Busby et al. | 607/57 |
| 2009/0099441 A1 | 4/2009 | Giszter et al. | |
| 2009/0163982 A1 | 6/2009 | deCharms | |
| 2009/0177247 A1 | 7/2009 | Neal et al. | |
| 2009/0177255 A1* | 7/2009 | Merfeld | 607/89 |
| 2009/0210039 A1* | 8/2009 | Boyden et al. | 607/89 |
| 2009/0312769 A1* | 12/2009 | Dadd et al. | 606/129 |
| 2010/0016732 A1* | 1/2010 | Wells et al. | 600/476 |
| 2010/0049180 A1* | 2/2010 | Wells et al. | 606/12 |
| 2010/0114190 A1* | 5/2010 | Bendett et al. | 607/3 |
| 2010/0145418 A1 | 6/2010 | Zhang et al. | |
| 2010/0162109 A1 | 6/2010 | Chatterjee et al. | |
| 2010/0174329 A1* | 7/2010 | Dadd et al. | 607/3 |
| 2010/0174330 A1* | 7/2010 | Dadd et al. | 607/3 |
| 2010/0174344 A1* | 7/2010 | Dadd et al. | 607/57 |
| 2010/0184818 A1 | 7/2010 | Wharton et al. | |
| 2010/0191079 A1 | 7/2010 | Shoureshi et al. | |
| 2010/0191308 A1 | 7/2010 | Meister | |
| 2010/0197995 A1* | 8/2010 | Wenzel et al. | 600/25 |
| 2010/0198317 A1 | 8/2010 | Lenarz et al. | |
| 2010/0262212 A1* | 10/2010 | Shoham et al. | 607/88 |
| 2010/0292629 A1* | 11/2010 | Dacey et al. | 604/8 |
| 2010/0292758 A1 | 11/2010 | Lee et al. | |
| 2010/0331912 A1* | 12/2010 | Tass et al. | 607/54 |
| 2011/0029041 A1* | 2/2011 | Wiskerke | 607/57 |
| 2011/0172680 A1 | 7/2011 | Younge et al. | |
| 2011/0172725 A1 | 7/2011 | Wells et al. | |
| 2011/0196239 A1* | 8/2011 | Behrend et al. | 600/476 |
| 2011/0202114 A1* | 8/2011 | Kessel et al. | 607/88 |
| 2011/0295331 A1* | 12/2011 | Wells et al. | 607/3 |
| 2011/0295344 A1 | 12/2011 | Wells et al. | |
| 2011/0295345 A1 | 12/2011 | Wells et al. | |
| 2012/0197374 A1* | 8/2012 | Vogt et al. | 607/137 |
| 2012/0226334 A1* | 9/2012 | Gardiner et al. | 607/88 |
| 2013/0303838 A1* | 11/2013 | Ahn et al. | 600/28 |
| 2014/0324138 A1* | 10/2014 | Wentz et al. | 607/92 |

FOREIGN PATENT DOCUMENTS

| | | |
|---|---|---|
| WO | WO 2010011404 A2 | 1/2010 |
| WO | WO-2011120540 | 10/2011 |
| WO | PCTUS1131866 | 11/2012 |

OTHER PUBLICATIONS

Loizou P., Mimicking the human ear, IEEE Signal Processing Magazine, Sep. 1998.*

Rubenstein J., How cochlear implants encode speech, Curr Opin Otolaryngol Head Neck Surg 12: 444-448, 2004.*

Harris et al., Optical nerve stimulation for a vestibular prosthesis, Proc. SPIE 7180-21, 5, 2009.*

American Speech Language Hearing Association, Cochlear implants, 2004. Available from www.asha.org/policy (Dates on the last page).*

Somek et al., Coding strategies for cochlear implants, ATKAAF 47(1-2), 69-74, 2006.*

Allegre, et al., "Stimulation in the rat of a nerve fiber bundle by a short UV pulse from an excimer laser", "NeuroScience Letters", 1994, pp. 261-264, vol. 180.

Arora, Komal, et al., "Electrical stimulation rate effects on speech perception in cochlear implants", "International Journal of Audiology", 2009, pp. 561-567, vol. 48.

Arridge, et al., "The theoretical basis for the determination of optical pathlengths in tissue: temporal and frequency analysis", "Phys. Med. Biol.", 1992, pp. 1531-1560, vol. 37.

Augustine, George J., "Combining patch-clamp and optical methods in brain slices", "Journal of Neuroscience Methods", 1994, pp. 163-169, vol. 54.

Banghart, Matthew, et al., "Light-activated ion channels for remote control of neuronal firing", "Nature Neuroscience", Nov. 21, 2004, pp. 1381-1386, vol. 7, No. 12.

Bernstein, Jacob G., et al., "Prosthetic systems for therapeutic optical activation and silencing of genetically-targeted neurons", "Proc Soc Photo Opt Instrum Eng.", May 5, 2008, vol. 6854: 68540H.

Boyden, Edward S., et al., "Millisecond-timescale, genetically targeted optical control of neural activity", "Nature Neuroscience", Sep. 2005, pp. 1263-1268, vol. 8, No. 9.

Bureau, Ingrid, et al., "Precise Development of Functional and Anatomical Columns in the Neocortex", "Neuron", Jun. 10, 2004, pp. 789-801, vol. 42.

Chambers, James J., et al., "Light-Induced Depolarization of Neurons Using a Modified Shaker K+ Channel and a Molecular Photoswitch", "Journal of Neurophysiology", Jul. 26, 2006, pp. 2792-2796, vol. 96.

Chance, et al., "Comparison of time-resolved and -unresolved measurements of deoxyhemoglobin in brain", "Proc. Nati. Acad. Sci. USA", Jul. 1988, pp. 4971-4975, vol. 85.

Deal, Walter J., et al., "Photoregularion of Biol. Activity by Photochromic Reagents, 3. Photoreg. of Bioelectricity by Acetylcholine Receptor Inh", "Proc. Natl. Acad. Sci.", 1969, pp. 1230-1234, vol. 64, No. 4.

Desmurget, et al., "Movement Intention after Parietal Cortex Stimulation in Humans", "Science", May 8, 2009, pp. 811-813, vol. 324.

(56) References Cited

OTHER PUBLICATIONS

Dodt, H.-U., et al., "Precisely Localized LTD in the Neocortex Revealed by Infrared-Guided Laser Stimulation.", "Science", Oct. 1, 1999, pp. 110-113, vol. 286.
Dodt, H.-U., et al., "Circuitry of rat barrel cortex investigated by infrared-guided laser stimulation", "NeuroReport", Mar. 24, 2003, pp. 623-627, vol. 14, No. 4.
Eder, Matthias, et al., "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.
Fork, Richard L., "Laser Stimulation of Nerve Cells in Aplysia", "Science, New Series", Mar. 5, 1971, pp. 907-908, vol. 171, No. 3974.
Fu, Qian-Jie, et al., "Effect of Stimulation Rate on Phoneme Recognition by Nucleus-22 Cochlear Implant Listeners", "J. Acoust. Soc. Am.", Jan. 2000, pp. 589-597, vol. 107, No. 1.
Fu, Qian-Jie, et al., "Effects of Dynamic Range and Amplitude Mapping on Phoneme Recognition in Nucleus-22 Cochlear Implant Users", "Ear and Hearing", 2000, pp. 227-235, vol. 21.
Han, Xue, et al., "Multiple-Color Optical Activation, Silencing, and Desynchronization of Neural Activity, with Single-Spike Temporal Resol", "PLoS ONE 2(3): e299. doi:10.1371/journal.pone. 0000299", Mar. 2007, pp. e299, No. 3, Publisher: www.plosone.org.
Harner, et al., "Improved Preservation of Facial Nerve Function With Use of Electrical Monitoring During Removal of Acoustic Neuromas", "Mayo Clinic Proceedings. Mayo Clinic", Feb. 1987, pp. 92-102, vol. 62.
Heinz, Michael G., et al., "Response Growth with Sound Level in Auditory-Nerve Fibers After Noise-Induced Hearing Loss", "J. Neurophysiology", 2004, pp. 784-795, vol. 91.
Izzo, et al., "Laser Stimulation of the Auditory Nerve", "Lasers in Surgery and Medicine", 2006, Publisher: Wiley-Liss, Inc.
Izzo, et al., "Selectivity of neural stimulation in the auditory system: a comparison of optic and electric stimuli", "Journal of Biomedical Optics", Mar./Apr. 2007, pp. 021008, vol. 12, No. 2.
Izzo, Agnella D., et al., "Optical Parameter Variability in Laser Nerve Stimulation: A Study of Pulse Duration, Repetition Rate, and Wavelength.", "IEEE Transactions on Biomedical Engineering", Jun. 2007, pp. 1108-1114, vol. 54, No. 6(1).
Littlefield, Philip D., et al., "Laser Stimulation of Single Auditory Nerve Fibers", "Laryngoscope", Oct. 2010, pp. 2071-2082, vol. 120.
Loizou, Philipos C., "Speech Processing in Vocoder-Centric Cochlear Implants", "Adv. Oto-Rhino-Laryngolog", 2006, pp. 109-143, vol. 64.
Maiorov, M., et al., "218 W quasi-CW operation of 1.83 urn two-dimensional laser diode array", "Electronics Letters", Apr. 15, 1999, pp. 636-638, vol. 35, No. 8.
Makeieff, et al., "Continuous Facial Nerve Monitoring During Pleomorphic Adenoma Recurrence Surgery", "The Laryngoscope", Jul. 2005, pp. 1310-1314.
Matthies, et al., "Direct Brainstem Recording of Auditory Evoked Potentials During Vestibular Schwannoma Resection: Nuclear BAEP Recording", "J. Neurosurg.", Jun. 1997, pp. 1057-1062, vol. 86.
McKay, et al., "Loudness Perception with Pulsatile Electrical Stimulation: The Effect of Interpulse Intervals", 1998.
McKay, et al., "Loudness Summation for Pulsatile Electrical Stimulation of the Cochlea: Effects of Rate, Electrode Separation, Level, an", "J. Acoust. Soc. Am.", Sep. 2001, pp. 1514-1524, vol. 110.
Meier, et al., "Continuous Intraoperative Facial Nerve Monitoring in Predicting Postoperative Injury During Parotidectomy", "The Laryngoscope", Sep. 2006, pp. 1569-1572, vol. 116.
Moller, Aage R., "History of Cochlear Implants and Auditory Brainstem Implants", "Adv Otorhinolaryngol. Basel, Karger", 2006, pp. 1-10, vol. 64.
Moller, et al., "Intraoperative Neurophysiologic Monitoring", "American Journal of Otology", Jan. 1995, pp. 115-117, vol. 16, No. 1.
Naples, et al., "A spiral nerve cuff electrode for peripheral nerve stimulation", "IEEE Trans Biomed Eng", Nov. 1988, pp. 905-916, vol. 35, No. 11.
Nelson, et al., "Intensity Discrimination as a Function of Stimulus Level with Electric Stimulation", "J. Acoust. Soc. Am.", Oct. 1996, pp. 2393-2414, vol. 100.
Omran, Sherif Abdellatif, et al., "Semitone Frequency Mapping to Improve Music Representation for Nucleus Cochlear Implants", "EURASIP Journal on Audio, Speech, and Music Processing", 2011, vol. 2011:2.
Princeton Lightwave (Company), "High Power Multimode Laser Arrays", "www.princetonlightwave.com/content/pli_high_power_multimode_laser_arrays.pdf", Dec. 24, 2005 downloaded.
Princeton Lightwave (Company), "High Power Water Cooled Laser Stack", "http://www.princetonlightwave.com/content/pli_high_power_multimode_laser_stacks.pdf", Oct. 24, 2005 downloaded.
Princeton Lightwave (Company), "High Power Single Element Laser", "www.princetonlightwave.com/content/HP%20Single%20Element%20Laser%20version%202.pdf", 2005 (downloaded).
Rolfe, "In Vivo Near-Infrared Spectroscopy", "Annu. Rev. Biomed. Eng.", 2000, pp. 715-754, vol. 2.
Schiefer, et al., "A Model of Selective Activation of the Femoral Nerve with a Flat Interface Nerve Electrode for a Lower Extremity Neuropr", "IEEE Trans Neural Syst Rehabil Eng", Apr. 2008, pp. 195-204, vol. 16, No. 2.
Schwartz, et al., "Auditory Brainstem Implants", "Neurotherapeutics: The Journal of the American Society for Experimental NeuroTherapeutics", Jan. 2008, pp. 128-136, vol. 5.
Tarler, et al., "Comparison of joint torque evoked with monopolar and tripolar-cuff electrodes", "IEEE Trans Neural Syst Rehabil Eng ", 2003, pp. 227-235, vol. 11, No. 3.
Teudt, et al., "Optical Stimulation of the Facial Nerve: A New Monitoring Technique?", "The Laryngoscope", 2007, pp. 1641-1647, vol. 117, No. 9.
Tonn, et al., "Acoustic Neuroma Surgery as an Interdisciplinary Approach: A Neurosurgical Series of 508 Patients", "Journal of Neurology, Neurosurgery and Psychiatry", Aug. 2000, pp. 161-166, vol. 69, No. 2.
Vandali, et al., "Speech Perception as a Function of Electrical Stimulation Rate: Using the Nucleus 24 Cochlear Implant", Dec. 2000.
Vogel, Alfred, et al., "Mechanisms of pulsed laser ablation of biological tissues.", "Chemical Reviews", 2003, pp. 577-644, vol. 103, No. 2.
Wells, Jonathon, et al., "Application of Infrared Light for in vivo Neural Stimulation.", "Journal of Biomedical Optics", Nov. 2005, pp. 064003-1 to 064003-12, vol. 10, No. 6.
Wells, Jonathon, et al., "Optical stimulation of neural tissue in vivo", "Optics Letters", Mar. 1, 2005, pp. 504-506, vol. 30, No. 5.
Wells, Jonathon D., et al., "Optically Mediated Nerve Stimulation: Identification of Injury Thresholds.", "Lasers in Surgery and Medicine", Jul. 23, 2007, pp. 513-526, vol. 39.
Wells, Jonathon, et al., "Pulsed laser versus electrical energy for peripheral nerve stimulation", "Journal of Neuroscience Methods", 2007, pp. 326-337, vol. 163.
Witt, Robert L., "Facial Nerve Monitoring in Parotid Surgery: The Standard of Care?", "Otolaryngology—Head and Neck Surgery", Nov. 1998, pp. 468-470, vol. 119, No. 5.
Yoo, et al., "Selective recording of the canine hypoglossal nerve using a multicontact flat interface nerve electrode", "IEEE Trans Biomed Eng", Aug. 2005, pp. 1461-1469, vol. 52, No. 8.
Zemelman, Boris V., et al., "Photochemical gating of heterologous ion channels: Remote control over genetically designated populations of neurons", "Proceedings of the National Academy of Sciences", Feb. 4, 2003, pp. 1352-1357, vol. 100, No. 3.
Zhang, Feng, et al., "Channelrhodopsin-2 and optical control of excitable cells", "Nature Methods", Sep. 21, 2006, pp. 785-792, vol. 3, No. 10.

\* cited by examiner

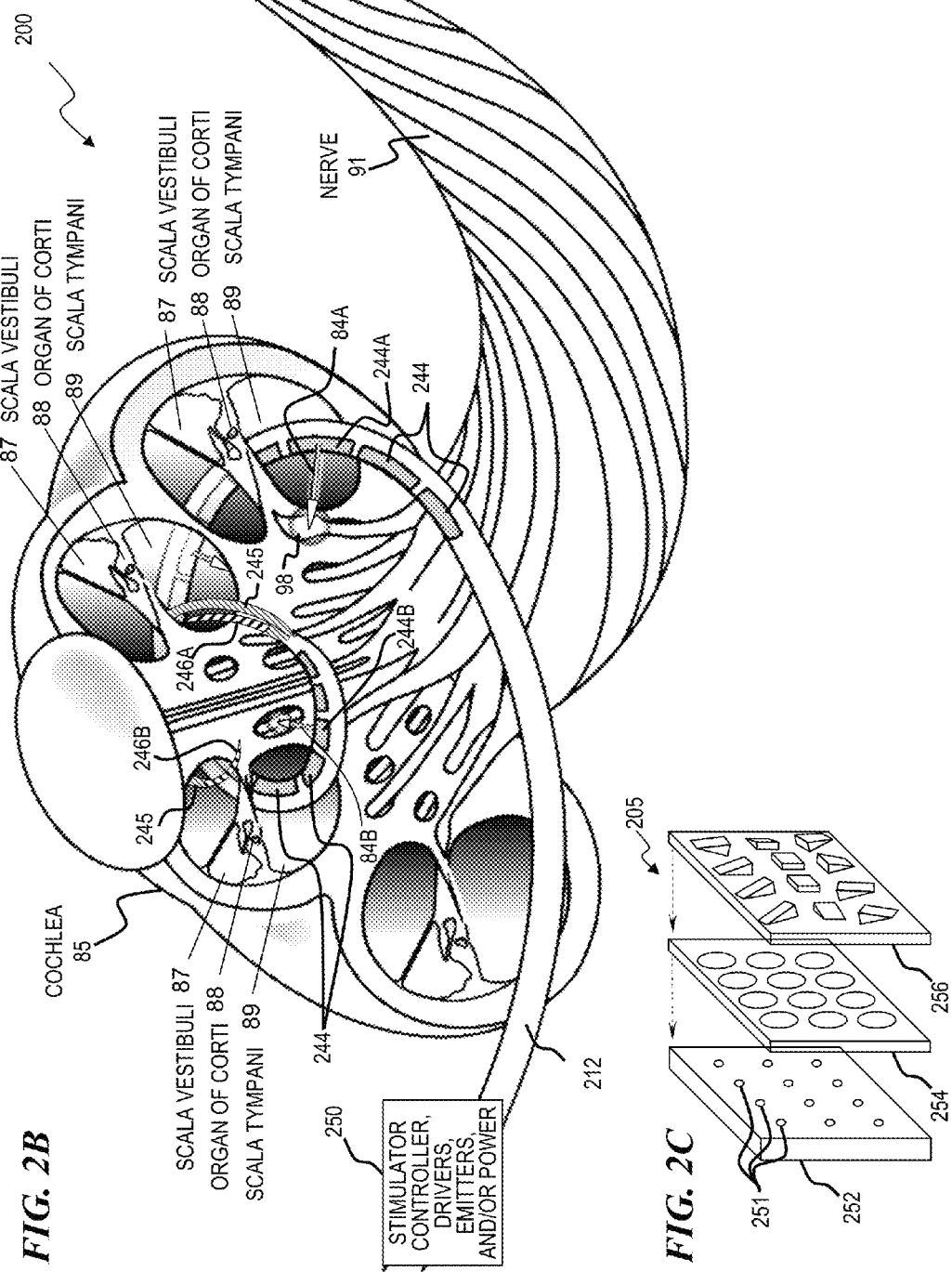

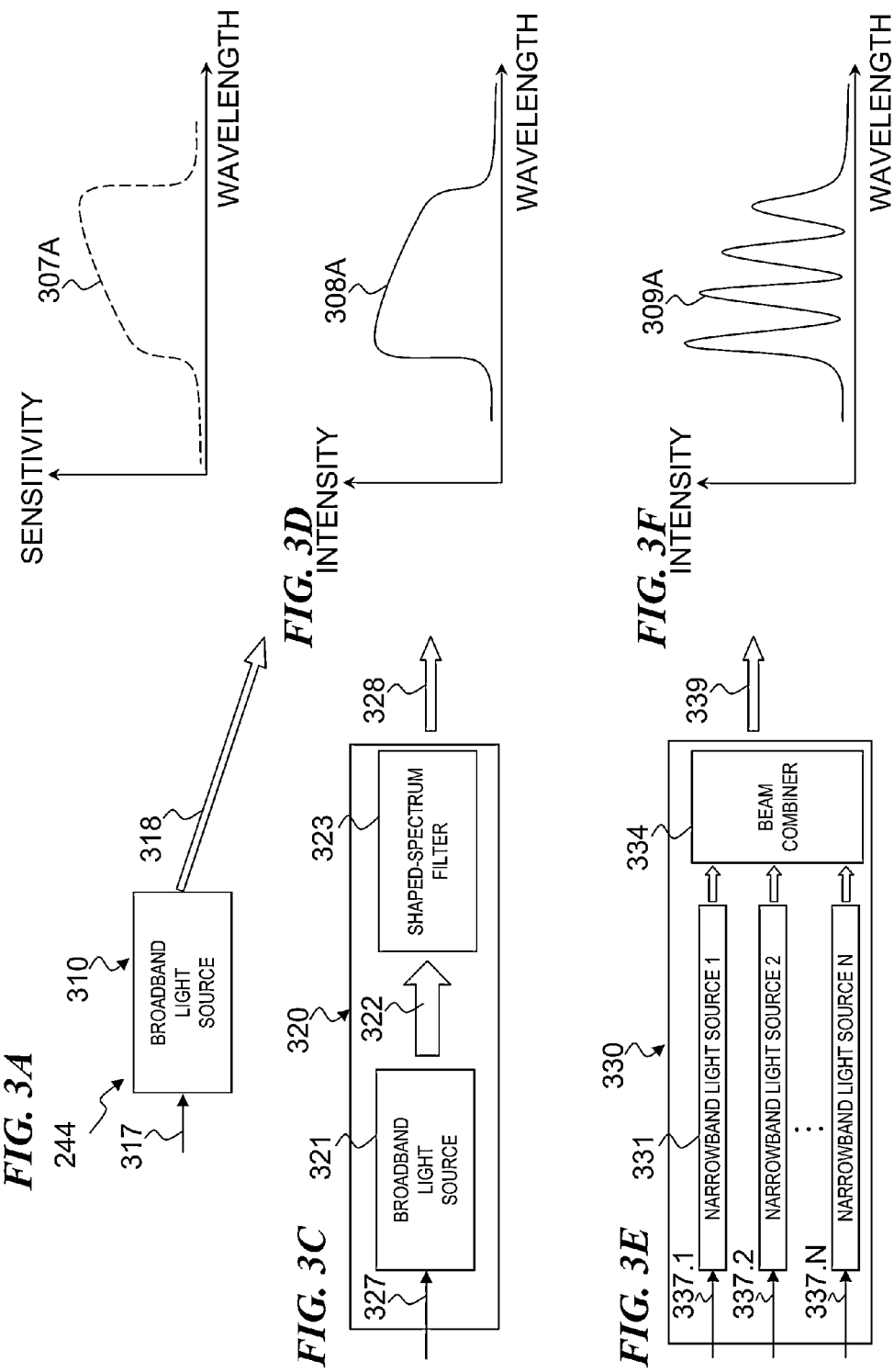

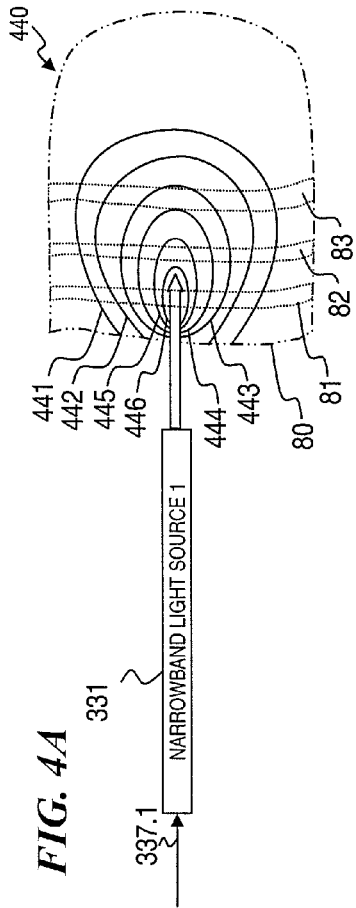
FIG. 3M
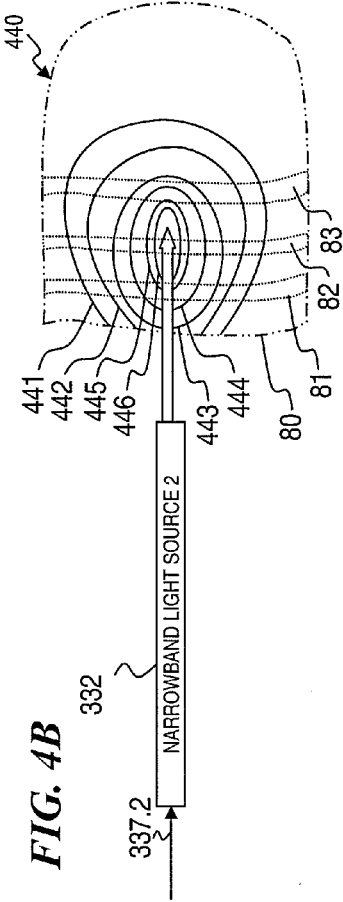
FIG. 4A
FIG. 4B
FIG. 4C
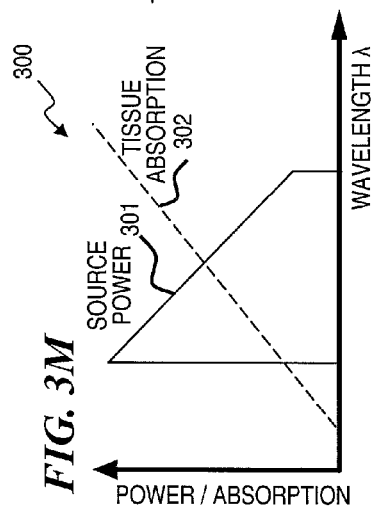
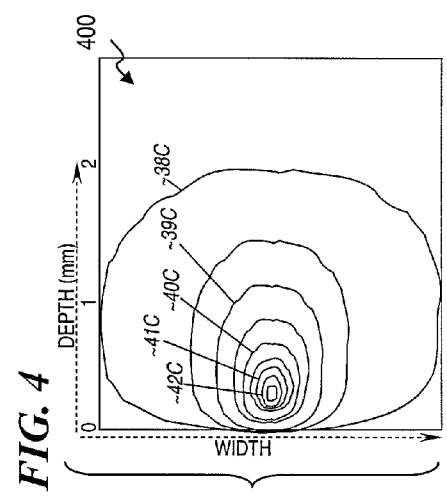
FIG. 4

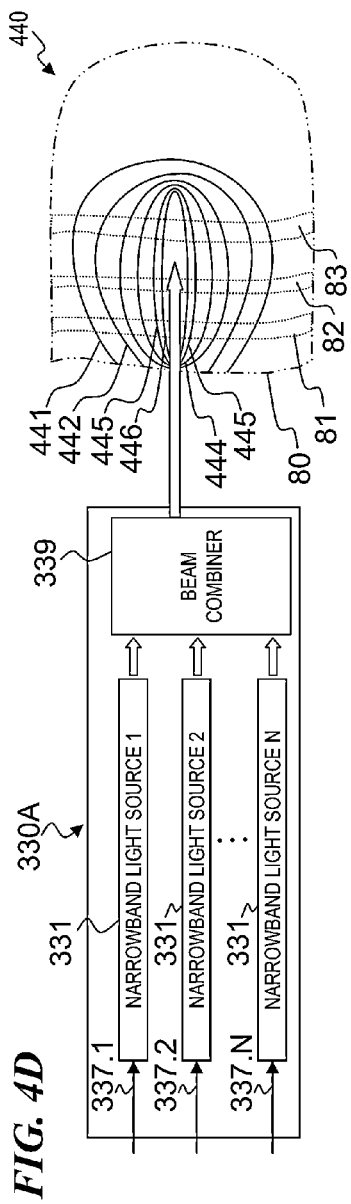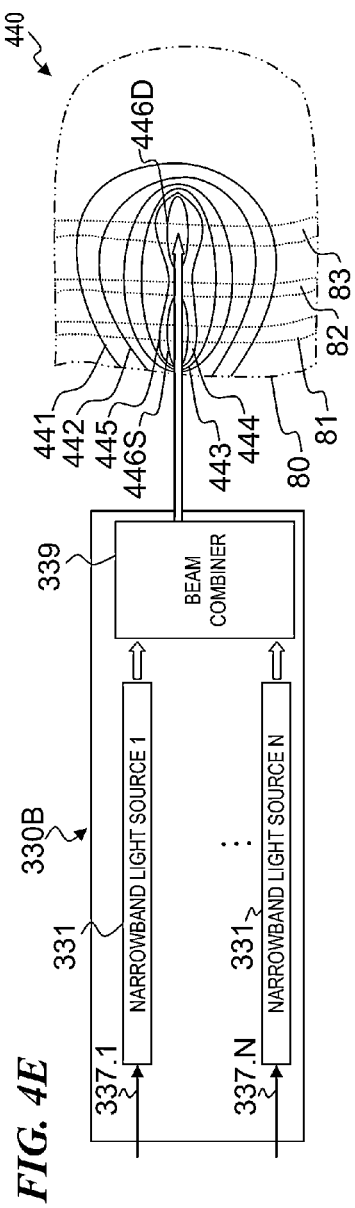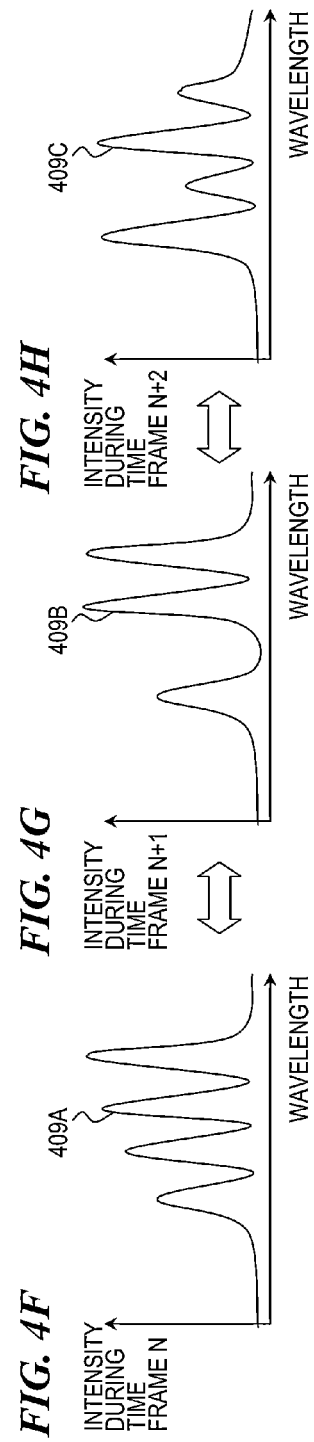

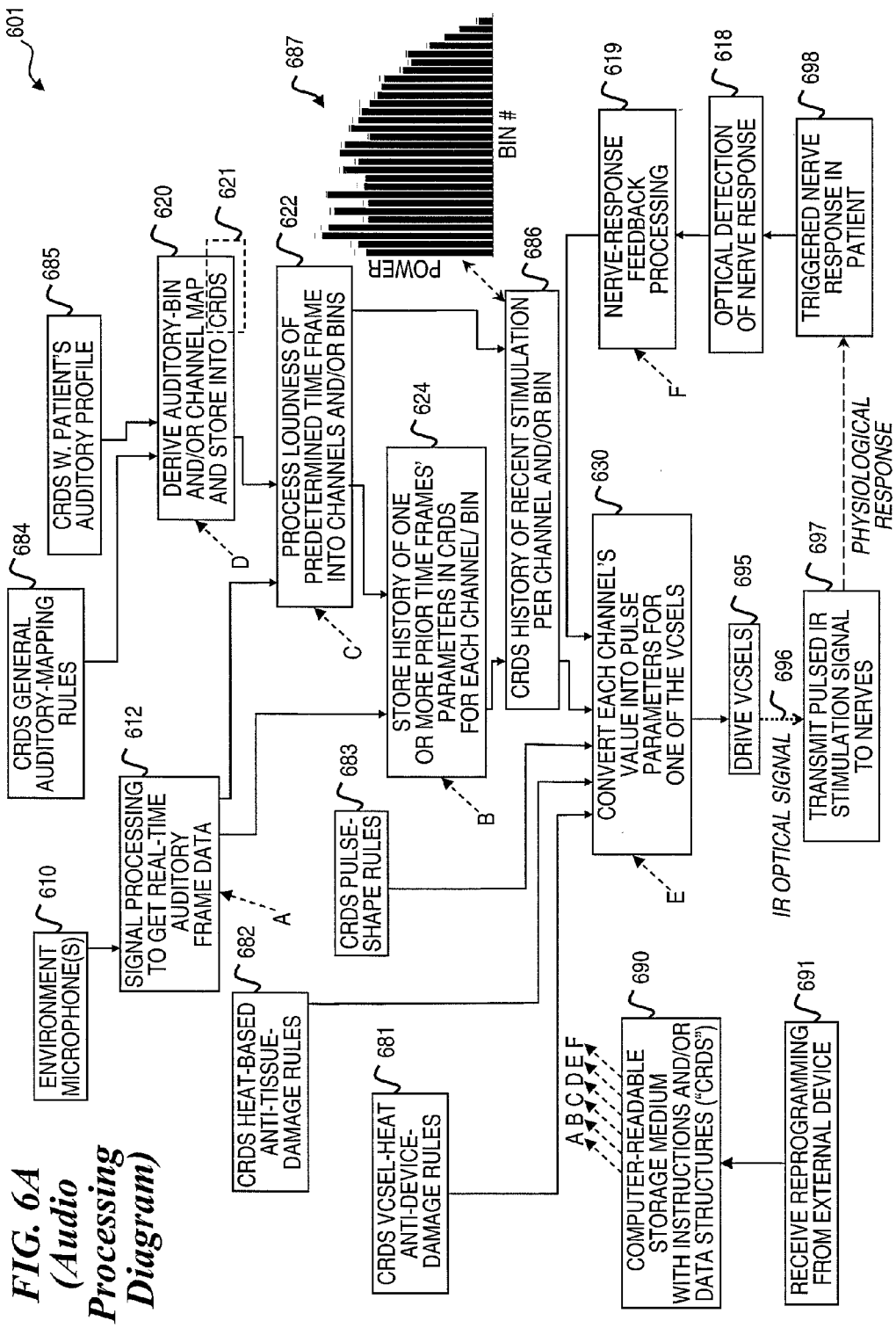
FIG. 6A (Audio Processing Diagram)

ACOUSTIC HEARING
DYNAMIC RANGE
IS VERY WIDE

INDIVIDUALLY OPTIMIZED PERFORMANCE OF OPTICALLY STIMULATING COCHLEAR IMPLANTS

CROSS-REFERENCE TO RELATED APPLICATIONS

This application claims priority benefit, under 35 U.S.C. §119(e), of
U.S. Provisional Patent Application No. 61/511,020 filed Jul. 22, 2011 by Ryan C. Stafford, titled "Method and Apparatus for Optimizing an Optically Stimulating Cochlear Implant";
U.S. Provisional Patent Application No. 61/511,048 filed Jul. 23, 2011 by Ryan C. Stafford, titled "Broad Wavelength Profile to Homogenize the Absorption Profile in Optical Stimulation of the Cochlea"; and
U.S. Provisional Patent Application No. 61/511,050 filed Jul. 23, 2011 by Ryan C. Stafford et al., titled "Optical Cochlear Implant with Electrode(s) at the Apical End for Stimulation of Apical Spiral Ganglion Cells of the Cochlea";
each of which is incorporated herein by reference in its entirety.

This invention is related to:
U.S. patent application Ser. No. 13/555,091 filed on Jul. 21, 2012 by Ryan C. Stafford et al. and titled "OPTICAL-STIMULATION COCHLEAR IMPLANT WITH ELECTRODE(S) AT THE APICAL END FOR ELECTRICAL STIMULATION OF APICAL SPIRAL GANGLION CELLS OF THE COCHLEA" (which issued as U.S. Pat. No. 8,834,545 on Sep. 16, 2014),
U.S. patent application Ser. No. 13/555,092 filed on Jul. 21, 2012 by Ryan C. Stafford and titled "BROAD WAVELENGTH PROFILE TO HOMOGENIZE THE ABSORPTION PROFILE IN OPTICAL STIMULATION OF NERVES,"
U.S. patent application Ser. No. 13/555,094 filed on Jul. 21, 2012 by Ryan C. Stafford et al. and titled "COCHLEAR IMPLANT AND METHOD ENABLING ENHANCED MUSIC PERCEPTION" (which issued as U.S. Pat. No. 8,747,447 on Jun. 10, 2014),
U.S. patent application Ser. No. 13/555,095 filed on Jul. 21, 2012 by Ryan C. Stafford et al. and titled "COCHLEAR IMPLANT USING OPTICAL STIMULATION WITH ENCODED INFORMATION DESIGNED TO LIMIT HEATING EFFECTS" (which issued as U.S. Pat. No. 8,840,654 on Sep. 23, 2014),
U.S. patent application Ser. No. 13/555,097 filed on Jul. 21, 2012 by Ryan C. Stafford et al. and titled "OPTICAL PULSE-WIDTH MODULATION USED IN AN OPTICAL-STIMULATION COCHLEAR IMPLANT" (which issued as U.S. Pat. No. 8,894,697 on Nov. 25, 2014), and
U.S. patent application Ser. No. 13/555,098 filed on Jul. 21, 2012 by Ryan C. Stafford et al. and titled "OPTIMIZED STIMULATION RATE OF AN OPTICALLY STIMULATING COCHLEAR IMPLANT" (published as U.S. Patent Application Publication US 2013/0023965 on Jan. 24, 2013),
each of which is incorporated herein by reference in its entirety.

This invention is also related to:
U.S. Pat. No. 7,736,382 titled "Apparatus for Optical Stimulation of Nerves and other Animal Tissue" that issued Jun. 15, 2010 to James S. Webb et al.,
U.S. Pat. No. 7,988,688 titled "Miniature Apparatus and Method for Optical Stimulation of Nerves and other Animal Tissue" that issued Aug. 2, 2011 to James S. Webb et al.,
U.S. patent application Ser. No. 11/948,912 filed Nov. 30, 2007 by James S. Webb et al., titled "Apparatus and Method for Characterizing Optical Sources used with Human and Animal Tissues" (which issued as U.S. Pat. No. 8,929,973 on Jan. 6, 2015),
U.S. Patent Application Publication US 2008/0077200 of Mark P. Bendett et al., dated Mar. 27, 2008 and titled "Apparatus and Method for Stimulation of Nerves and Automated Control of Surgical Instruments,"
U.S. Pat. No. 8,012,189 titled "Vestibular Implant using Optical Stimulation of Nerves" that issued Sep. 6, 2011 to James S. Webb et al.,
U.S. Pat. No. 7,883,536 titled "Hybrid Optical-Electrical Probes" that issued Feb. 8, 2011 to Mark P. Bendett et al.,
U.S. patent application Ser. No. 12/191,301 filed Aug. 13, 2008 by Mark P. Bendett et al., titled "VCSEL Array Stimulator Apparatus and Method for Light Stimulation of Bodily Tissues" (which issued as U.S. Pat. No. 8,475,506 on Jul. 2, 2013),
U.S. Patent Application Publication US 2010/0049180 of Jonathon D. Wells et al., dated Feb. 25, 2010 and titled "System and Method for Conditioning Animal Tissue Using Laser Light,"
U.S. Pat. No. 8,160,696 titled "Nerve Stimulator and Method using Simultaneous Electrical and Optical Signals" that issued Apr. 17, 2012 to Mark P. Bendett et al.,
U.S. Patent Application Publication US 2011/0172725 of Jonathon D. Wells et al., dated Jul. 14, 2011 and titled "Nerve Stimulator and Method using Simultaneous Electrical and Optical Signals" (which issued as 8,498,699 on Jul. 30, 2013),
U.S. Patent Application Publication US 2010/0292758 of Daniel J. Lee et al., dated Nov. 18, 2010 and titled "Optical Stimulation of the Brainstem and/or Midbrain, Including Auditory Areas" (which issued as U.S. Pat. No. 8,744,570 on Jun. 3, 2014),
U.S. Patent Application Publication US 2011/0295331 of Jonathon D. Wells et al., dated Dec. 1, 2011 and titled "Laser-Based Nerve Stimulators for, e.g., Hearing Restoration in Cochlear Prostheses and Method" (which issued as U.S. Pat. No. 8,792,978 on Jul. 29, 2014),
U.S. Patent Application Publication US 2011/0295345 of Jonathon D. Wells et al., dated Dec. 1, 2011 and titled "Implantable Infrared Nerve Stimulation Devices for Peripheral and Cranial Nerve Interfaces,"
U.S. Patent Application Publication US 2011/0295346 of Jonathon D. Wells et al., dated Dec. 1, 2011 and titled "Cuff Apparatus and Method for Optical and/or Electrical Nerve Stimulation of Peripheral Nerves" (which issued as U.S. Pat. No. 8,652,187 on Feb. 18, 2014),
U.S. Patent Application Publication US 2011/0295347 of Jonathon D. Wells et al., dated Dec. 1, 2011 and titled "Nerve-Penetrating Apparatus and Method for Optical and/or Electrical Nerve Stimulation of Peripheral Nerves" (which issued as U.S. Pat. No. 8,968,376 on Mar. 3, 2015),
U.S. Patent Application Publication US 2011/0295344 of Jonathon D. Wells et al., dated Dec. 1, 2011 and titled "Optical Bundle Apparatus and Method For Optical and/or Electrical Nerve Stimulation of Peripheral Nerves" (which issued as U.S. Pat. No. 8,864,806 on Oct. 21, 2014),
U.S. Provisional Patent Application 61/349,810 filed May 28, 2010 by Jonathon D. Wells et al., titled "Implantable Infrared Nerve Stimulation Devices for Peripheral and Cranial Nerve Interfaces," and
U.S. Provisional Patent Application 61/386,461 filed Sep. 24, 2010 by Jonathon D. Wells et al., titled "Implantable Infrared Nerve Stimulation Devices for Peripheral and Cranial Nerve Interfaces," each of which is incorporated herein by reference in its entirety including all appendices.

FIELD OF THE INVENTION

The invention relates generally to optical stimulation of nerves to restore hearing, and more particularly to apparatus and methods for optimizing the performance of a cochlear implant for an individual.

BACKGROUND OF THE INVENTION

The commercialization of cochlear implants, which directly stimulate the auditory nerve to provide hearing to the profoundly deaf, is somewhat recent (introduced in 1984 as an FDA-approved device). These conventional devices utilize the compound nerve action potential (CNAP) produced by the presence of an electric field in proximity of the spiral ganglion cells within the cochlea. In such conventional devices, acoustic sounds from the environment are digitized, separated into a plurality of frequency bands (called "audio-frequency channels" herein) and the loudness envelope of the signal in all of the audio-frequency channels carries the information necessary to generate electrical signals to stimulate cochlear nerves to allow the patient to perceive speech and other pertinent sounds. In electrical cochlear implants, pulsatile electric currents are modulated in amplitude to convey this information to the listener. Pulse-repetition rate and pulse width would typically be held constant, while pulse amplitude is modulated to follow relative changes in loudness. While electrical cochlear implants can be effective, they often lack the specificity to target the desired auditory nerve pathway without also activating other auditory nerve pathways as a side effect (because electrical current spreads in the body, most if not all neuromodulation devices wind up stimulating other nerves in the area besides the intended target (thus potentially causing, for example, unintended hearing sensations)). The presence of a stimulation artifact can also obfuscate signals elsewhere along the auditory nerve, which precludes stimulating and recording electrical nerve activity in the same location.

As used herein, the auditory-nerve pathway includes all of the nerves from and including the cochlea, to and including the brain stem.

The discovery that neural compound action potentials (CAPs) can be evoked by pulsed optical stimulation has led to development of cochlear implants based on optical stimulation (e.g., see U.S. Pat. No. 8,012,189 issued Sep. 6, 2011 to James S. Webb et al., titled "Vestibular Implant using Optical Stimulation Of Nerves," and U.S. Patent Application Publication US 2011/0295331 of Jonathon D. Wells et al., dated Dec. 1, 2011 and titled "Laser-Based Nerve Stimulators for, e.g., Hearing Restoration in Cochlear Prostheses and Method" (which issued as U.S. Pat. No. 8,792,978 on Jul. 29, 2014), both of which are incorporated herein by reference, and both of which are assigned to Lockheed Martin Corporation, the assignee of the present invention). Optical stimulation provides more precise neural stimulation compared to electrical stimulation methods because light is directed in a single direction, and there is no stimulation artifact. However, the physiological mechanism of optical stimulation is different than that of electrical stimulation. This leads to the challenge of encoding the information for the listener in a way that optimally exploits the physiological mechanism of optical stimulation.

U.S. Patent Application Publication US 2010/0049180 of Jonathon D. Wells et al., dated Feb. 25, 2010 and titled "System and Method for Conditioning Animal Tissue using Laser Light," is incorporated herein by reference in its entirety. Wells et al. describe systems and methods for prophylactic measures aimed at improving wound repair. In some embodiments, laser-mediated preconditioning would enhance surgical wound healing that was correlated with hsp70 expression. Using a pulsed laser ($\lambda$=1850 nm, Tp=2 ms, 50 Hz (in this context, Hz means stimulation pulses per second (pps)), H=7.64 mJ/cm$^2$) the skin of transgenic mice that contain an hsp70 promoter-driven luciferase were preconditioned 12 hours before surgical incisions were made. Laser protocols were optimized using temperature, blood flow, and hsp70-mediated bioluminescence measurements as benchmarks. Bioluminescent imaging studies in vivo indicated that an optimized laser protocol increased hsp70 expression by 15-fold. Under these conditions, healed areas from incisions that were laser-preconditioned were two times stronger than those from control wounds. Though useful for wound treatment and surgical pre-treating, chronic heating of tissue (such as the cochlea) is detrimental.

Other prior-art includes:

Qian-Jie Fu and Robert Shannon, "Effect of Stimulation Rate on Phoneme Recognition by Nucleus-22 Cochlear Implant Listeners," J. Acoust. Soc. Am., vol. 107, pp 589-597 (2000) (hereinafter Fu et al., 2000a);

Kandel et al., Eds., "Principles of Neural Science", McGraw-Hill Medical; 4$^{th}$ edition (January 2000), Ch 30-31 (hereinafter Kandel et al., 2000);

Loizou, "Speech Processing in Vocoder-Centric Cochlear Implants," Adv. Oto-Rhino-Laryngology, vol. 64, pp 109-143, Karger, (2006) (hereinafter Loizou, 2006);

Vandali et al., "Speech Perception as a Function of Electrical Stimulation Rate: Using the Nucleus 24 Cochlear Implant System," Ear and Hearing, vol. 21, pp 608-624, (December 2000) (hereinafter Vandali et al., 2000);

McKay, et al., "Loudness Summation for Pulsatile Electrical Stimulation of the Cochlea: Effects of Rate, Electrode Separation, Level, and Mode of Stimulation," J. Acoust. Soc. Am., vol. 110, pp 1514-24 (September 2001);

McKay, et al., "Loudness Perception with Pulsatile Electrical Stimulation: The Effect of Interpulse Intervals," J. Acoust. Soc. Am., vol. 104, pp 1061-74 (1998) (hereinafter McKay et al., 1998);

Littlefield et al., "Laser Stimulation of Single Auditory Nerve Fibers," Laryngoscope, vol. 120, pp 2071-82, (2010) (hereinafter Littlefield et al., 2010);

Heinz et al., "Response Growth with Sound Level in Auditory-Nerve Fibers After Noise-Induced Hearing Loss," J. Neurophysiology, vol. 91, pp 784-95 (2004) (hereinafter Heinz et al., 2004);

Fu & Shannon, "Effects of Dynamic Range and Amplitude Mapping on Phoneme Recognition in Nucleus-22 Cochlear Implant Users," Ear and Hearing, vol. 21, pp 227-235 (2000) (hereinafter Fu et al., 2000b);

Nelson et al., "Intensity Discrimination as a Function of Stimulus Level with Electric Stimulation," J. Acoust. Soc. Am., vol. 100, pp 2393-2414 (October 1996) (hereinafter Nelson et al., 1996);

Omran et al., "Semitone Frequency Mapping to Improve Music Representation for Nucleus Cochlear Implants," EURASIP Journal on Audio, Speech, and Music Processing, 2011:2 (2011) (hereinafter Omran et al., 2011); and Fischer, "Piano Tuning," Theodore Presser Co. (1907) (reprinted by Dover Publications, 1975) (hereinafter Fischer, 1907/1975); each of which is incorporated herein by reference.

There is a need for an improved apparatus and a corresponding method for optical (and optionally optical combined with electrical) stimulation of nerves to restore hearing.

BRIEF SUMMARY OF THE INVENTION

In some embodiments, the present invention provides an apparatus that includes a pulsed infrared (IR) light source. The pulsed IR light signal provides optical stimulation of nerves to generate nerve-action potentials (NAPs) in one or more individual nerve cells, and/or compound nerve-action potentials (CNAPs) in a nerve bundle. In some embodiments, the stimulation of NAPs and CNAPs is used to restore hearing.

In some embodiments, a plurality of parameters is specified by the computer program used to implement the optimization of the present invention, or specified to the program by the audiologist (or patient) utilizing the program, as potential mechanisms for optimizing implant performance for the individual patient. In some embodiments, the following parameters are used to encode information on the optical signal: pulse width, peak power, stimulation rate, wavelength, polarization, wavelength profile, beam profile, beam angle.

In some embodiments, the following parameters are used to optimize the implant performance during tuning of the device after implantation: pulse width, amplitude, frequency, wavelength, polarization, wavelength profile, beam profile, beam angle, coding strategy (e.g., N-of-M), signal-processing filter bandwidths, signal-processing filter shapes, signal-processing filter center frequencies, and operational/functioning channels.

One advantage of this solution is that the overall audio perception of the patient is improved because the operational parameters of the cochlear implant are more precisely adjusted to the patient's response to optical cochlear stimulation.

BRIEF DESCRIPTION OF THE FIGURES

Each of the items shown in the figures described in the following brief description of the drawings represents some embodiments of the present invention.

FIG. 2B is a schematic cutaway diagram illustrating an implanted cochlea-stimulation device 200 implanted such that a portion of device 200 is coiled within the cochlea 85.

FIG. 2C is a schematic perspective exploded-view diagram illustrating VCSEL array and focussing device 205, used for some embodiments of VCSEL emitters 244 of FIG. 2B.

FIG. 3A is a schematic diagram of a broadband wavelength source 310 having a designed power/wavelength spectrum profile formed to customize the absorption of optical power in the tissue of interest.

FIG. 3B includes a schematic graph 307A of a tissue sensitivity to optical stimulation for a first given type or composition of tissue as a function of the wavelength of the optical stimulation.

FIG. 3C is a schematic diagram of a broadband wavelength source 320 having a designed power/wavelength spectrum profile formed to customize the absorption of optical power in the tissue of interest.

FIG. 3D is a schematic graph 308A of a designed power/wavelength spectrum profile used to customize the absorption of optical power in the tissue.

FIG. 3E is a schematic diagram of a broadband wavelength source 330 having a designed power/wavelength spectrum profile formed to customize the absorption of optical power in the tissue of interest.

FIG. 3F is a schematic graph 309A of a designed power/wavelength spectrum profile used to customize the absorption of optical power in the tissue.

FIG. 3M includes a computer-simulation-derived plot of a temperature profile of tissue due to absorption of single-wavelength source 331 (see, e.g., FIG. 4A) of infrared light having a first wavelength.

FIG. 4 is a plot of a temperature profile of tissue due to absorption of single-wavelength source of infrared light.

FIG. 4A is a schematic diagram that includes a plot of a temperature profile of tissue due to absorption of single-wavelength source 331 of infrared light having a first wavelength.

FIG. 4B is a schematic diagram that includes a plot of a temperature profile of tissue due to absorption of single-wavelength source 332 of infrared light having a second wavelength.

FIG. 4C is a schematic diagram that includes a plot of a temperature profile of tissue due to absorption of single-wavelength source 333 of infrared light having a third wavelength.

FIG. 4D is a schematic diagram that includes a plot of a temperature profile of tissue due to absorption of source 330A of infrared light having a customized spectrum of wavelengths.

FIG. 4E is a schematic diagram that includes a plot of a temperature profile of tissue due to absorption of source 330B of infrared light having a customized spectrum of wavelengths.

FIG. 4F is a schematic graph 409A of a designed power/wavelength spectrum profile for a time period N in a sequence of time periods N, N+1, N+2 used to customize the temporal absorption of optical power in a plurality of tissues.

FIG. 4G is a schematic graph 409B of a designed power/wavelength spectrum profile for a time period N+1 in a sequence of time periods N, N+1, N+2 used to customize the temporal absorption of optical power in a plurality of tissues.

FIG. 4H is a schematic graph 409C of a designed power/wavelength spectrum profile for a time period N+2 in a sequence of time periods N, N+1, N+2 used to customize the temporal absorption of optical power in a plurality of tissues.

FIG. 6A is a flow chart of a method 601, according to some embodiments of the present invention.

DETAILED DESCRIPTION OF THE INVENTION

Although the following detailed description contains many specifics for the purpose of illustration, a person of ordinary skill in the art will appreciate that many variations and alterations to the following details are within the scope of the invention. Very narrow and specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The embodiments shown in the Figures and described here may include features that are not included in all specific embodiments. A particular embodiment may include only a subset of all of the features described, or a particular embodiment may include all of the features described.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Figure 1:
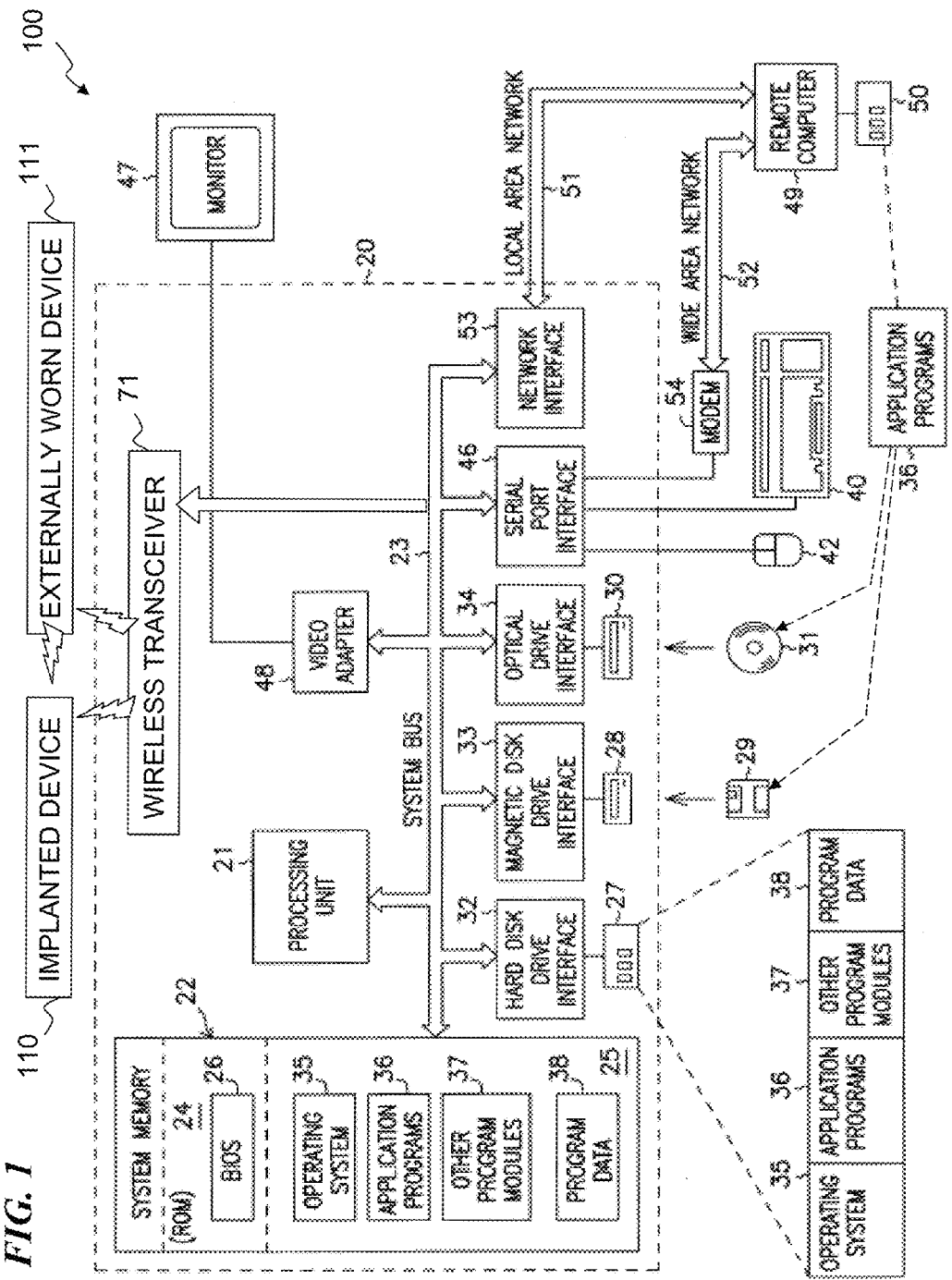
FIG. 1 is a schematic representation of a system 100 with a hardware- and operating-environment having an implanted device 110, an optional externally worn device 111 and a customization console computer 20.

FIG. 1 is an overview diagram of a hardware- and operating-environment (or system) 100 that is used in conjunction with embodiments of the invention. The description of FIG. 1 is intended to provide a brief, general description of suitable computer hardware and a suitable computing environment in conjunction with which the invention may be implemented. In some embodiments, the invention is described in the general context of computer-executable instructions, such as program modules, that are stored on computer-readable media and that are executed by a computer, such as a microprocessor residing in an implanted device (located within a patient) and/or in an external device worn by the patient and/or personal computer that is/are wirelessly linked to the implanted device. Generally, program modules include routines, programs, objects, components, data structures, and the like, that perform particular tasks or implement particular abstract data types.

In some embodiments, system 100 includes an audiologist- and/or user-control console computer 20 that is programmable and that has a wireless transceiver 71 that allows wireless control (i.e., reprogramming of the remote microprocessors) of the implanted device 110 (which includes a programmed microcontroller), and/or an externally worn device 111 (which also includes a programmed microcontroller) that wirelessly communicates and/or provides power to the implanted device 110. In some embodiments, application programs 36 stored on a computer-readable storage device (e.g., optical disk 31 (CDROM, DVD, Blu-ray Disc™ (BD), or the like), magnetic or FLASH storage device 29 (e.g., floppy disk, thumb drive, SDHC™ (Secure-Data High-Capacity) memory card or the like), and/or a storage device 50 connected to a remote computer 49 that connects to computer 20 across a local-area network 51 or a wide-area network 52 such as the internet) contain instructions and/or control structures (such as look-up tables, control parameters, databases and the like) that are processed and/or transmitted into the implanted device 110 to control its operation by methods of the present invention described herein. In some embodiments, the applications programs 36 are partially executed in the computer 20 and/or the externally worn device 111, and then partially executed in the implanted device 110.

Accordingly, in some embodiments, an audiologist and/or user can adjust parameters of the implanted optical-electrical-cochlear-stimulation device 110 to customize its operation to a much greater extent than is possible with a conventional electrical-stimulation cochlear implant, because implanted optical-electrical-cochlear-stimulation device 110 has a far greater number of parameters that can be finely adjusted (e.g., pulse width, amplitude, frequency, wavelength, polarization, wavelength profile, beam profile, beam angle, and, the like). In some embodiments, the applications programs 36 contain a substantial amount of safety control code that runs in computer 20 to guide the audiologist and/or user to adjust the parameters of the implanted optical-cochlear-stimulation device 110 and to help prevent operation that might harm the patient or damage the implanted device 110 (such as what might occur if too much optical energy were applied in a concentrated small area of the cochlea or within too short a period of time, or if overheating occurred in the device 110 due to too many VCSELs (vertical-cavity surface emitting lasers) next to one another being activated in a short period of time).

Although many of the embodiments herein have light-emitting elements that include VCSELs (vertical-cavity surface emitting lasers) implemented as electrically pumped semiconductor diode lasers, other embodiments of the present invention use edge-emitting semiconductor diode lasers, optically pumped semiconductor lasers, optically pumped optical-fiber lasers, light-emitting diodes, superluminescent devices, or any other suitable light source. Some embodiments use wavelengths in the range of 1.75 microns to 2 microns, other embodiments use any other suitable wavelengths.

Moreover, those skilled in the art will appreciate that the invention may be practiced with other computer-system configurations, including hand-held devices, multiprocessor systems, microprocessor-based or programmable consumer electronics, network PCs, minicomputers, mainframe computers, and the like. The invention may also be practiced in distributed computer environments where tasks are performed by remote processing and input-output (I/O) devices that are linked through a communications network. In a distributed-computing environment, program modules may be located in both local and remote storage devices.

As shown in FIG. 1, in some embodiments, the hardware- and operating-environment includes audiologist- and/or user-control console computer 20, or a server 20, including a processing unit 21, a system memory 22, and a system bus 23 that operatively couples various system components including the system memory 22 to the processing unit 21. In some embodiments, there may be only one, or in other embodiments, there may be more than one processing unit 21, such that the processor of computer 20 comprises a single central-processing unit (CPU), or a plurality of processing units, commonly referred to as a multi-processor or parallel-processing environment. In various embodiments, computer 20 may be implemented using a conventional computer, a distributed computer, or any other type of computer including those embedded in cell phones, personal-data-assistant devices or other form factors.

The system bus 23 can be any of several types of bus structures including a memory bus or memory controller, a peripheral bus, and a local bus using any of a variety of bus architectures. The system memory can also be referred to as simply the memory, and includes read-only memory (ROM) 24 and random-access memory (RAM) 25. A basic input/output system (BIOS) 26, containing the basic routines that help to transfer information between elements within the computer (or server) 20, such as during start-up, may be stored in ROM 24. The computer 20 further includes a hard disk drive 27 for reading from and writing to a magnetic hard disk, a removable-media drive or FLASH controller 28 for reading from or writing to a removable magnetic floppy-disk or FLASH storage device 29, and an optical disk drive 30 for reading from or writing to a removable optical disk 31 (such as a CDROM, DVD, Blu-ray Disc™ (BD) or other optical media).

The hard disk drive 27, magnetic disk drive 28, and optical disk drive 30 couple with a hard disk drive interface 32, a magnetic disk drive interface 33, and an optical disk drive interface 34, respectively. The drives and their associated computer-readable media provide non-volatile, non-ephemeral storage of computer-readable instructions, data structures, program modules and other data for the computer 20. It should be appreciated by those skilled in the art that any type of computer-readable media which can store data that is accessible by a computer, such as magnetic cassettes, FLASH memory cards, digital video disks, Bernoulli cartridges, random-access memories (RAMs), read-only memories (ROMs), redundant arrays of independent disks (e.g., RAID storage devices) and the like, can be used in the exemplary operating environment.

A plurality of program modules that implement the optimization methods of the present invention can be stored on the hard disk, magnetic or FLASH storage device 29, optical disk 31, ROM 24, or RAM 25, including an operating system 35, one or more application programs 36, other program modules 37, and program data 38. A plug-in program containing a security transmission engine for the present invention can be resident on any one, or on a plurality of these computer-readable media.

In some embodiments, a user (e.g., the audiologist or the patient) enters commands and perception information into the computer 20 through input devices such as a keyboard 40, pointing device 42 or other suitable device such as a microphone (not shown). Other input and/or output devices (not shown) can include a microphone, joystick, game pad, satellite dish, scanner, speaker, headphones or the like. These other input and output devices are often connected to the processing unit 21 through a serial port interface 46 that is coupled to the system bus 23, but can be connected by other interfaces, such as a parallel port, game port, or a universal serial bus (USB); a monitor 47 or other type of display device can also be connected to the system bus 23 via an interface, such as a video adapter 48. The monitor 47 can display a graphical user interface for the audiologist and/or user. In addition to the monitor 47, computers typically include other peripheral output devices (not shown), such as speakers and printers.

In some embodiments, computer 20 operates in a networked environment using logical connections to one or more remote computers or servers, such as remote computer 49. These logical connections are achieved by a communication device coupled to or a part of the computer 20; the invention is not limited to a particular type of communications device. The remote computer 49 can be another computer, a server, a router, a network PC, a client, a peer device or other common network node, and typically includes many or all of the elements described above relative to the computer 20, although only memory storage device 50 and application programs 36 have been illustrated in FIG. 1. The logical connections depicted in FIG. 1 include local-area network (LAN) 51 and wide-area network (WAN) 52. Such networking environments are commonplace in office networks, enterprise-wide computer networks, intranets and the Internet, which are all types of networks.

When used in a local-area networking (LAN) environment, the computer 20 is connected to the LAN 51 through a network interface, modem or adapter 53, which is one type of communications device. When used in a wide-area networking (WAN) environment such as the internet, the computer 20 typically includes an adaptor or modem 54 (a type of communications device), or any other type of communications device, e.g., a wireless transceiver, for establishing communications over the wide area network 52, such as the internet. The modem 54, which may be internal or external, is connected to the system bus 23 via the serial port interface 46. In a networked environment, program modules depicted relative to the personal computer 20, or portions thereof, (or those stored in the externally worn device 111 or the implanted device 110) can be stored in the remote memory storage device 50 of remote computer (or server) 49 and accessed over the internet or other communications means. Note that the transitory signals on the internet may move stored program code from a non-transitory storage medium at one location to a computer that executes the code at another location by the signals on one or more networks. The program instructions and data structures obtained from a network or the internet are not "stored" on the network itself, but are stored in non-transitory storage media that may be connected to the internet from time to time for access. It is appreciated that the network connections shown are exemplary, and in some embodiments, other means of, and communications devices for, establishing a communications link between the computers may be used including hybrid fiber-coax connections, T1-T3 lines, DSL's, OC-3 and/or OC-12, TCP/IP, microwave, WAP (wireless application protocol), and all other electronic media through standard switches, routers, outlets and power lines, as the same are known and understood by one of ordinary skill in the art.

The hardware and operating environment in conjunction with which embodiments of the invention may be practiced has been described. The computer 20 in conjunction with which embodiments of the invention can be practiced can be a conventional computer, a distributed computer, or any other type of computer; the invention is not so limited. Such a computer 20 typically includes one or more processing units as its processor, and a computer-readable medium such as a memory. The computer 20 can also include a communications device such as a network adapter or a modem, so that it is able to communicatively couple to other computers, servers, or devices.

In some embodiments, one or more parts of system 100 elicits and receives input from a user, and based on the input, modifies, adjusts or executes one or more of the methods of the present invention as described herein.

Figure 2A:
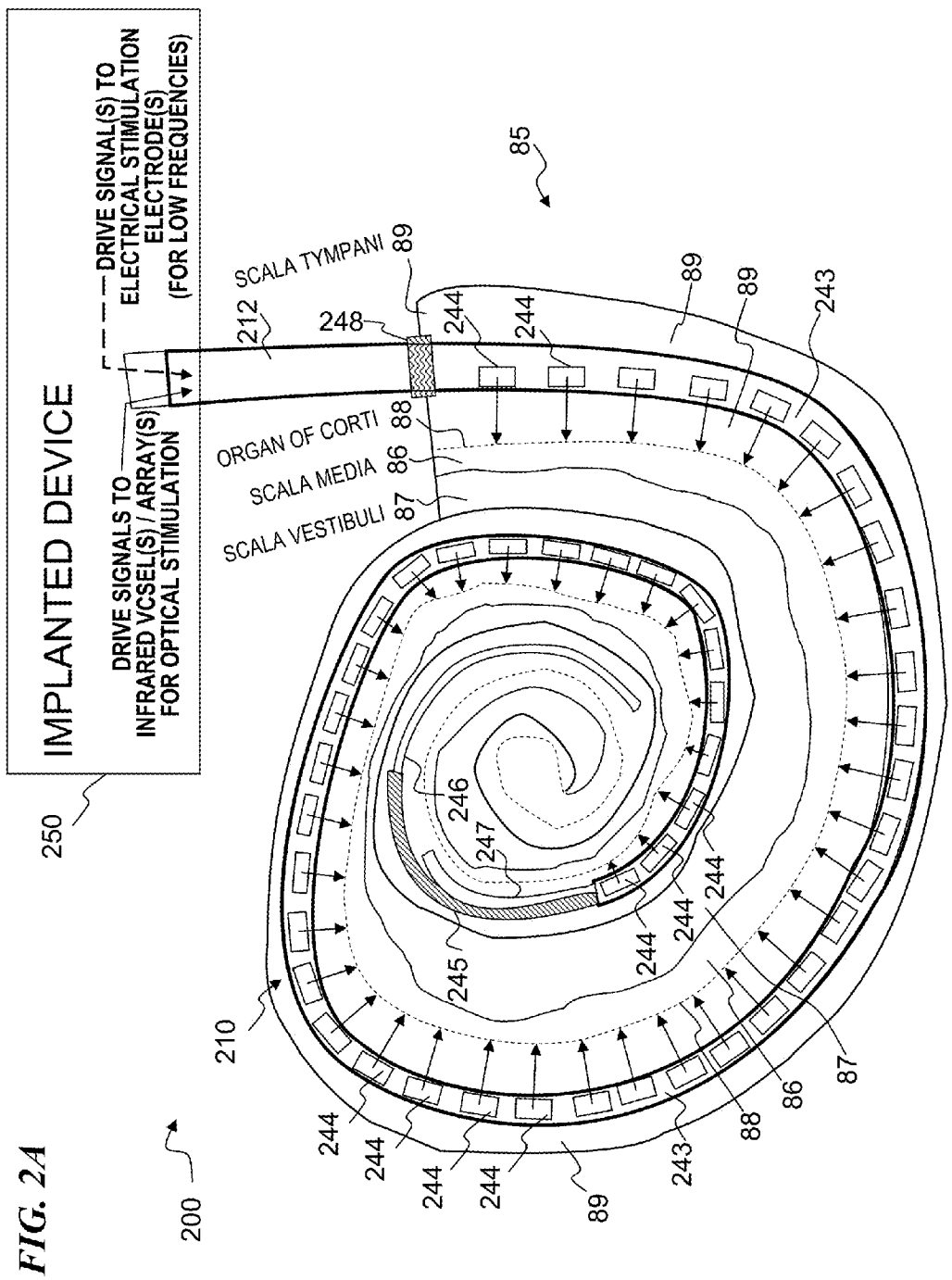
FIG. 2A is a schematic diagram illustrating an implanted cochlea-stimulation device 200.

FIG. 2A is a schematic diagram of a VCSEL-based implanted stimulation system 200 that is coiled from a base end (that is electrically connected to a driver circuit 250 via electrical connection substrate ribbon 212) to an apex end, such that the coiling of system 200 matches the coiling of cochlea 85 and is inserted into cochlea 85. In some embodiments, system 200 is configured to be inserted within a length of cochlea 85 (forming the inserted intra-cochlear portion 210), while in other embodiments, system 200 is configured to be placed outside and along the exterior of cochlea 85. In some embodiments, system 200 includes a plurality of VCSEL sources 244 configured to direct optically stimulating light pulses to excitable tissue in the cochlea of a person in order to trigger nerve action potentials in one or more auditory nerve pathways of the cochlea.

The basilar membrane within the cochlea 85 of the inner ear is a stiff structural element that separates two liquid-filled tubes (the scala media 86 and the scala tympani 89) that run along the coil of the cochlea, and that contains the organ of corti 88. A third liquid-filled tube that runs along the coil of the cochlea, the scala vestibuli 87, is separated from the scala media 86 by Reissner's membrane, and has a fluid that is different than that of the scala media 88 and the scala tympani 89. High frequencies are detected by nerves nearest the basal end (where the basilar membrane is stiffest), while low frequencies are detected by nerves nearest the apical end of the cochlea 85. Thus, when an optical-stimulation device cannot be inserted far enough towards the apical end, it is the low-frequency sensations that cannot be stimulated. Therefore, in some embodiments, the intra-cochlear portion 210 of system 200 includes one or more signal electrodes 246 (in some embodiments, the intra-cochlear portion 210 optionally includes one or more return (or ground) electrodes 247 to provide a nearby electrical ground for return current in a portion of the cochlea across from the electrodes 246, so as to provide an electrical field that extends across one or more stimulate-able nerves in the cochlea. In other embodiments, electrodes are arranged in pairs of (or groups of two or more) electrodes that are driven by bi-phasic differential electrical-stimulation signals, either of which, at different times can be more positive than the other, and the signals are generated to prevent ionic-charge build-up in the tissue located deep in the apical end of cochlea 85.

In some such embodiments, electrodes 246 are configured to provide electrical stimulation for the apical spiral ganglion cells at the lower frequency range. Electrical stimulation can access these deeper regions of cochlea 85 because of the spread of electricity that occurs during electrical stimulation (in some embodiments, there is no spreading of the optical signal to illuminate the cells beyond the tip of the last VCSEL source 244). In some embodiments, the one or more electrodes 246 are covered by an insulating sheath 245 that is configured to electrically isolate the one or more intra-cochlear electrodes 246 (and optionally 247) from each other and to help orient the electrical field between the intra-cochlear electrode(s). In some embodiments, insulating sheath 245 is further configured to electrically isolate the VCSEL sources 244 from the one or more electrodes 246/247. In some embodiments of the system 200 of FIG. 2, the electrical-stimulation portions (electrodes 246/247 and insulating sheath 245) and are omitted and only the optical-stimulation portions are implemented. In some such embodiments, instead of using electrodes 246 to stimulate the lower frequency range, one or more VCSEL sources 244 located at the far apex end of substrate 243 are directed into the apical end of cochlea 85 at angles sufficient to stimulate the lower frequency range. In some embodiments, at least the stimulation-emission end (the intra-cochlear portion 210 from which optical and electrical-stimulation signals are emitted) of the cochlear implant is implanted within, and along a length of, the scala tympani 89. In other embodiments, at least the stimulation emission end of the cochlear implant is implanted within, and along a length of, the scala vestibuli 87. In some embodiments, the controller portion is external to the cochlea, and a feed-through conduit goes through either the round window and/or the oval window (depending on where the intra-cochlear portion 210 is located) of the cochlea connecting the controller to the intra-cochlear portion 210 (inside the scala tympani 89 and/or scala vestibuli 87), wherein the feed-through conduit 248 is coated with a bio-compatible material so that the round window and/or the oval window membrane seals to the feed-through conduit 248. In other embodiments, the entire implanted system 200 is within the scala tympani 89 or the scala vestibuli 87, or even the scala media 86 of the cochlea 85.

In some embodiments, the one or more electrodes 246 at the apical end of the implant are inserted to a location that is at least 50% of the basal-to-apical length of the cochlear channel (whichever channel is used for the implant) toward the apical end of the intra-cochlear portion 210 of the implant, as measured from the basilar membrane (i.e., the electrodes are closer to the apical end than to the basal end of the cochlea). In some embodiments, the one or more electrodes 246 at the apical end of the implant are inserted to a location that is at least 75% of the basal-apical length toward the apical end of the intra-cochlear portion 210 of the implant (i.e., much closer to the apical end than to the basal end). In some embodiments, the one or more electrodes 246 at the apical end of the implant are inserted to a location that is at least 90% of the basal-apical length toward the apical end of the intra-cochlear portion 210 of the implant (i.e., substantially at the apical end).

In some embodiments, each of the VCSEL sources 244 is located on a surface of substrate 243 that faces the organ of corti from inside cochlea 85 (e.g., in some embodiments, substrate 243 extends inside the scala tympani 89 (the lower channel) in cochlea 85 from near the base to near the apex, such that each VCSEL array 244 emits light toward the organ of corti 88). In some embodiments, no portion of system 200 is inserted into the scala vestibuli channel 87 of cochlea 85. In some embodiments, each VCSEL source 244 emits infrared optical-stimulation signals.

In some embodiments, each VCSEL array 244 has a plurality of emitters that emit light for one or more sensory frequency channels (each sensory frequency channel being the nerve pathway from hair cells located to respond to a particular audio frequency and to initial NAPs in one of the auditory nerve pathways associated with that frequency). In some embodiments, two rows of five VCSEL emitters extend across a width of each VCSEL array 244, while in other embodiments, other numbers of rows and other numbers of VCSEL emitters per row are provided. In some embodiments, via testing and mapping after implantation, one or more of the VCSEL emitters in one row is mapped and used to stimulate NAPs for one sensory frequency channel, while one or more of the VCSEL emitters in another row is mapped and used to stimulate NAPs for another sensory frequency channel. In some embodiments, multiple VCSELs are provided in each row (e.g., in some embodiments, many more than end up actually being used) in order that, to accommodate placement errors, testing of all or most of the stimulation sources, and then mapping of which stimulation causes each of a plurality of sensory responses or perceptions so that only the subset of stimulation sources that are most effective in causing a response are used to generate NAPs based on the information content of the audio signal. In some embodiments, VCSEL arrays that emit a plurality of different wavelengths are used to customize the spatial absorption profile of the stimulation light.

In some embodiments, each VCSEL source 244 includes a single VCSEL, while in other embodiments, each VCSEL source 244 includes a plurality of individually activatable lasers oriented to emit light along substantially parallel axes with somewhat overlapping spots of illumination (such that, in some embodiments, one or more of the group of VCSELs can be individually activated at a succession of different times after implantation, in order to dynamically determine which of the plurality of VCSELs in a single array 244 is best suited to stimulate one or more nerves that are very near to one another, but for which it is desired to selectively stimulate one or more individually without stimulating the adjacent neighboring nerves). In other embodiments, each group of VCSELs 244 is configured to emit laser-light beams in a plurality of non-parallel directions to stimulate nerves that are not right next to one another. In some embodiments, each group of VCSELs 244 has an associated one or more focussing devices to focus the light (e.g., graded-index-fiber (GRIN) lenses, diffraction gratings or holographs, or other suitable microlenses that either disperse the light, in some embodiments, or in other embodiments focus the light to a small spot of excitable tissue such as hair cells in cochlea 85 or spiral ganglion cells (SGCs)), while in other embodiments, no lenses are used. In some embodiments, a plurality of channels (e.g., two to a hundred or more channels) each has one or more VCSELs (e.g., in some embodiments, 1 to 5 to more VCSELs per channel), such that one or more of the VCSELs on a given channel can be selectively activated to stimulate nerves associated with that channel. In some embodiments, a plurality of VCSELs are each activated to trigger NAPs in additional neighboring spiral ganglion cells, and/or to increase the pulse-repetition rate of NAPs in a particular set of nerve pathways in order to provide loudness control, as mentioned earlier. In some embodiments, each VCSEL is connected to two electrical conductors (namely, its individual signal conductor and a common or ground conductor that is shared with other VCSEL emitters). In some embodiments, an array of VCSELs is arranged such that all VCSELs in any one row share an anode connection and all VCSELs in any one column share a cathode connection, and such that each VCSEL emitter is uniquely addressed by electrically driving its row anode and its column cathode (of course, the terms row and column can be interchanged).

In some embodiments, the implanted device of the present invention includes a sound sensor (microphone; not shown) that, upon activation by an external sound (pressure wave), generates one or more electrical signals. In some embodiments, a computerized sound analyzer decomposes the audio signal (e.g., using a fast Fourier transform (FFT), discrete cosine transform (DCT), or other suitable digital signal processor (DSP) or analog means) to output time-varying frequency components. In some embodiments, the optical-stimulation signals from VCSEL arrays 244 and electrical-stimulation signals are generated based on the outputted time-varying frequency components signals.

FIG. 2B is a perspective view of VCSEL-based stimulation system 200 showing a cut-away view of cochlea 85. In some embodiments, system 200 includes a plurality of VCSEL sources 244 configured to direct optically stimulating light pulses to excitable tissue in the cochlea of a person in order to trigger nerve action potentials in the auditory nerve 91 of the person. In some embodiments, system 200 includes a first electrode 246A and a second electrode 246B located deep in the apical end of cochlea 85. In some such embodiments, electrodes 246A and 246B are electrically isolated from each other by insulating sheaths 245. In some embodiments, system 200 is configured to optically stimulate auditory nerve 91 by directing a plurality of pulsed light signals at one or more locations on the organ of corti 88. In other embodiments, system 200 is configured to optically stimulate auditory nerve 91 by directing a plurality of pulsed light signals at one or more nerves 98 that are located in the pathway between the organ of corti 88 and the auditory nerve 91. For example, in some embodiments, VCSEL source 244A directs a pulsed laser beam 84A at a first location of one or more nerves 98 and VCSEL source 244B directs a pulsed laser beam 84B at a second location of one or more nerves 98.

FIG. 2C is a schematic perspective exploded-view diagram illustrating light-emitting, light-focussing, and/or light-pointing device 205, used to implement some embodiments of VCSEL emitters 244 of FIG. 2B. In some embodiments, each device 205 includes a semiconductor chip 252 having plurality of VCSELs 251 arranged in an array (e.g., in some embodiments, a Cartesian grid, while in other embodiments, any other suitable pattern) that allows a large number of VCSELs to be implanted such that each directs its light to a slightly different location, and such that a much smaller number of the VCSELs is activated at any one time (e.g., in some embodiments, some VCSELs may never be activated except during testing, calibration and customization, while others may be used more or less frequently depending on whether their neighboring VCSELs are activated to emit stimulation light or have recently been activated). In some embodiments, an array or other structure of focussing elements 254 (e.g., microlenses, holographs, GRIN lenses or the like) and/or angle-pointing elements 256 (e.g., a plurality of prisms (as shown in FIG. 2C), gratings, MEMS mirrors, or the like) are provided to focus, and/or point the stimulation light in various angular directions, towards the nerves to be stimulated. In some embodiments, a plurality of such light-emitting devices 205 is used as the light-source elements 244 of FIG. 2A and FIG. 2B affixed along the length of ribbon 212. In some such embodiments, ribbon 212 includes a plurality of electrical connections arranged to multiplex signals to independently activate selected ones of the VCSELs, and optionally includes a high-thermal-conductivity material configured to remove excess device heat from within the cochlea. In some embodiments, ribbon 212 further includes one or more thermal sensors (e.g., in some embodiments, implemented on the light-emitting device 205, while in other embodiments, implemented on separate devices also located along ribbon 212) that transmit temperature-indicating signals from the cochlea to controller 250.

FIG. 3M includes a schematic graph 300 of the tissue absorption 302 (which is one indication of the sensitivity to stimulation light) of a tissue at various wavelengths in a given range, and a superimposed graph 301 of a power-source spectrum having different amounts of power at each of a plurality of wavelengths, which has been customized to provide a desired spatial heating profile due to absorption of infrared light having the various wavelengths. In some embodiments of the present invention as shown in any of the figures herein, the range of wavelengths in the power-source spectrum is at least 2.5 nm. In some embodiments, the range of wavelengths in the power-source spectrum is at least 5 nm. In some embodiments, the range of wavelengths in the power-source spectrum is between about 5 nm and about 10 nm. In some embodiments, the range of wavelengths in the power-source spectrum is between about 10 nm and about 15 nm. In some embodiments, the range of wavelengths in the power-source spectrum is between about 15 nm and about least 20 nm. In some embodiments, the range of wavelengths in the power-source spectrum is between about 20 nm and about 30 nm. In some embodiments, the range of wavelengths in the power-source spectrum is between about 30 nm and about 40 nm. In some embodiments, the range of wavelengths in the power-source spectrum is more than 40 nm.

In some embodiments, the wavelengths of the optical power source are in the range of about 800-900 nm. In some embodiments, the wavelengths of the optical power source are in the range of about 900-1000 nm. In some embodiments, the wavelengths of the optical power source are in the range of about 1000-1100 nm. In some embodiments, the wavelengths of the optical power source are in the range of about 1100-1200 nm. In some embodiments, the wavelengths of the optical power source are in the range of about 1200-1300 nm. In some embodiments, the wavelengths of the optical power source are in the range of about 1300-1400 nm. In some embodiments, the wavelengths of the optical power source are in the range of about 1400-1500 nm. In some embodiments, the wavelengths of the optical power source are in the range of about 1500-1600 nm. In some embodiments, the wavelengths of the optical power source are in the range of about 1600-1700 nm. In some embodiments, the wavelengths of the optical power source are in the range of about 1700-1800 nm. In some embodiments, the wavelengths of the optical power source are in the range of about 1800-1900 nm (in some embodiments, this is a more preferred range). In some embodiments, the wavelengths of the optical power source are in the range of about 1900-2000 nm. In some embodiments, the wavelengths of the optical power source are in the range of about 2000-2100 nm. In other embodiments, the wavelengths of the optical power source extend across (include two or more different wavelengths within (i.e., two or more spectrally separated wavelengths within)) one or more of these ranges.

Figure 3G:
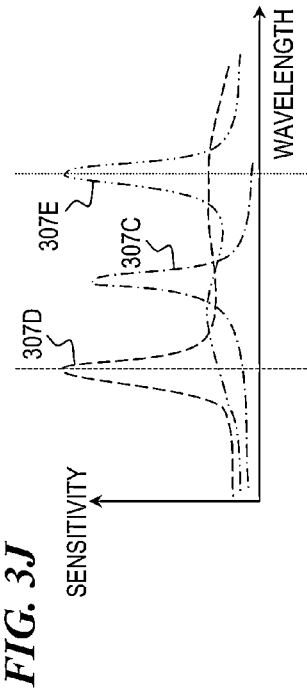
FIG. 3G is a schematic graph 307B of a tissue sensitivity to optical stimulation for a second given type or composition of tissue as a function of the wavelength of the optical stimulation.

In some embodiments, within the selected range of stimulation wavelengths, the tissue-absorption value increases as the wavelength increases (as shown by graph 302 of FIG. 3M and graph 307A of FIG. 3B) and the optical-stimulation power at each of a plurality of wavelengths decreases as the wavelength increases (as shown by graph 301 of FIG. 3M, graph 308A of FIG. 3D, and graph 309A of FIG. 3F). In other embodiments, within the selected range of stimulation wavelengths, the tissue-absorption value decreases as the wavelength increases (as shown by graph 307B of FIG. 3G and graphs 307D and 307C of FIG. 3J) and the optical-stimulation power at each of a plurality of wavelengths increases as the wavelength increases (as shown by graph 308B of FIG. 3H and graph 309B of FIG. 3I).

Figure 3H:
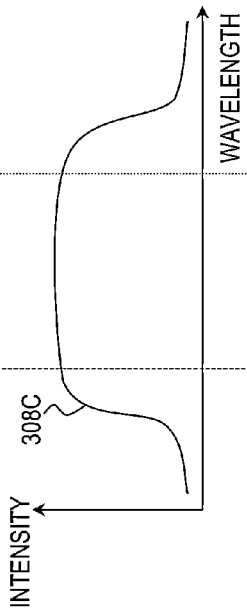
FIG. 3H is a schematic graph 308B of a designed power/wavelength spectrum profile used to customize the absorption of optical power in the tissue.

FIG. 3A is a conceptual schematic diagram of a broadband wavelength source 310 having a designed power/wavelength spectrum profile formed to customize the absorption of optical power in the tissue of interest. In some embodiments, broadband wavelength source 310 includes a laser having a reflective grating or other means for generating different amounts of light output at various wavelengths (such as shown in FIG. 3D described below). Source 310 is controlled by an electrical signal 317 to emit pulsed light 318 having a spectrum such as shown in FIG. 3D, FIG. 3H, or FIG. 3K, as desired by the designer. In some embodiments, the wavelength range (e.g., full-width half-maximum (FWHM) range of wavelengths) of the optical-source power spectrum is at least 2.5 nm. In some embodiments, the range of wavelengths in the optical-source power spectrum is at least 5 nm. In some embodiments, the range of wavelengths in the optical-source power spectrum is between about 5 nm and about 10 nm. In some embodiments, the range of wavelengths in the optical-source power spectrum is at least about 10 nm wide and less than about 100 nm (in some embodiments, this is a preferred range). In some embodiments, the range of wavelengths in the optical-source power spectrum is between about 10 nm and about 15 nm. In some embodiments, the range of wavelengths in the optical-source power spectrum is between about 15 nm and about least 20 nm. In some embodiments, the range of wavelengths in the optical-source power spectrum is between about 20 nm and about 30 nm. In some embodiments, the range of wavelengths in the optical-source power spectrum is between about 30 nm and about 40 nm. In some embodiments, the range of wavelengths in the optical-source power spectrum is more than 40 nm. In some embodiments, the optical-stimulation signal includes two or more different wavelengths within (i.e., two or more spectrally separated wavelengths within) one or more of these ranges.

FIG. 3B includes a schematic graph 307A of a tissue sensitivity to optical stimulation for a first given type or composition of tissue as a function of the wavelength of the optical stimulation. In some embodiments, graph 307A is representative of light absorption at various wavelengths. Note that in some wavelength ranges the sensitivity will increase at longer wavelengths such as shown in FIG. 3B, while in other embodiments, the sensitivity will decrease at longer wavelengths such as shown in FIG. 3G, while in still other embodiments, the sensitivity peak at different wavelengths for different tissue types, such as shown in FIG. 3J, as described below.

FIG. 3C is a schematic diagram of a broadband wavelength source 320 having a designed power/wavelength spectrum profile formed to customize the absorption of optical power in the tissue of interest. In some embodiments, source 320 includes a conventional broadband source 321 having a broad Gaussian linewidth (e.g., a laser (such as a vertical-cavity surface-emitting laser (VCSEL) or optically-pumped fiber laser) or superluminescent light-emitting diode or filtered amplified spontaneous emission (ASE) fiber source) which is controlled by electrical signal 327 to emit pulsed light 322. The pulsed light passes through a shaped-spectrum filter 323 such that output of the broadband wavelength source 320 emits pulsed light 328 having a spectrum such as shown in FIG. 3D, FIG. 3H, or FIG. 3K, as desired by the designer.

FIG. 3D is a schematic graph 308A of a designed power/wavelength spectrum profile used to customize the absorption of optical power in the tissue.

FIG. 3E is a schematic diagram of a broadband wavelength source 330 having a designed power/wavelength spectrum profile formed to customize the absorption of optical power in a tissue of interest. In some embodiments, the power spectrum is designed to compensate for the shape of the tissue absorption characteristics (such as shown in FIG. 3B), in order to obtain the desired heat profile (such as shown in FIG. 4D (showing activation of NAPs substantially equally at different depths) or as shown in FIG. 4E (showing activation of NAPs differently at different depths)). In some embodiments, a plurality of narrow-band lasers 331 are controlled by a plurality of independent electrical signals 337.1, 337.2, . . . 337.N, such that the power at each laser wavelength can be varied, and when the outputs of the individual lasers are combined with a beam combiner 334, the broadband wavelength source 330 has an output beam 339 having a spectrum such as shown in FIG. 3F, or as desired by the designer. In some embodiments, the plurality of narrow-band lasers 331 are controlled by a plurality of independent electrical signals 337.1, 337.2, . . . 337.N, such that the power at each laser wavelength can be varied over time with different waveshapes and/or pulses at different times, resulting in spectra that vary over time such as shown in FIGS. 4F, 4G, and 4H described below.

FIG. 3F is a schematic graph 309A of a designed power/wavelength spectrum profile used to customize the absorption of optical power in a tissue. In some embodiments, the power/wavelength spectrum profile of graph 309A is obtained by combining a plurality of light signals from a plurality of narrow-band lasers 331.

FIG. 3G is a schematic graph 307B of a tissue sensitivity to optical stimulation for a second given type or composition of tissue as a function of the wavelength of the optical stimulation. In contrast to the chosen tissue type and wavelength range shown in FIG. 3B above, this tissue type has decreased sensitivity (e.g., due to decreased absorption) at longer wavelengths.

FIG. 3H is a schematic graph 308B of a designed power/wavelength spectrum profile used to customize the absorption of optical power in the tissue having the sensitivity of the graph 307B of FIG. 3G.

Figure 3I:
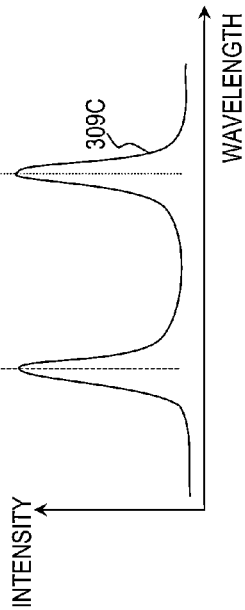
FIG. 3I is a schematic graph 309B of a designed power/wavelength spectrum profile used to customize the absorption of optical power in the tissue.
Figure 3J:
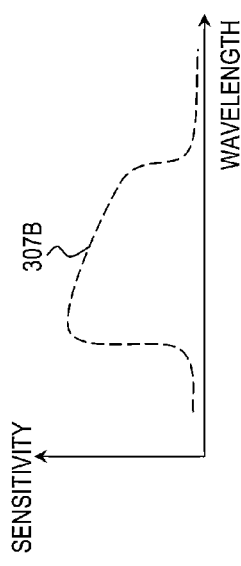
FIG. 3J includes schematic graphs 307C, 307D, and 307E of tissue sensitivity to optical stimulation for a three types or compositions of tissue as a function of the wavelength of the optical stimulation.
Figure 3K:
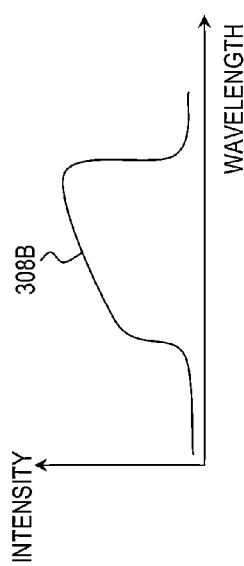
FIG. 3K is a schematic graph 308C of a designed power/wavelength spectrum profile used to customize the absorption of optical power in a plurality of tissues.

FIG. 3I is a schematic graph 309B of a designed power/wavelength spectrum profile used to customize the absorption of optical power in a tissue. In some embodiments, the power/wavelength spectrum profile of graph 309B is obtained by a device such as shown in FIG. 3E described above.

FIG. 3J includes schematic graphs 307C, 307D, and 307E of tissue sensitivity to optical stimulation for three types or compositions of tissue as a function of the wavelength of the optical stimulation. For a group of such tissue types, it is sometimes desirable to have some of the tissues (e.g., those of graphs 307D and 307E) absorb the stimulation light and be heated enough to trigger NAPs, while having some others of the tissues (e.g., those of graph 307C) not absorb enough energy to trigger NAPs.

FIG. 3K is a schematic graph 308C of a designed power/wavelength spectrum profile used to customize the absorption of optical power in a plurality of tissues. Such a broad spectrum is useful in cases when it is desired to trigger NAPs in all the tissue types of the graphs of FIG. 3J.

Figure 3L:
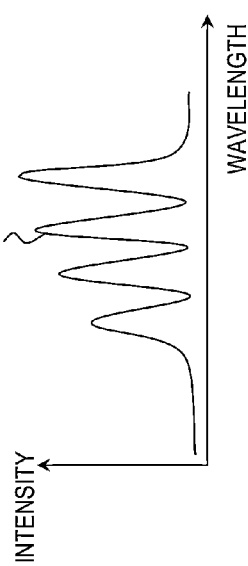
FIG. 3L is a schematic graph 309C of a designed power/wavelength spectrum profile used to customize the absorption of optical power in a plurality of tissues.

FIG. 3L is a schematic graph 309C of a designed power/wavelength spectrum profile used to customize the absorption of optical power in a plurality of tissues. Such a selectively activated spectrum is useful in cases when it is desired to trigger NAPs in some of the tissues (e.g., those of graphs 307D and 307E of FIG. 3J), while having some others of the tissues (e.g., those of graph 307C) not absorb enough energy to trigger NAPs.

FIG. 4 is a plot 400 of a temperature profile of tissue due to absorption of infrared light from a single-wavelength source. In this plot, the tissue vertically in the center and horizontally at the left (in an innermost ring) is heated to (e.g., in this example) to 42° C. (42 degrees centigrade), which in some embodiments, is sufficient to trigger a NAP if a nerve were located at that position. The tissue to the right of a tissue depth of 2 mm remains at 37.5° C. (normal body temperature), while intermediate tissue is heated, but not enough to trigger NAPs even if nerves were located there.

FIG. 4A is a schematic diagram that includes a hypothetical plot 440 of a temperature profile of tissue due to absorption of light from single-wavelength source 331 of infrared light having a first wavelength. The oval lines represent equi-temperature locations, with line 446 representing the tissue area having the highest temperature (this would be the temperature needed to trigger NAPs in nerves, since the controller will strive to prevent stimulation signals that result in higher temperature, since those are not more effective at triggering NAPs and are likely to damage tissue). Each of the other equi-temperature lines (lines 445, 444, 443, 442 and 441) represent successively lower temperatures, each of which is too low to trigger NAPs. Of the nerves 81, 82, and 83 in the tissue 80, only the nerve 81 is located within the 446 line, and so it, but not the others, will have a NAP triggered.

FIG. 4B is a schematic diagram that includes a plot 440 of a temperature profile of tissue due to absorption of single-wavelength source 332 of infrared light having a second wavelength. Again, the oval lines represent equi-temperature locations, with line 446 representing the tissue area having the temperature needed to trigger NAPs in nerves. Of the nerves 81, 82, and 83 in the tissue 80, only the nerve 82 is located within this 446 line, and so it, but not the others, will have a NAP triggered.

FIG. 4C is a schematic diagram that includes a plot 440 of a temperature profile of tissue due to absorption of single-wavelength source 333 of infrared light having a third wavelength. Again, the oval lines represent equi-temperature locations, with line 446 representing the tissue area having the temperature needed to trigger NAPs in nerves. Of the nerves 81, 82, and 83 in the tissue 80, only the nerve 83 is located within this 446 line, and so it, but not the others, will have a NAP triggered. In some embodiments, the threshold optical-stimulation signal extends across two of the three cases shown in FIG. 4A, FIG. 4B or FIG. 4C.

FIG. 4D is a schematic diagram that includes a plot 440 of a temperature profile of tissue due to absorption of source 330A of infrared light having a customized spectrum of wavelengths (e.g., the spectrum of FIG. 3D, 3F, or 3K). Note that line 446 representing the tissue area having the temperature needed to trigger NAPs in nerves is larger than previous cases of FIG. 4A, FIG. 4B or FIG. 4C (extending from shallow to deep), and now covers all three of the nerves 81, 82, and 83 in the tissue 80, so all the nerves 81, 82, and 83, each at a different depth, have a NAP triggered.

FIG. 4E is a schematic diagram that includes a plot 440 of a temperature profile of tissue due to absorption of infrared light from source 330B having a customized spectrum of wavelengths (e.g., the spectrum of FIG. 3L). Note that line 446 of FIG. 4D representing the tissue area having the temperature needed to trigger NAPs in nerves is now split into two parts (both of which trigger a NAP), 446S which covers the shallow nerve 81, and 446D which covers deep nerve 83, but this threshold region does not cover middle nerve 82 in the tissue 80, so the moderate-depth nerve 82 will not have a NAP triggered. In some embodiments, wavelengths of the spectrum are chosen such that part (some of the wavelength(s)) of the stimulation optical signal are absorbed at a shallow depth (to provide the triggering temperature labeled 446S) and part (others of the wavelength(s)) of the stimulation optical signal is absorbed at a deep depth (to provide the triggering temperature labeled 446D).

FIG. 4F is a schematic graph 409A of a designed power/wavelength spectrum profile for a time period N in a sequence of time periods N, N+1, N+2 used to customize the temporal absorption of optical power in a plurality of tissues.

FIG. 4G is a schematic graph 409B of a designed power/wavelength spectrum profile for a time period N+1 in a sequence of time periods N, N+1, N+2 used to customize the temporal absorption of optical power in a plurality of tissues.

FIG. 4H is a schematic graph 409C of a designed power/wavelength spectrum profile for a time period N+2 in a sequence of time periods N, N+1, N+2 used to customize the temporal absorption of optical power in a plurality of tissues. The time-varying sequence of different power spectra is used, in some embodiments, to customize the triggering of NAPs.

Figure 5:
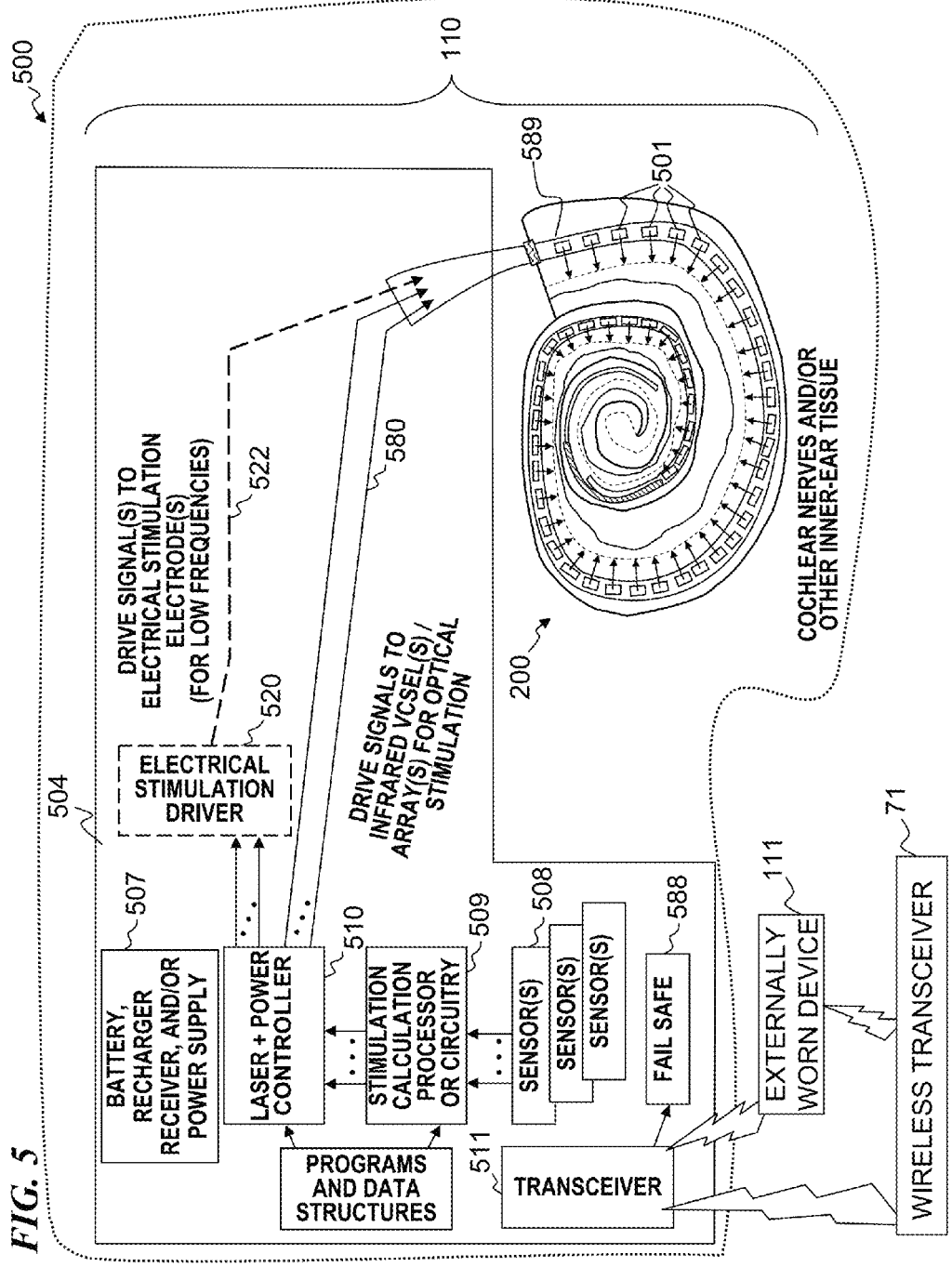
FIG. 5 is a schematic representation of a system 500 having an implanted device 110, an optional externally worn device 111 and a transceiver 71 of customization console computer such as shown in FIG. 1.

FIG. 5 is a block diagram of an implantable/partially implantable system 500 that uses a VCSEL array for light stimulation of the auditory nerve of a person. System 500 represents one embodiment of the present invention, wherein a low-power, low-threshold VCSEL array 501 (e.g., a plurality of VCSEL sources such as found in system 200 shown in FIG. 2A and FIG. 2B, and device 205 of FIG. 2C) emits laser light from each of a plurality of VCSELs, for example VCSELs implemented as an array of separately activatable lasers formed in a monolithic semiconductor chip. In some embodiments, each laser beam is separately controlled by laser-and-power controller 510 that drives the laser-diode VCSELs under control of a processor or circuitry 509 that generates signals that are configured to stimulate the tissue in response to input audio signals as desired. In some embodiments, the drive signals are transmitted to VCSEL array 501 via electrical connection 580. In some embodiments, system 500 includes wireless transceiver 71 (e.g., from a system console 100 such as shown in FIG. 1) that allows wireless control and customization programming of system 500 (via transceiver 511) and/or an externally worn device 111. In some embodiments, externally worn device 111 includes one or more microphones or similar sound sensors, audio-processing circuitry, and a wireless transmitter to send the processed audio signals to transceiver 511 in the intra-cochlear portion of 200 shown in FIG. 5. In some such embodiments, externally worn device 111 includes one or more rechargeable batteries (which may be recharged overnight in a recharging station while the patient sleeps) and a wireless power transducer to send electrical power to device 500. In other embodiments, implant 500 includes one or more microphones or similar sound sensors in the set of sensors 508 such that the implant is self contained (in some such embodiments, implant 500 itself includes one or more rechargeable batteries 507 that may be recharged overnight by a nearby wireless recharging station (which, in some embodiments, is included in wireless transceiver 71) while the patient sleeps.

In some embodiments, the set of sensors 508 includes one or more temperature sensors, located in and/or along the in-body portion 589 implanted within the cochlea, and configured to provide feedback to system 500 in order to provide a safety shutdown and/or optimize the optical stimulation provided by system 500. In some embodiments, at least one temperature sensor in the set of sensors 508 is implemented in each of a plurality of VCSEL-array chips 501 to allow temperature monitoring throughout the cochlea.

In some embodiments, long-wavelength VCSEL devices (e.g., VCSELs having wavelengths in the range of 1.6 to 2 microns) and/or VCSEL arrays, such as described in U.S. Pat. No. 7,031,363 to Biard and U.S. Pat. No. 7,004,645 to Lemoff (which are each incorporated herein by reference), are used for each of a plurality of VCSEL arrays 501.

With VCSEL emitters as small as about ten (10) microns (or smaller) in diameter per channel, in some embodiments, a single VCSEL chip or assembly is used to output multiple independent stimulation channels (VCSEL laser signals) in any suitable array permutation or shape, and in some embodiments, these channels are fiber coupled, lens coupled, and/or direct light straight to a plurality of areas of tissue. In some embodiments, a combination of both fiber-coupled and direct propagation laser output is used to stimulate tissue. In some embodiments, the VCSELS are located in device 504 outside the cochlea and optical fibers are used to fiber-couple the light to the various areas inside the cochlea.

In some embodiments, implantable/partially implantable system 500 includes an electrical-stimulation driver 520 to drive electrodes contained within the implantable part of the system, 200. The drive signals are transmitted to the electrodes via electrical connection 522. In some embodiments, these electrodes stimulate auditory nerves in the person to improve low-frequency hearing response.

FIG. 6A is a flowchart of a method 601, according to some embodiments of the present invention, where the method is performed by a programmed information processor using stored instructions on non-transitory computer readable medium 690. The method 601 employs, depending on the embodiment of the invention, a plurality of collections of externally provided data stored in computer-readable data structures. In some embodiments, data includes patient-specific audio information, or auditory profile 685. In some embodiments, data includes general rules for mapping sounds from the environment onto auditory-nerve stimulators 684. In some embodiments, the data includes anti-tissue-damage rules 682, which, in some embodiments, includes rules based on tissue heating. In some embodiments, data includes anti-device-damage rules 681, which, in some embodiments, includes rules based on tissue heating. In some embodiments, data includes pulse shaping rules 683.

In some embodiments, audio sensors, which include one or more microphones 610, detect sounds in the environment around a patient (a person) wearing the implantable or partially implantable auditory-nerve-stimulation system (cochlear implant). Signals are sent to an audio processor where real-time audio data is extracted from the signals (function 612). In some embodiments, input signal audio data is organized into frames, where a given frame contains information about the input signal at a given point in time. In some embodiments, this necessary information includes the audio spectrum of the input signal. In some embodiments, an auditory channel map is produced (function 620). In some embodiments, general auditory mapping rules 684 and/or a patient specific auditory profile 685 are used to produce the auditory channel map. The auditory channel map is stored into computer-readable data structures 621. In some embodiments, auditory channels are organized into a plurality of bins, where each bin is a set of frequency-adjacent auditory channels. The data extracted from the input signal is processed into channels (function 622), using the stored auditory channel map 621, by determining the loudness (signal strength) of the portion of the input signal that corresponds to each channel. This channel information is stored (function 624) for each channel in computer-readable data structures 686. In some embodiments, the information stored in the computer readable data structures 686 includes historic channel information, that is, the audio information from some number of previous points in time. In some embodiments, where the input audio signal is organized into frames, channel information is stored for a designer-determined number of frames, for each of a plurality of frequencies or frequency bands. The time-based (historic) channel information provides the operational data needed to restrict the operation of specific light emitters to limit potential nerve damage in the cochlea, or light-emitter (e.g., VCSEL) damage (e.g., damage that might occur due to accumulated heat from too many pulses to one area of the cochlea within a given amount of time (e.g., in some embodiments, the most recent one-second time period, for example) as re-measured on an on-going basis; or too many pulses from one VCSEL emitter in such a period of time). An example of a graph of one frame of information is shown in 687. In some embodiments, if the accumulated light signal from a particular received audio frequency would cause too much heat in one area of the cochlea or one VCSEL, the pulse rate to that one area of the cochlea or one VCSEL is reduced relative to normal pulse rate for a particular loudness in the received audio frequency band. In some such embodiments, the pulses of a frequency that is one octave above or below the received audio frequency band are increased to provide a substitute that can be perceived or understood by the patient to convey similar information as would have been conveyed by pulses at the normal rate for the cochlear area normally stimulated by the received audio frequency-band signal. In other words, if one particular received audio frequency band receives too much signal in a given time period, the cochlear stimulation for that frequency is reduced and/or the stimulation is instead applied to one or more other cochlear regions that is/are an integer number of octaves away from the cochlear region normally stimulated for that received audio frequency or frequency band.

The channel information is processed (function 630) to generate drive control signals for the VCSELs. The VCSELs are driven (function 695) such that the optical signals emitted from the VCSELs stimulate auditory nerves in the person wearing the cochlear implant so that the person perceives the audio signal detected by the microphones (or other audio-sensing devices). Light (the optical signal) emitted by a given VCSEL stimulates a specific auditory nerve or nerves. Each specific auditory nerve corresponds to a particular sound frequency, and the triggering of that auditory nerve results in the person perceiving sound of that corresponding frequency. In some embodiments, the output of the VCSELs is pulsed. In some embodiments, the intensity of the optical signal emitted from the VCSELs is varied in order to produce the perception of differing loudness levels. In other embodiments, the VCSELs are pulsed at varying rates such that the person perceives differing loudness levels.

In some embodiments, additional information is used in the processing step 630 which can include, but is not limited to, heat-based VCSEL-anti-device damage rules 681, heat-based tissue-anti-damage rules 682, pulse-shaping rules 683, history of recent audio signals 686, and nerve response feedback information 619. Heat-based VCSEL-anti-device damage rules 681 may be used to limit how long, at what power level, and how frequently a specific VCSEL is operated, in order to prevent damage to the VCSEL from overheating. Heat-based tissue-anti-damage rules 682 may be used to limit how long, at what power level, and how frequently a specific auditory nerve and/or surrounding tissue is illuminated, in order to prevent damage to the nerve and tissue from overheating. In some embodiments, where the channels are organized into bins, the tissue-anti-damage rules and the VCSEL-anti-device damage rules are applied within each bin (set of adjacent frequency channels). In some embodiments, the rules can include limits as to the number of VCSELs operated in a given bin at a single point in time or within a window of time.

In some embodiments, the optical signal 696 emitted from the VCSELs is transmitted (function 697) to the auditory nerves, stimulating the nerves by triggering NAPs in the nerves (function 698). In some embodiments, optical detectors sense the nerve response (function 618), and the nerve responses are processed (function 619) to determine how the person's auditory nerves responded to the optical-stimulation signals. In some embodiments, the response information is fed back to the channel-information-processing function 630, where this response information is used to improve the channel processing and the driving of the VCSELs in order to improve the sound perceived by the person wearing the cochlear implant.

In some embodiments, the programmed information-processor-stored instructions and the various computer-readable data structures used by the instructions, which are described above, are received (via function 691 of FIG. 6A) from an external reprogramming device, allowing the operation of the cochlear implant to be altered after the auditory-nerve-stimulation system has been implanted in a person.

Referring again to FIG. 6A, in some embodiments of method 601, at block 610 an audio signal is obtained from one or more microphones configured to obtain signals representing sounds and pressure variations in the environment surrounding the patient, and to generate electrical signals that are processed by process 612 to obtain real-time data representing each of a plurality of audio-frequency channels, each audio-frequency channel signal having a value based on the sounds within a limited band of audio frequencies for the current time frame (or processing cycle). In some embodiments, the loudness values for the various audio-frequency channels are processed by process 622 to select which audio-frequency channels will be activated within each of a plurality of bins of audio-frequency channels, and a history of such values is stored by process 624 into data structure 686 (schematically shown in the adjacent graph 687 of audio-frequency channel values, wherein graph 687 shows power of each audio-frequency channel on the vertical axis and center frequency of each audio-frequency channel on the horizontal axis). In some embodiments, experimental rules for auditory stimulation are derived and a storage-medium having a general-rule computer-readable data structure (CRDS) 684 contains general rules for mapping audio input to auditory stimulation based on physiological considerations. In addition, some embodiments include a patient-specific CRDS 685 that modifies or supplements the general-rule CRDS 684. In some embodiments, patient-specific CRDS 685 is derived by empirically outputting a set of audio output signals to the implanted system and eliciting and receiving feedback from the patient indicative of the sensations perceived as a result of the optical and/or electrical stimulation applied. In some embodiments, operation 620, based on general-rule CRDS 684 and patient-specific CRDS 685, derives a map of auditory input (e.g., frequencies)-to-stimulation site(s) based on empirical testing and stores the resulting map into map CRDS 621. In some embodiments, for each successive time frame, operation 622 combines the audio-frequency channel-loudness-signal values from audio-processing operation 612 and the mapping rules from CRDS 621 into audio-frequency channel-stimulation values. In some embodiments, operation 624 stores into CRDS 686 a history of the audio-frequency channel and/or bin values for most-recent P frames. Operation 630 then takes the audio-frequency channel information for the current time frame (and optionally from a predetermined number of prior time frames) and, using the heat-based anti-tissue-damage-rules CRDS 682 (which limit the number of audio-frequency channels that are allowed to be activated in any one time frame and/or within P successive time frames), along with data from VCSEL heat-based anti-device-damage-rules CRDS 681 and rules for stimulation pulse shapes (pulse width and/or rise/fall shape) in CRDS 683, operation 630 generates pulse parameters for the stimulation light for each VCSEL to be activated. Operation 695 takes the pulse parameters from operation 630 and drives the VCSELs to emit stimulation signals (a set of infrared optical-stimulation signal pulses and optionally one or more electrical stimulation pulses) which are transmitted (function 697) to the tissue to trigger CNAPs. In some embodiments, the resulting physiological response is a set of CNAPs 698 that is transmitted to the brain of the patient, and operation 618 optionally measures the nerve response and operation 619 processes a feedback signal that is fed back into operation 630. In some embodiments, a reloadable computer-readable storage medium 690 holds instructions and data structures (in some embodiments, received (e.g., by a wireless receiver) 691 from an external device) that control the operations described above.

Figure 6B:
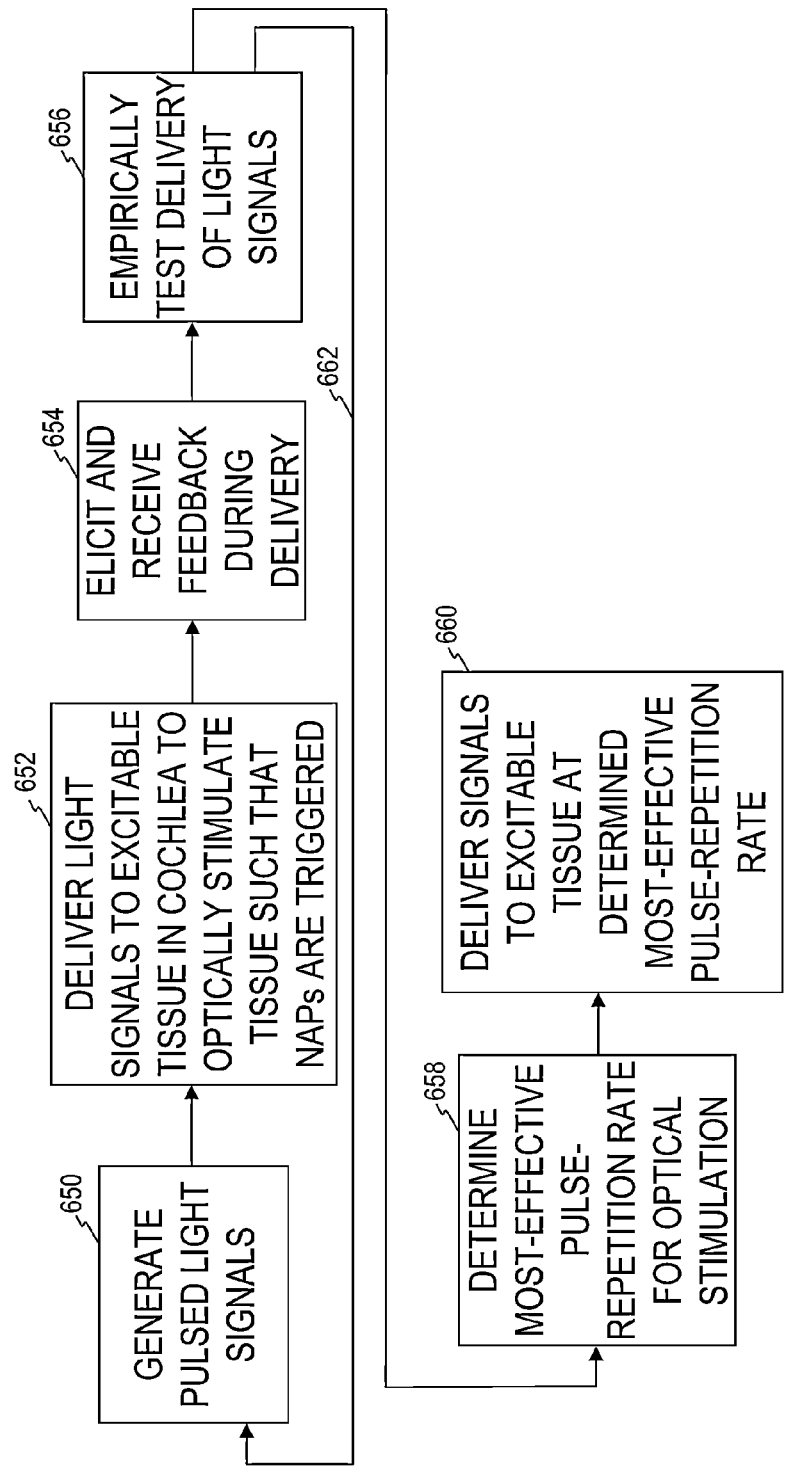
FIG. 6B is a flow chart of a method 602, according to some embodiments of the present invention.

FIG. 6B is a flow chart of a method 602, according to some embodiments of the present invention, for optimizing the pulse-repetition rate used during optical stimulation of the cochlea. In some embodiments, pulsed light signals are generated at block 650, the generated light signals are delivered to excitable tissue in a cochlea of a person to optically stimulate the tissue such that NAPs are triggered at block 652, feedback is elicited and received during (or shortly after) the delivery of the signals at block 654, the delivery of the signals is empirically tested (to try to find the most effective pulse parameters) at block 656, (the above-listed operations are iteratively repeated 662 in some embodiments), the most effective pulse-repetition rate for optical stimulation is determined at block 658, and later, at block 660, during normal operation the signals are delivered to the excitable tissue based on the pulse-repetition rate(s) determined to be most effective. In some embodiments, the normal operation of the device uses the different rates that are determined to be most effective for different frequency ranges (i.e., each audio-frequency channel or bin has its own most-effective rate determined, stored and later used) or sound types (e.g., speech versus music).

Figure 7:
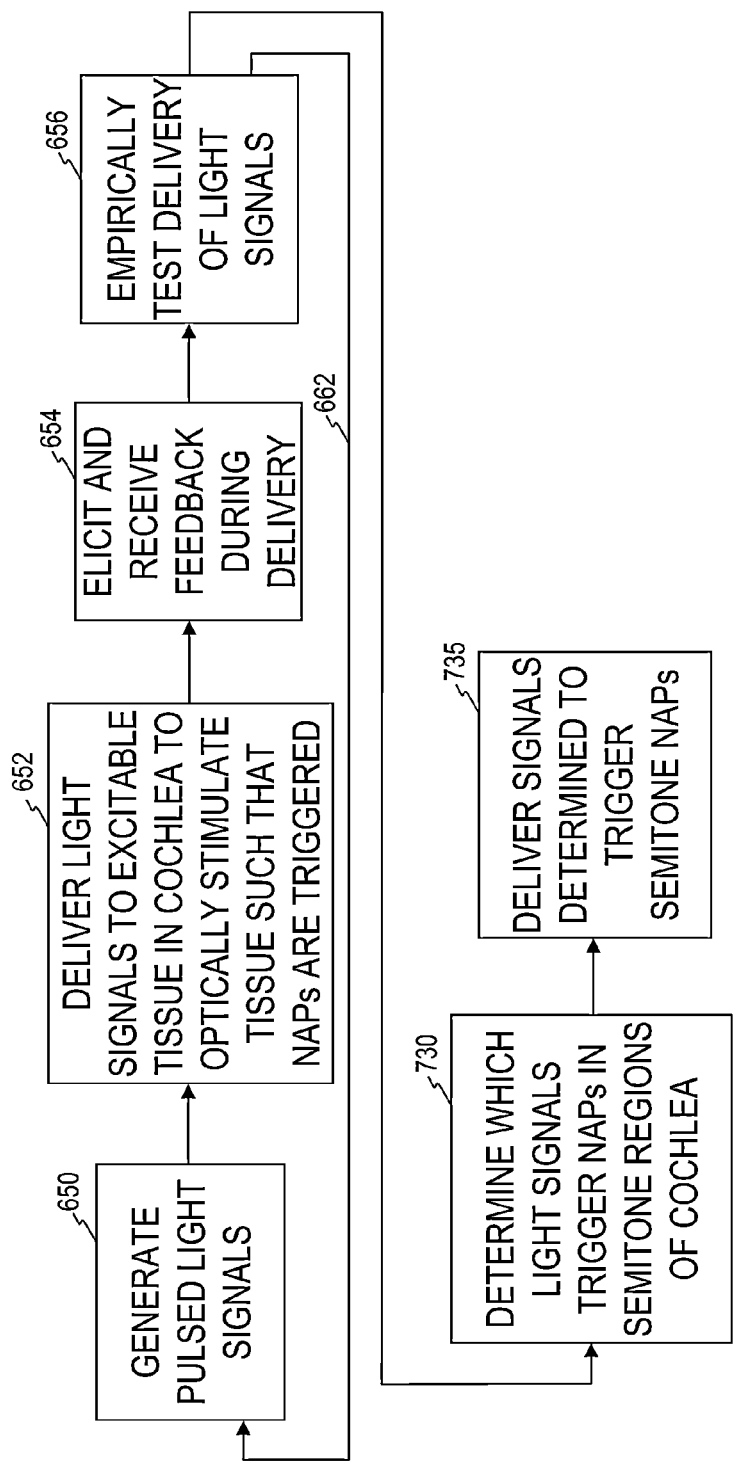
FIG. 7 is a flow chart of a method 700, according to some embodiments of the present invention.

FIG. 7 is a flow chart of a method 700, according to some embodiments of the present invention. The upper portion of this method 700 is similar to method 602 of FIG. 6B, except that the test sounds are customized to improve the patient's enjoyment of music. Again, in some embodiments, pulsed light signals are generated at block 650 (now based on semitone musical notes or other suitable sounds for music), the generated light signals are delivered to excitable tissue in a cochlea of a person to optically stimulate the tissue such that NAPs are triggered at block 652, feedback is elicited and received during (or shortly after) the delivery of the signals at block 654, the delivery of the signals is empirically tested for effectiveness in providing semitone sensations at block 656, (the above-listed operations are iteratively repeated 662 in some embodiments). At block 730, the most effective one or more VCSELs for optical stimulation are determined, and later during normal operation at block 735, the signals are delivered to the specific areas excitable tissue from the selected VCSELs based on the VCSELs determined to be most effective for semitones or other musical features (e.g., many different frequencies for snare drum sounds). In some embodiments, different locations are most effective for different musical types (i.e., each musical type may benefit from selecting VCSEL channels (i.e., selecting from among the set of all optical-stimulation channels) for each music feature differently; these maps of music-to-VCSEL mappings are stored and later used). In some embodiments, each audio-frequency channel uses one or more optical-stimulation channels (i.e., one or more emitters that stimulate a corresponding number of areas of the cochlea) to create a perceived sound sensation associated with the frequencies within the audio-frequency channel. In some embodiments, a large number of emitters are implemented in the implanted device and the calibration process selects, from among the total available emitters, one or more of those that are best suited for a particular hearing environment (e.g., speech versus music listening), and that are then to be used for each of the plurality of perceived sound sensations of that environment.

Figure 8:
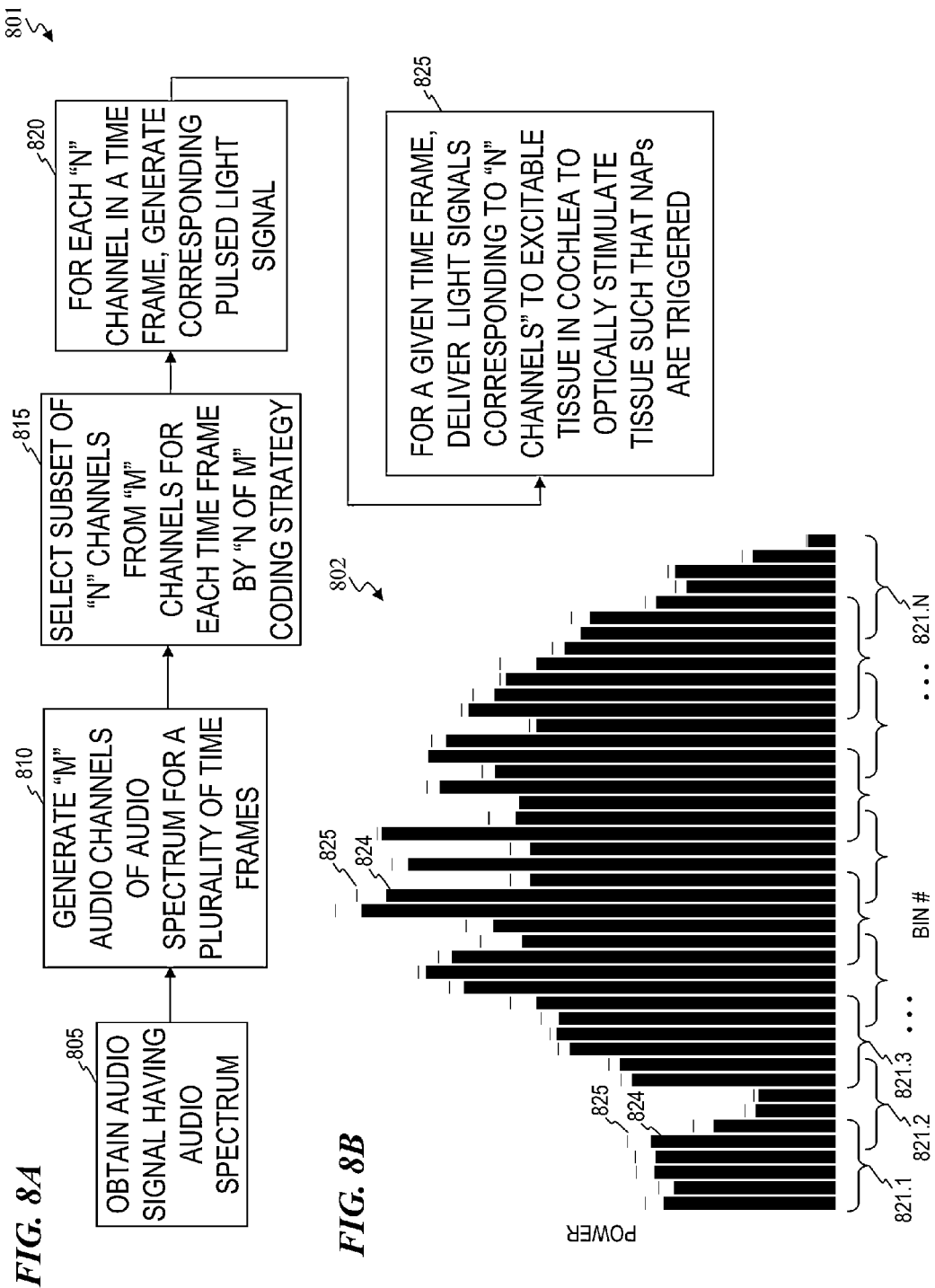
FIG. 8A is a flow chart of a method 801, according to some embodiments of the present invention.
FIG. 8B is a graph of a binned-channel-with-history spectrum 802, according to some embodiments of the present invention.

FIG. 8A is a flow chart of a method 800, according to some embodiments of the present invention. Method 800 is described below.

FIG. 8B is a graph of a binned-channel-with-history spectrum 802, according to some embodiments of the present invention. This graph shows a plurality of audio-frequency channels having current power levels 824 and an indication of recently-past power levels 825. Each one of the plurality of audio-frequency channels is also assigned into one or more bins 812.1-821.N—in the embodiment shown the bins include a plurality of overlapping bins (note that the rightmost two audio-frequency channels of bin 812.1 are the leftmost two channels of bin 812.2, and so on).

Referring to FIG. 8A, at block 805, an audio signal having an audio spectrum is obtained. At block 810, the audio signal is processed into M audio-frequency channels for each of a plurality of successive time frames. At block 815, a subset of up to N audio-frequency channels are selected from the original M channels for the current time frame, based on how many audio-frequency channels are the most active in each bin and optionally how many of those channels or of nearby channels were activated in the recent past. At block 820, one or more pulses of optical-stimulation light are generated for each of the selected N channels active for this time frame. At block 825, the light is delivered to the excitable tissue.

Figure 9:
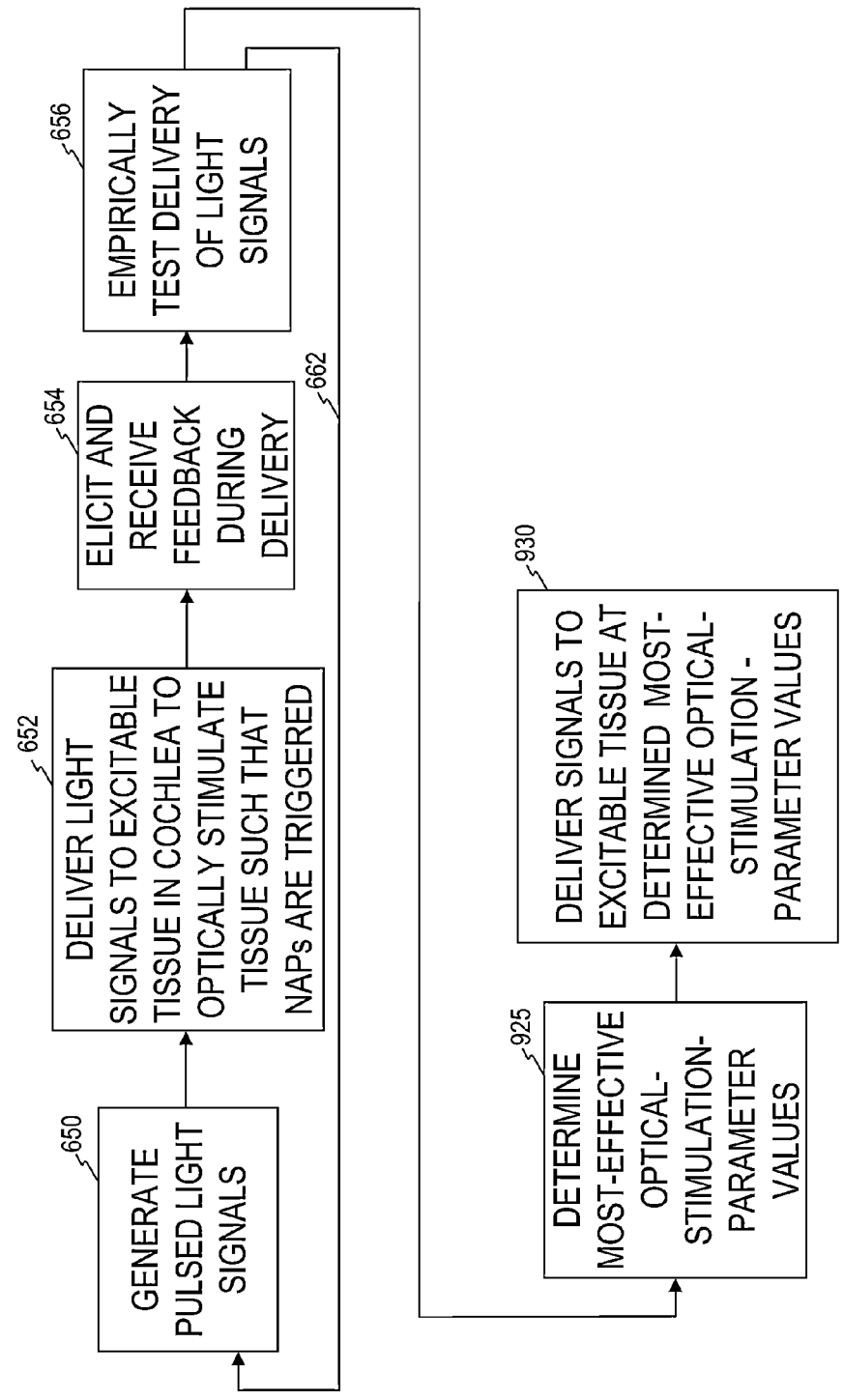
FIG. 9 is a flow chart of a method 900, according to some embodiments of the present invention.

FIG. 9 is a flow chart of a method 900, according to some embodiments of the present invention. The upper portion of this method 900 is similar to method 602 of FIG. 6B, except that the test optical-stimulation parameters are customized to improve the effectiveness of various values to provide a sensation of loudness having an increased dynamic range and/or to achieve some other hearing or comfort goal. Again, in some embodiments, pulsed light signals are generated at block 650 (now having a parameter such as optical spectrum, pulse power, or other parameter being varied), the generated light signals are delivered to excitable tissue in a cochlea of a person to optically stimulate the tissue such that NAPs are triggered at block 652, feedback is elicited and received during (or shortly after) the delivery of the signals at block 654, the delivery of the signals is empirically tested at block 656 for effectiveness in providing a sensation of loudness having an increased dynamic range and/or achieving some other hearing or comfort goal, (the above-listed operations are iteratively repeated 662 in some embodiments). In some embodiments, the empirical testing 656 determines a plurality of parameters that are, as a whole, most effective (e.g., sometimes this produces a compromise between parameters that need to be different for different environments). At block 925, the most effective parameter(s) for optical stimulation are determined, and later during normal operation at block 930, the optical-stimulation signals are generated using the parameter(s) determined here to be most effective for delivering the hearing perception desired. In some embodiments, different parameters are most effective for different speech or musical types (i.e., each musical type may benefit from selecting a different set of parameters, and these mappings are stored and later used).

Figure 10:
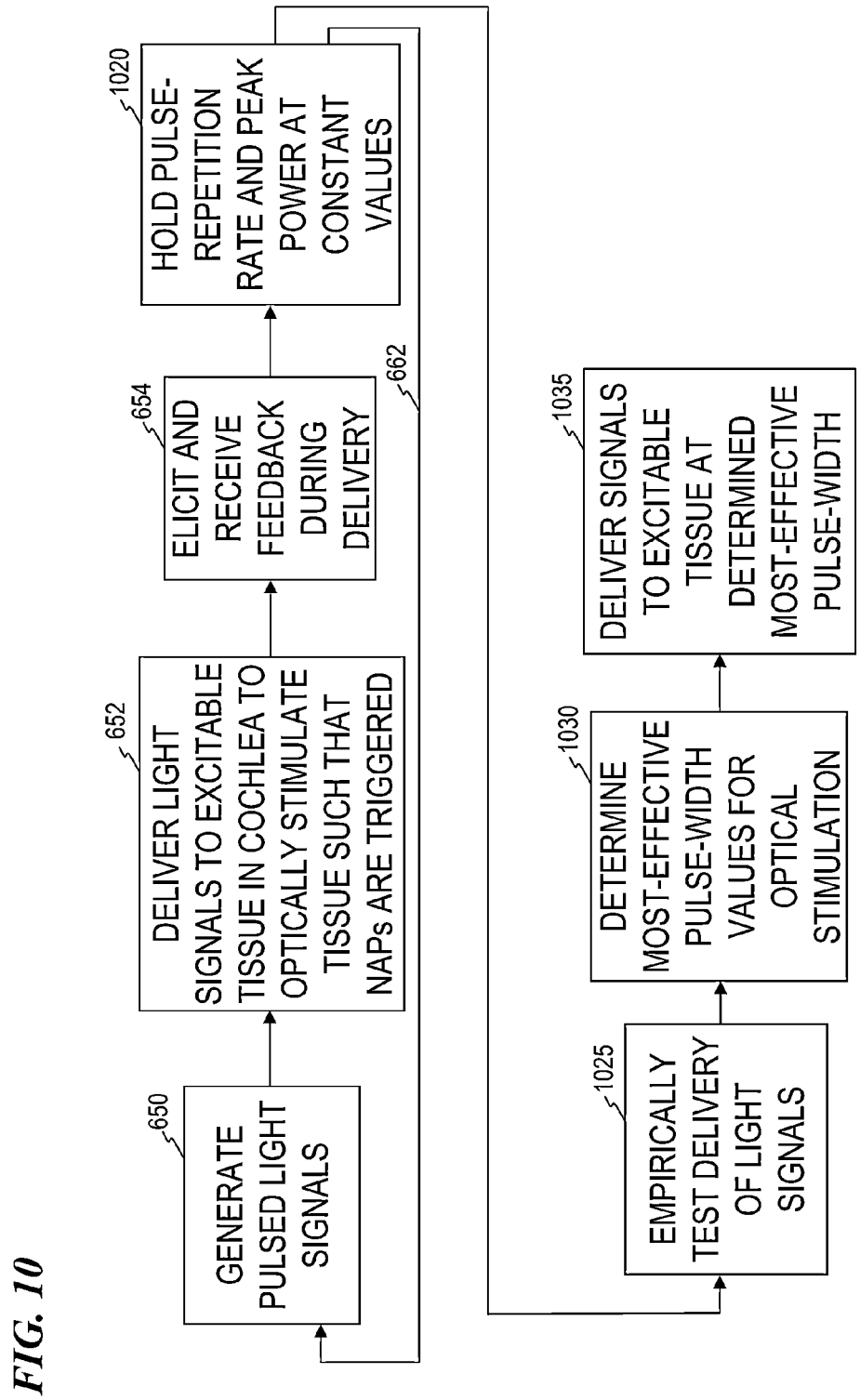
FIG. 10 is a flow chart of a method 1000, according to some embodiments of the present invention.

FIG. 10 is a flow chart of a method 1000, according to some embodiments of the present invention. The upper portion of this method 1000 is similar to method 602 of FIG. 6B, except that the test sets a peak power and a repetition rate at preset values and varies the pulse-width optical-stimulation parameter (and thus varies the energy amount of each pulse) in order to improve the effectiveness of various pulse-width values to provide improved perceived dynamic range of loudness. Again, in some embodiments, pulsed light signals are generated at block 650 (now having a parameter such as pulse width being varied), the generated light signals are delivered to excitable tissue in a cochlea of a person to optically stimulate the tissue such that NAPs are triggered at block 652, feedback is elicited and received during (or shortly after) the delivery of the signals at block 654, at block 1020, the pulse width is varied while maintaining peak power and repetition rate fixed, and the effectiveness of various different pulse widths to give different loudness perception is empirically tested at block 1025, (the above-listed operations are iteratively repeated 662 in some embodiments). At block 1025, the signals are delivered and at block 1030 the most effective parameter(s) for optical stimulation are determined, and later during normal operation at block 1035, the optical-stimulation signals are generated using the parameter(s) determined here to be most effective for delivering the hearing perception desired.

Figure 11:
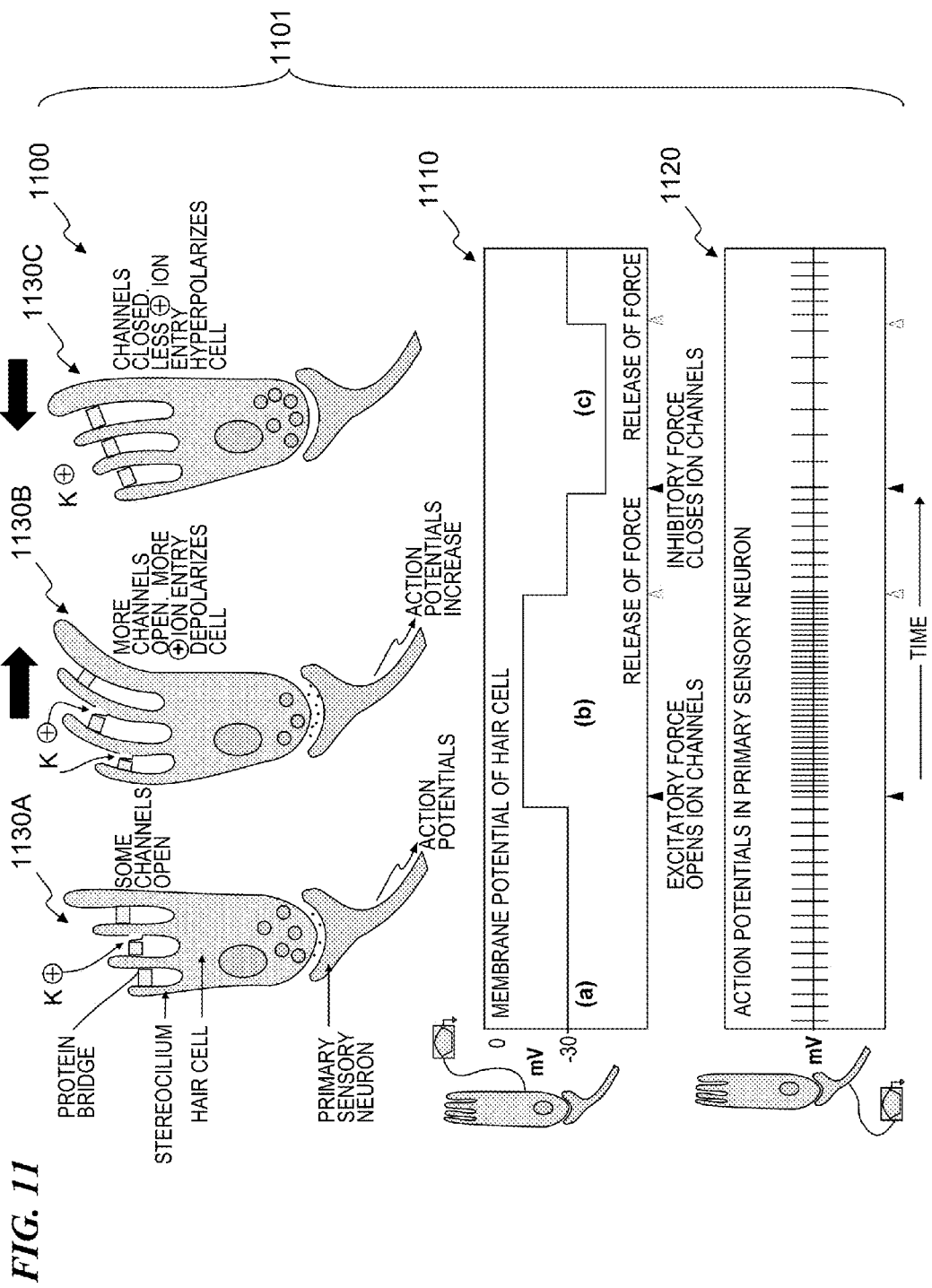
FIG. 11 is a diagram of the firing of auditory nerve cells 1100 as hair cells are deflected.

FIG. 11 is a diagram the firing of auditory nerve cells 1100 as hair cells are deflected (adapted from Kandel et al., 2000). In some embodiments of the present invention, perceived loudness of sounds is varied by changing the auditory-nerve-stimulation rate. In normal hearing physiology, as sound pressure increases, hair cells 1100 are further deflected and action potentials are fired at greater rates (linear relation). Graph 1110 shows the amount of deflection of hair cells 1100. Graph 1120 shows the action potential firing rates corresponding to the differing amounts of hair-cell deflection shown in graph 1110. By varying the stimulation rate, one can convey loudness. The greatest sustainable firing rate (saturation) is about five-hundred (500) spikes per second (Kandel et al., 2000).

Figure 12:
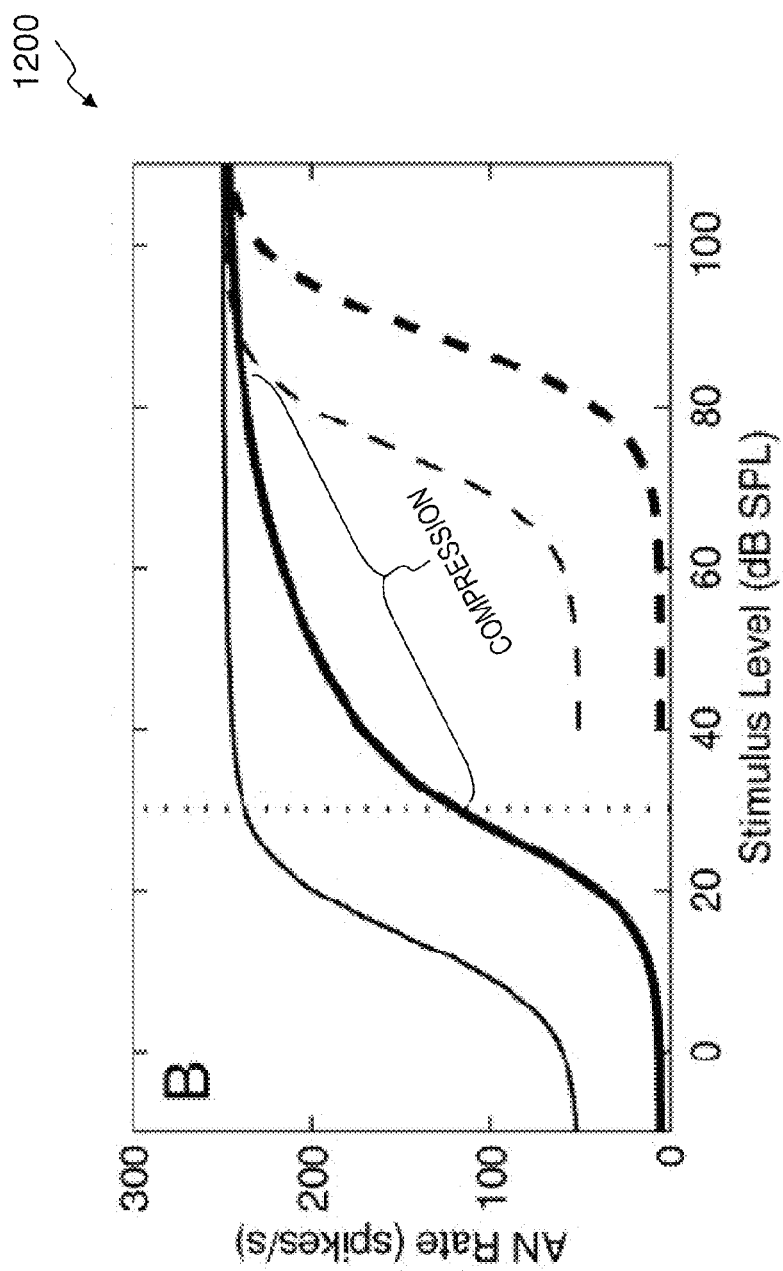
FIG. 12 is a graph 1200 of auditory nerve firing rates versus sound level.

FIG. 12 is a graph 1200 (adapted from Heinz's (2004) adaptation of Sachs and Abbas (1974)) of auditory nerve firing rate versus sound level for acoustically stimulated hearing (i.e., nerve signals from normal hearing in contrast to nerve signals from electrical or optical stimulation of the nerve(s)). Increasing sound intensity causes the peak of basilar membrane vibrations to get bigger, stimulating both inner and outer hair cells (ihc/ohc) more. Increased stimulation of the hair cells causes increased auditory nerve firing rates (AN Rate), as shown in 1200, for both normal ears (solid lines in FIG. 12) and ears having substantial outer-hair-cell damage (dashed lines in FIG. 12). The response of the outer hair cells grows rapidly with increasing intensity at low intensities, but more slowly at higher intensities (compressive). A wide dynamic range is accomplished by this compressive response and by the effect of low-threshold neurons (upper solid and dashed curves) and high-threshold neurons (lower solid and dashed curves). Low-threshold neurons saturate at low-to-mid sound levels. High-threshold neurons become active at higher sound intensities, and saturate at higher sound intensities.

Figure 13:
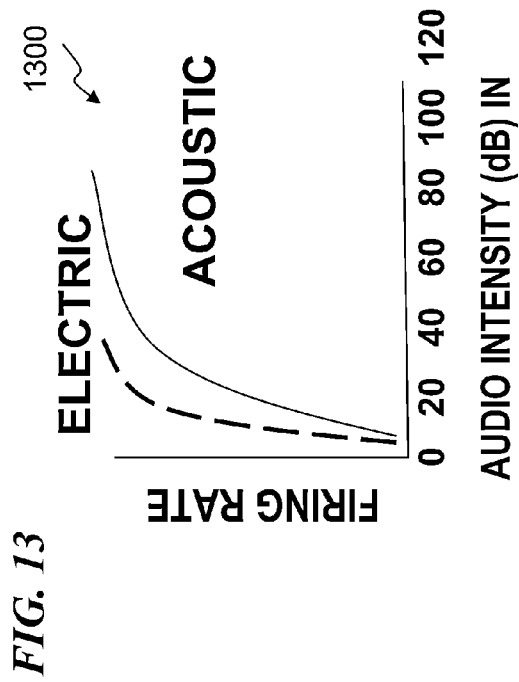
FIG. 13 is a graph 1300 of auditory nerve firing rate versus sound level.

FIG. 13 is a graph 1300 of auditory nerve firing rate versus sound level. Electric current stimulates the auditory nerve fibers in the cochlea, producing action potentials that are conducted to the brain. However, with direct auditory nerve stimulation without the inner hair cells, the nerve fibers differ in threshold only slightly, so the dynamic range of the combined response is much like the response of a single nerve fiber. The result is a steepening of the combined firing-rate curve for electrically stimulated nerves as compared to acoustically stimulated nerves, shown in 1300.

Figure 14:
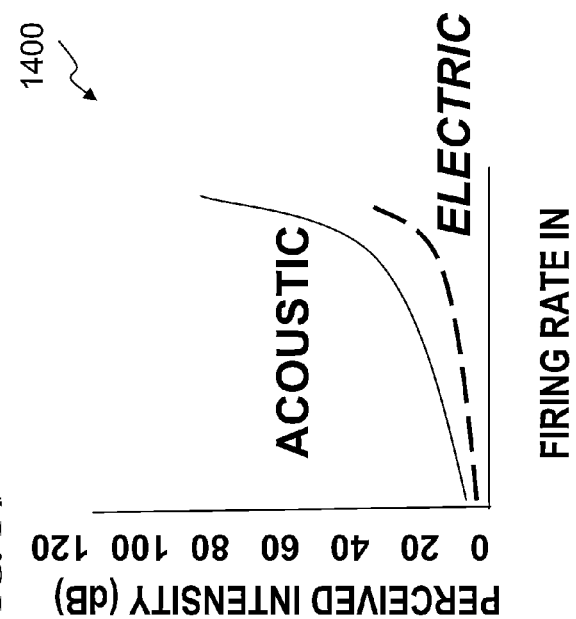
FIG. 14 is a graph 1400 of perceived sound level versus auditory nerve firing rate.

FIG. 14 is a graph 1400 of perceived sound level versus auditory nerve firing rate. If one considers perceived loudness as being driven by auditory nerve firing rate (stimulation rate), the graph shows that loudness (intensity) is a weak function of firing rate: even a large change in firing rate generally results in a small change in perceived loudness. Many papers seem to indicate that perceived loudness is a weak function of stimulation rate in electrical and optical stimulation, including McKay et al. (1998), Vandali et al. (2000), and Littlefield et al. 2010).

McKay et al. (1998) provide a set of graphs of test subject loudness perception at differing electrical-stimulation pulse rates. As described in McKay et al. (1998), cochlear-implant listeners were asked to balance loudness between a test signal at a number of stimulation rates versus a reference signal at a 50-pulses-per-second (pps) stimulus rate. As the perceived loudness of the test signal increased at increasing stimulation rates, the test subjects reduced the strength of the test signal to keep its perceived loudness equal to that of the reference signal. It was clear that, at comfortably loud levels, subjects reduced the strength of the test signal by relatively small amounts (less than 2 dB) over a large range (1000 pps) of stimulation rates. These test results show that increasing auditory-nerve-stimulation rates significantly, results in only small increases in perceived loudness of sounds.

McKay et al. (1998) also provide a set of graphs of test subject average auditory nerve spike probability versus stimulation rate. As described in McKay et al. (1998), the small increases in perceived loudness with increasing stimulation rate are most likely a result of auditory nerve action potential spike probability dropping with increased stimulation rate, which has been observed in optical stimulation (Littlefield et al., 2010). The data showed a drop after 100 pps.

Vandali et al. (2000) provide graphs of signal current level for various auditory-nerve-stimulation rates. In an experiment described in Vandali et al. (2000), cochlear-implant listeners set current levels for all electrodes in their cochlear implant for three different stimulation rates. In the graphs, current level units were clinical units (that used a 2% increase per step). The tests were conducted at various sound levels, including threshold (t-level) and maximum comfortable loudness (c-level). It was clear that stimulation rate did not affect loudness settings significantly. There was only an approximately 1-2 dB variation in perceived signal loudness at the different stimulation rates (which varied with subject).

In experiments described in Littlefield et al. (2010), single auditory nerves of normal-hearing gerbils were first acoustically stimulated, and recordings were made from 403 neurons. The characteristic frequencies of the stimulation sounds were between 118 Hz and 22 kHz. Littlefield et al. (2010) provided a graph of the maximum action potential rates versus stimulation frequency for the observed neurons. The average maximum action potential rate was 158±82 (158 plus-or-minus 82) action potentials per second. Other graphs showed (a) action potential rates versus frequency for acoustically stimulated nerves, (b) graphs of the distribution of numbers of neurons versus frequency, (c) nerve action potential response rate versus stimulation rate, (d) nerve-firing efficiency versus optical-stimulation rate, and (e) the number of neurons (i.e., how many) that responded to each frequency.

In Littlefield et al. (2010), two diode lasers were then used for stimulation of the auditory nerves. They operated between 1.844 µm and 1.873 µm, with pulse durations of 35 µs to 1,000 µs, and at repetition rates up to 1,000 pulses per second (pps). The laser outputs were coupled to a 200-µm-diameter optical fiber placed against a round window membrane and oriented toward the spiral ganglion and at a distance 0.5 mm from the spiral ganglion in the basil turn. Neural activity was recorded for different laser radiant exposures, pulse durations, and stimulus-repetition rates. The recordings were taken from 154 single neural fibers, 67 of which showed stimulation responses. One graph showed the number of neurons that responded to the optical stimulation plotted against their characteristic frequencies: 67 neurons having characteristic frequencies with a range of 450 Hz to 20 kHz responded. Another graph showed the number of neurons that did not respond to the optical stimulation plotted against their characteristic frequencies: 87 neurons having characteristic frequencies with a range of 148 Hz to 10 kHz did not respond to the optical stimulation. Another graph showed the action potential firing rate versus the auditory-neuron-stimulation rate. The number of evoked action potentials was fairly flat as stimulation rate is increased. The laser-evoked response rates were lower than with acoustic stimulation. The average maximum action potential rate was 97 plus-or-minus 53 action potentials per second. Another graph, which plotted neuron firing efficiency versus stimulation rate, showed that firing efficiency drops after 100 pulses per second (pps).

In some embodiments of the present invention, loudness is encoded in stimulation rate. Fu et al. (2000a) provide a graph of phoneme recognition as a function of stimulation rate in six Nucleus-22 cochlear implant listeners. Data from Fu et al. (2000a) indicate that speech recognition requires repetition rates (auditory-nerve-stimulation rates) at least about 150 pulses per second (pps). A damage threshold may limit pulse-repetition rates to no more than about 300 pps (personal communication from Claus-Peter Richter, Northwestern University, a sometime collaborator of the inventors). For an optical-stimulation rate in the range of 150-300 pps, a less than 2 dB dynamic range is expected.

In some embodiments, the design is based on the dynamic range needed. Fu et al. (2000b) show graphs of phoneme recognition as a function of stimulus dynamic range of the electrical stimulus of a cochlear implant. The data from Fu et al. (2000b) show percent correct phoneme recognition rates for 3 test subjects. Consonant and vowel phonemes were tested separately, and tests were conducted at three different signal-compression levels, p=0.1 (high), p=0.2 (medium) and p=0.4 (low). The data from Fu et al. (2000b) show that the stimulus dynamic range should be at least 5-10 dB. It has been shown that the loudness of an electrical stimulus in microamps (µA) is analogous to the loudness of an acoustic stimulus in dBs. Loizou (2006) showed that a 5-dB dynamic range is sufficient for phoneme recognition, and that electrical-stimulation cochlear implants provide at least a 5-dB-stimulus dynamic range. Nelson et al. (1996) showed that cochlear-implant listeners perceive seven to forty-five (7-45) sound-intensity steps. Fu et al. (2000b) showed that phonetic discrimination drops when the dynamic range is less than 6-to-8 dB.

Using Both Optical and Electrical Stimulation in a Cochlear Implant

In some embodiments, the present invention provides an apparatus and method in which one or more electrical-stimulation electrodes are included at the apical end of the cochlear implant and used to evoke an auditory sensation corresponding to low-audio-frequency content of the sound in the environment, which is especially helpful in speech recognition. As noted above, in conventional electrical-only cochlear stimulation, one challenging problem is the spreading of the electrical signal through the conductive fluid and tissue in the cochlea. Optical stimulation does not suffer this problem and therefore has an advantage in its ability to stimulate in a more specific manner, which leads to higher spectral fidelity for the implantee. A challenge arises, however, to stimulate the apical spiral ganglion cells which sense sound signals at the lower frequency range (e.g., in some embodiments, less than about 250 Hz) because the size and shape of the implant does not readily reach the apical end of the cochlea's openings (e.g., the larger of these cochlear channels, the scala tympani, is typically used for the implant) there is no spreading of the optical signal to illuminate and stimulate the cells beyond the tip of the implant, deep in the cochlea. Conventional electrical stimulators inserted to the same depth can access these deeper regions because of the spread of electricity reaches nerves deeper into the cochlea. In some embodiments of the cochlear implant device of the present invention, twenty-two (22) audio-frequency channels (or other suitable number of audio-frequency channels) are selected from a set of at least that many total emitters of the device and used for optical stimulation (these selected ones are sometimes called the active optical-stimulation channels for sound sensations to be perceived by the user and in some embodiments, are selected from a set of many more available emitters in the device by empirical testing to determine the ones that are most effective at each perceived frequency) along the implantable region within the cochlea and one or more electrodes are used at the deepest apical end of the implant to stimulate beyond the end of the implant. This additional electrical-stimulation channel (or electrical-stimulation channels each of which corresponds to one or more audio-frequency channel) provides improved low-audio-frequency sensations for the high spectral fidelity delivered by the optical stimulation from 6000 Hz down to the deepest implantable region (about 250 Hz), by additionally providing stimulation deeper in the cochlea by one or more electrodes at the end of the implant.

As used herein, an "audio-frequency channel" is the signal and/or value representing audio power within a narrow band of audio frequencies, and each "audio-frequency channel" refers to the entire path from the audio processor to the optical-stimulation signal launched towards the cochlea neural tissue for its frequency band. The audio processor "dissects" the full spectrum of the input audio (e.g., using a fast-Fourier transform (FFT), discrete cosine transform (DCT) or other suitable algorithm or method) into a plurality of frequency bands (used for the respective audio-frequency channels), each representing content of audio power within a predetermined range of audio frequencies. An "audio-frequency-channel bin" is a group of adjacent audio-frequency channels that forms one of a plurality of subsets of the full set of audio-frequency channels. In some embodiments, audio-frequency-channel bins overlap with one another; for example, the first audio-frequency-channel bin may include only audio-frequency channels 1-5, the second audio-frequency-channel bin may include only channels 4-8, the third audio-frequency-channel bin may include only channels 7-11, and so on (such that audio-frequency channels 4-5 are included in both bin 1 and in bin 2 (such that bin 1 and bin 2 overlap by two audio-frequency channels), while audio-frequency channels 7-8 are included in both bin 2 and in bin 3 (such that bin 2 and bin 3 overlap by two audio-frequency channels), but bin 1 and bin 3 do not overlap and audio-frequency channel 6 is not included in either bin 1 or bin 3. In this way, the method of the present invention can prevent simultaneous activation of two or three of any three adjacent audio-frequency channels during a single time frame or a time period having a predetermined number of P (e.g., two or more) successive time frames. The variable "M" represents the number of channels in the full set. The variable "N" represents the maximum number of channels in the subset of channels that are allowed to be activated at a given time. The value of N may vary over time—e.g., N may have a larger value after a time period that had a continued low level of audio, but may have a value that starts small and gradually increases over time after a period of very low (quiet) audio in order not to jolt or overstress the auditory portion of the patient's brain, and may have a value that gradually decreases over time after a period of very high (loud) audio that may have caused heat build-up in one larger localized area (i.e., an area that is the destination of two or more optical-stimulation channels) of the cochlea, or in the cochlea as a whole. In addition, in some embodiments, as described herein, the up-to-N channels that are selected for activation in a given time period are selected so as to spread out the area over which stimulation light is applied so as to avoid overheating small or localized areas in the cochlea. The term "frame" or "time frame" is the smallest quantum of time in which audio power is divided by the software and/or control electronics of the present invention for the purposes of limiting heat buildup, and in various embodiments each frame may be about 4 milliseconds (which results in 250 frames per second) to about 7 milliseconds (which results in about 141 samples per second). In some embodiments, a running history of the most recent H values in each channel and/or each bin is maintained, allowing the method of the present invention to also limit the number of times any one channel or group of channels may be activated within H successive time frames.

Optimizing the Pulse-Repetition Rate of an Optical Cochlear Implant

Limitations on the upper limit of optical-stimulation pulse-repetition rate exist for optical-stimulation devices—limitations that are based on deleterious heating effects in the cochlea. However, speech recognition is also based on stimulation rate, and often benefits from a higher stimulation pulse-repetition rate. In some embodiments of the present invention, stimulation rate (i.e., pulse-repetition rate) is optimized for the patient based on comfort levels, speech-recognition scores, and temperature feedback from monitors in the cochlea. Thus, in some embodiments, the methods of the present invention find practical lower and upper limits to the rate of stimulation to increase the speech-recognition scores while implementing safety limits to preventing overheating. In some embodiments, stimulation is optimized for speech recognition and is kept above 150 pulses per second (pps), based on findings that speech recognition degrades below 150-pps pulse-repetition-rate-per-channel (see, e.g., Fu et al., 2000a). In some embodiments, pulse-repetition-rate optimization is performed by determining the number of stimulation channels that can be simultaneously stimulated at a given pulse-repetition rate. In other embodiments, pulse-repetition-rate optimization is performed by determining the pulse-repetition rates to use per channel.

Loudness perceived by a patient is a weak function of stimulation rate. Optical stimulation is limited to 150-to-300 pulses-per-second (pps) range. In some embodiments, a stimulation rate of at least 150 pps is required for speech recognition. In some embodiments, a stimulation rate of no more than 300 pps is required to stay below the damage threshold (e.g., the pulse-repetition rate that risks damage from heating the tissue being optically stimulated or nearby tissue). This range of pulse-repetition rates only allows less than 2 dB of loudness dynamic range. Further, some experiments have shown firing efficiency drops significantly with a stimulation pulse-repetition rate over 100 pps, and the action potential rate plateaus after about 50-100 pps. Little or no speech information can be conveyed through a stimulation rate below about 100 pps. This is not sufficient for improvement over current electrical stimulation. Therefore, some embodiments encode loudness information in the pulse width of the optical pulses used for stimulation.

Additionally, in some embodiments, stimulation rate is kept below a rate which overheats the cochlea. In some embodiments, a temperature monitor is placed inside the cochlea to monitor and feedback a temperature for use in limiting the stimulation rate and/or other parameters such as peak optical power, wavelength, and pulse width. In other embodiments, the temperature of the cochlea is modeled. Additionally, in some embodiments, the temperature monitor serves as a feedback to a safety shut-off switch in the case of overheating. Further, in some embodiments, the present invention provides a patient-activatable electromagnetic emergency-off mechanism.

In some embodiments, the implanted device 110 includes a "fail-safe" circuit 588 (see FIG. 5) that immediately (or after a short predetermined amount of time) turns off all stimulation devices (including lasers or other optical sources, as well as the electrical-stimulation drivers) if and when communications are lost to the externally worn device 111. In this way, if excess loudness or other discomfort is perceived, the patient can simply remove the externally worn device from their body and move it to a distance far enough away from the implanted device that the wireless communications is disconnected, in order to actuate the fail-safe circuit 588. In some embodiments, the externally worn device 111 periodically transmits a periodic "heart-beat" signal that, as long as it is detected (within each successive time period of a predetermined duration) by the fail-safe circuit 588, prevents the fail-safe circuit 588 from turning off all stimulation devices, but once a predetermined amount of time passes in which no "heart-beat" signal is detected, the fail-safe circuit 588 turns off all stimulation devices.

In some embodiments, the present invention provides an apparatus and method in which the stimulation rate is optimized for the patient based on comfort levels, speech-recognition scores, and temperature feedback from monitors in the cochlea. Stimulation can be optimized for speech recognition and should be kept above 150 pulses per second (pps) based on findings that speech recognition degrades below a 150-pps per channel. Additionally, stimulation rate should be kept below a rate that would overheat the cochlea. In some embodiments, one or more temperature sensors or monitors are placed inside the cochlea to monitor and provide feedback signals indicative of temperature for use in limiting the stimulation rate and/or other parameters, such as peak optical power, wavelength, and pulse width. Additionally, in some embodiments, the temperature monitor generates a feedback signal to a safety shut-off switch in the case of overheating. This problem is new, as optical stimulation of the cochlea is new. In some embodiments, the apparatus includes a patient emergency-off switch (e.g., electro-magnet in externally worn device transmits a periodic signal through the skin to keep the implant active). When patient removes externally worn device from the head, the implant no longer receives the periodic signal and turns off the stimulation signals).

Providing Enhanced Music Perception in an Optical Cochlear Implant

Patients having conventional electrical cochlear implants usually do not enjoy the perception of music, as the electrical stimulation cannot specifically excite the regions of the cochlea that tonotopically represent the semitones of Western music. It would be nearly impossible to place the electrodes exactly at the semitone locations. Further, even if the electrodes were placed directly over the semitone regions, the electrical signal would spread too much to specifically excite the regions of interest. The use of optical sources to deliver light to the cochlea for purposes of stimulation brings the advantage of increased spectral fidelity because the illumination can be more specifically placed than electrical signals.

In some embodiments, a large plurality of light sources or light-delivery devices are placed along the cochlea, but only a relatively small fraction of them are used due to the limitation of power delivery and a restriction on heat within the cochlea. The large number of implemented emitters also allows selection of the best positions for stimulation without a priori knowledge of the exact placement, since the device can be tested, calibrated and optimized to pick the best emitters that most exactly stimulate the desired locations, and periodically repeat this process to reprogram and recalibrate the device. The ability to choose the sources used further provides the ability to choose the sources which illuminate the semitones found in Western music. This ability to access the exact places in the cochlea where semitones are psychophysically represented will improve musical perception in the patient.

In one embodiment, a plurality of light sources are connected through a series of fuses that can be "blown" to permanently disconnect those devices that are not to be used, and thus select the desired source(s) in the region of interest. In other embodiments, similar to a programmable logic array, the logic is programmable and settable during optimization of the device for the patient, and optionally reprogrammable and re-settable during a later re-optimization. In some embodiments, optical stimulation optimized, or at least improved, for music perception is a user-selected mode of the cochlear implant. In some such embodiments, optimization for music perception is one of a plurality of user-selected modes. In some embodiments, music-perception optical stimulation uses "N-of-M" signal coding, as described below. In other embodiments, the sources selected to be used are re-programmably or dynamically (i.e., non-permanently, reprogrammably, and/or in a manner that changes over time) activated according to a stored table or other mechanism within the implant and/or the externally worn device (e.g., a device having a microphone, some audio-processing capability and a wireless transmitter that transmits (to the implanted device) information corresponding to the microphone-sensed audio).

In some embodiments, an audio processor analyzes the incoming audio signal from the microphone or other input device and makes a determination as to the content of the signal, that is, whether the audio signal is primarily speech, or primarily music. In some embodiments, one or more of the regions of the cochlea that are stimulated are automatically changed to optimize either music perception or voice perception, based on the device detecting primarily voice or primarily music content in the received audio. In other embodiments, a music-perception stimulation mode is selected, from one of a plurality of listening modes, by the wearer of the implant manually activating an electrical switch, a magnetic trigger, an accelerometer configured to detect a tip of the head of the wearer, or other input device on the external portion of the implant system. In some embodiments, the frequency range stimulated in the cochlea can be changed depending on the type of audio signal being received. In some embodiments, both the bandwidth of the processed signal and the pitch range are dynamically altered based on the listening mode (whether the mode is automatically selected or user selected). In some embodiments, the incoming audio signal is processed in a way that shifts the nerve regions being stimulated (analogous to shifting the audio in frequency (higher or lower)) to nerve regions that work better (or that are sensed to be more enjoyable) for music perception.

In some embodiments, "semitone" is defined to mean the interval between adjacent notes in the twelve-note equally tempered scale. The frequency ratio between two adjacent semitones is $2^{(1/12)}$ (the $12^{th}$ root of two):

$$\text{(Frequency of Semitone } N\text{)}/\text{(Frequency of Semitone } N-1) = 12^{th} \text{ root of two} \qquad \text{(Eqn. 1)}$$

The twelve-note equally tempered scale is commonly used in Western music. In other embodiments, the "semitone" for adjacent notes is based on other scales or tunings which do not have equal ratios between semitones, or which use a scale having equal ratios between notes but having other than twelve notes. Examples of these other tunings include the historic Pythagorean Tuning, and Just Intonation commonly used by A cappella groups.

The objective in calibrating a cochlear implant to a specific individual is to achieve pleasurable perception and/or improved recognition of music. Causing the patient wearing the implant to perceive the actual frequencies in a music source is not necessary. To enhance the perception of music, the intervals between notes (musical pitches), being played either simultaneously or successively, must be correctly perceived by the patient. Intervals (the frequency difference) between notes can be characterized as an integral number of semitones. There are multiple definitions of "semitone" depending on, for example, type of music, historic time period of music, type of musical instrument, and musical culture (e.g., oriental versus western). Therefore, a cochlear implant in a particular patient is calibrated so musical intervals sound pleasing to that individual.

In some embodiments, calibration of an implant is performed as follows. This particular method is analogous to a piano-tuning method described by Fischer (1907/1975) in "Piano Tuning" An initial musical pitch is chosen from which to perform the calibration. In some embodiments, the initial pitch is a C4 frequency (commonly known as middle C) as that pitch would be extracted from received audio signal of music. In other embodiments, the initial pitch is C5 (the C one octave middle C). In other embodiments, some other initial pitch is used. In the following description of one embodiment, an initial pitch of C4 is used. An optical-stimulation channel is assigned to C4 such that the optical-stimulation channel triggers nerves in the cochlea near the region of the cochlea that responds to the C4 pitch. See Omran et al. (2011), "Semitone Frequency Mapping to Improve Music Representation for Nucleus Cochlear Implants" for a description of mapping particular frequencies to locations along the basilar membrane. Next, an initial optical-stimulation channel is assigned to the pitch C5 that stimulates nerves in the cochlea near the region of the cochlea that responds to C5. Again, from Omran et al. (2011) an approximate location along the basilar membrane can be determined. A C4-pitched tone and a C5-pitched tone are played for the patient whose cochlear implant is being calibrated, and those tones are received and processed into optical-stimulation output, wherein in some embodiments, the two tones are played simultaneously (two cochlear areas stimulated simultaneously), and then are alternated (the two cochlear areas stimulated alternately). As the C4 and C5 tones (simultaneous with one another and/alternating with one another) are received and decoded, the optical-stimulation channel selected for C4 is excited/operated, and the initial C5 site excited by the initial optical-stimulation channel, and one or more alternate "C5" sites and optical-stimulation channels near the one initially assigned to the pitch C5 are excited/operated to "play" the C5 tone to the patient. Stimulation of stimulation sites that are not quite "an octave apart" may be perceived as discordant or unpleasant by the patient. The patient is asked to choose which optical-stimulation channel provides the patient with the best perception of two tones separated by an octave (sites that cause the most pleasant or least discordant or unpleasant sensation), and this optical-stimulation channel is assigned to the pitch C5. A corresponding procedure is then repeated for the C3 pitch (stimulating the C4 site and sites around an initial C3 site).

With octave pitches assigned to specific optical-stimulation channels, the rest of the musical pitches are then calibrated. An initial optical-stimulation channel is assigned (see Omran et al., 2011) for the G3 pitch (G a musical fifth (5 semitones) above C3). An interval of a fifth is used because most individuals, even those with no musical training can identify a fifth: musically, it sounds pleasant (it is perceived as pleasant). As in assigning optical-stimulation channels to the octave pitches, C3 and G3 pitched tones are played (simultaneously and/or alternately) for the patient. Optical-stimulation channels near the one initially chosen for G3 are used to "play" the G3 tone, and patient feedback used to assign the optical-stimulation channel that provides him or her with the most pleasant sensation (hopefully, the best perception of a musical fifth). The octave-determining process is repeated for the G4 pitch (using the G3 site and a plurality of sites to locate one for G4 that is best perceived as an octave above G3). In some embodiments, as a check, a G4 pitched tone is played with a C4 pitched tone (a musical fifth interval), and the optical-stimulation channel assigned to G4 slightly adjusted so that both octave interval (above G3) and the fifth interval (above C4) both sound most pleasant to the patient. The process is repeated for other pitches in the musical scale, doing D4 (a fifth above G3) next, then D3 (an octave below D4, and so on. In some embodiments, the calibration is done using only intervals of octaves and fifths, which are easy for most people to recognize. In some embodiments, where the cochlear implant has an extended frequency range (more than 2 octaves), the above process is repeated to extend the perceived musical range. In other embodiments, additional or alternative musical intervals are used (such as musical thirds and/or sevenths). In some embodiments, an additional process is used to identify a best set of immediately adjacent semitones, wherein two adjacent semitones are discerned as discordant when played simultaneously, but a scale of 8 or 12 successive notes is perceived as "equally tempered" by the patient. In some embodiments, the entire process or portions thereof is iteratively repeated to fine tune the perception of an equally tempered scale and harmonies formed from such a scale. In some embodiments, a succession of chords of two or more simultaneous notes is played to further fine tune the patient's perception of music.

In other embodiments, calibration of the cochlear implant is performed by initially assigning optical-stimulation channels to all pitches, for example, using the mathematics described in Omran et al. (2011):

Equation 2 below describes the characteristic frequencies at distance x mm from the cochlea's apex according to Greenwood's empirically derived function which was verified against data that correspond to a range of x from 1 to 26 mm [12].

$$f(x) = 165.4(10^{0.06x} - 1) \qquad (2)$$

$$\Rightarrow x(f) = \frac{1}{0.06}\log\left(\frac{f}{165.4} + 1\right) \qquad (3)$$

The distance (in mm) between two locations with different characteristic frequencies $f_1$ and $f_2$ is given by Equation 4

$$\Delta x = x_2 - x_1 = \frac{1}{0.06}\log\left(\frac{f_2 + 165.4}{f_1 + 165.4}\right) \qquad (4)$$

In some embodiments, after the initial assignment of optical-stimulation channels, easily recognizable pieces of music are played for the patient. A music-recognition score, based on feedback from the patient, is used as a guide in fine tuning the assignment of optical-stimulation channels to specific pitches.

In some embodiments, the present invention provides an apparatus and method in which optical sources deliver light to small specific areas of the cochlea for purposes of stimulation, which brings the advantage of increased spectral fidelity (fine-grained audio frequency perceived by the patient) because the stimulation illumination can be more specifically placed than electrical-stimulation signals. Conventional electrical-stimulation-only cochlear-implant patients often do not enjoy the perception of music, as the electrical stimulation cannot specifically excite the regions of the cochlea that tonotopically represent the semitones of Western music. It would be nearly impossible to place the electrodes exactly at the semitone locations in the cochlea. But, even if the electrodes were placed directly over the semitone regions, the electrical signal would spread too much to specifically excite the regions of interest. In some embodiments of the present invention, a plurality of light sources or light-delivery devices are placed at finely-spaced locations along the cochlea, but only a fraction of them are used within any short period of time due to the limitation of power delivery to the optical emitters and a restriction on heat within the cochlea due to the absorption of the optical-stimulation signals. The ability to choose which optical sources are used at any given time frame provides the ability to choose the sources that illuminate and thus stimulate the particular small areas of the cochlea that generate nerve signals perceived as the semitone frequencies found in Western music. This ability to access the exact places in the cochlea where semitones are psychophysically represented will improve musical perception by the patient. In one embodiment, multiple sources are connected through a series of fuses that can be "blown" to select the desired source in the region of interest. Similar to a programmable logic array, the logic could be programmable and settable during optimization of the device for the patient. In other embodiments, the sources selected to be used are re-programmably or dynamically (i.e., in a manner that changes over time) activated according to a stored table or other mechanism within the implant and/or the externally worn device (e.g., a device having a microphone, some audio-processing capability and a wireless transmitter that transmits (to the implanted device) information corresponding to the microphone-sensed audio.

Encoding Information in an Optical Cochlear Implant for Minimal Heat Effects

In electrical stimulation, the challenging problem is the spreading of the electrical signal through the conductive fluid and tissue in the cochlea. Optical stimulation does not suffer this problem and therefore has an advantage in its ability to stimulate in a more specific manner, which leads to higher spectral fidelity for the implantee. One challenge, however, is heating of the tissue by the optical channels. Because the physiological mechanism for stimulation using optical signals is thermal, careful engineering is needed to allay thermal buildup in the cochlea. In some embodiments, signal-coding strategies are used to reduce the number of channels on at any given time and therefore reduce the average power delivered and heat produced. In some embodiments, a commonly used coding strategy is the "N-of-M" coding strategy, where the input frequency spectrum is analyzed by the signal processor and spectral power is dissected into M channels, then, by subsequently determining the N channels with the highest power, those channels are stimulated by the corresponding electrodes in the implant. In some embodiments, this is done frame by frame, where the frame rate is the refresh rate of the data processor (in some electrical cochlear implants, this is done for the reason that electrical cochlear implantees cannot utilize more than 8 channels due to electrical spread in the cochlea).

In some embodiments, an N-of-M coding strategy is used, while placing a quota on the number of channels selected to illuminate in each frame. Speech tends to fill the audio frequency spectrum between 50-6000 Hz and conventional electrical-stimulation cochlear implant speech processors tend to cover the range 240-6000 Hz, depending on insertion depth. In some embodiments of the present optical-simulation cochlear-implant invention, an audio range of 50-6000 Hz or other suitable range is used, wherein this total audio range is broken into 22 (or other suitable number of) audio-frequency channels and 11 (or other suitable subset number of) these audio-frequency channels are illuminated at each time-frame cycle (sometimes simply called "frame" herein). In other embodiments, rather than simply illuminate the 11 frequency-based channels of the detected audio spectrum having the highest power during a given time-frame cycle, there is a quota to illuminate at least X channels from each bin of channels (wherein, in some embodiments, for some bins, X is zero or more, while for other bins, X may be one, two, or more channels) and no more than Y channels from each bin. This limits the number of illuminated channels-per-length of cochlea and therefore prevents localized heating of the cochlea and reduces power consumption of the device. In some embodiments, rather than using non-overlapping bins (wherein the lowest-frequency channels of one bin could be contiguous with the highest-frequency channels of an adjacent bin), overlapping bins are used, such that the Y limit on channels (i.e., how many channels in one bin that are allowed to be active in a given predetermined period of time) applies to adjacent areas that might have been in different bins if non-overlapping bins were to be used.

In some embodiments, the present invention provides an apparatus and method in which a subset of N frequency-based stimulation channels are selectively activated from a set of M measured frequency-based audio values (N-of-M coding) for each given time frame. One coding strategy used in conventional electrical-stimulation cochlear implants is an N-of-M coding strategy, where the input frequency spectrum is analyzed by the signal processor and spectral power is dissected into M frequency-based channels, then, by subsequently determining the N channels with the highest power, those channels are activated to stimulate the corresponding electrodes in the implant. This is done frame by frame, where the frame rate is the refresh rate of the data processor. This is done for the reason that some conventional electrical implantees cannot utilize more than eight (8) channels due to electrical spread through the conductive fluid and tissue in the cochlea. Optical stimulation does not suffer this "spreading" problem and therefore has an advantage in its ability to stimulate in a more specific and fine-grained manner, which leads to higher spectral fidelity for the implantee. One challenge, however, is heating of the tissue by the optical channels (particularly when activating many channels that are close in space and/or that are activated close in time). Because the physiological mechanism for stimulation using optical signals is thermal (i.e., heat is needed to trigger the desired CNAPs, careful engineering is needed to allay thermal buildup in the cochlea. In some embodiments of the present invention, signal coding strategies are used to reduce the number of channels active within a predetermined amount of time and within a given volume of tissue, therefore controlling (limiting a maximum amount of) the average power delivered and heat produced. In some embodiments, an N-of-M coding strategy is used for the optical stimulation of the cochlea (or other neural tissue) that is different than those used for electrical stimulation. In some embodiments, the optical N-of-M coding place a quota on the number of and spacing of frequency channels selected to illuminate tissue during each time frame. Speech tends to fill the frequency spectrum between 50-6000 Hz and cochlear-implant speech processors tend to cover the range 240-6000 Hz, depending on insertion depth. In some embodiments, the present invention breaks this range into 22 (or other suitable total number) frequency-based channels and limits the optical stimulation generated to illuminate a maximum of 11 (or other suitable subset number) at each time-frame cycle. In some embodiments, the total number of frequency-based channels is divided into a plurality of adjacent-frequency-based "bins," wherein each bin corresponds to one or more optical emitters within the cochlea that are close to one another in space (and thus each bin corresponds to a subset of adjacent frequencies within the spectrum of audio frequencies used by the audio processor. In some embodiments, rather than simply activating the 11 highest-power channels, some embodiments use a quota to illuminate at least X channels from each bin of channels for a plurality of bins (e.g., in some embodiments, depending on the frequency content and loudness of the sounds received by the microphone the number of bins having this minimum number of channels activated may vary) and no more than Y channels from any one bin. This limits the number of activated channels (adjacent illuminated areas) per unit length (or volume, in some embodiments) of cochlea and therefore prevents localized overheating of the cochlea and reduces power consumption of the device.

Optimization of Individual Performance of an Optical Cochlear Implant

When a patient is implanted with a cochlear implant, the implant remains off for a period of time while the patient's body adapts to the implant. The patient then visits an audiologist to initiate use of the device and set parameters for best operation in the individual.

In some embodiments, a plurality of parameters is specified by the computer program used to implement the optimization of the present invention, or specified to the program by the audiologist (or patient) utilizing the program, as potential mechanisms for optimizing implant performance for the individual patient. In some embodiments, the following parameters are used to encode information on the optical signal:

pulse width, peak power, stimulation rate, wavelength, polarization, wavelength profile, beam profile, beam angle.

In some embodiments, the following parameters are used to optimize the implant performance during tuning of the device after implantation: pulse width, amplitude, frequency, wavelength, polarization, wavelength profile, beam profile, beam angle, coding strategy (e.g., N-of-M), signal-processing filter bandwidths, signal-processing filter shapes, signal-processing filter center frequencies, and operational/functioning channels. Individual patients may find a range of comfort levels and settings that provide best performance of the device for each one of a plurality of different listening environments (driving a car, voice conversations, music listening and the like). In some embodiments, the audiologist adjusts the above parameters to provide the patient with best performance. In some embodiments, best performance is judged by speech recognition, loudness comfort levels, physical comfort, and/or device battery life between rechargings of the battery.

In some embodiments, the present invention provides an apparatus and method in which an audiologist's console computer when a cochlea-stimulation device is implanted into a patient, the implant is programmed to remain off for a period of time while the patient's body adapts to the implant. The patient then visits an audiologist to initiate use of the device and set parameters for best operation in the individual. The audiologist's console computer is programmed to provide the capability to customize operation of the implanted device while preventing programming of combinations of device operations that could be harmful to the patient or the device. The present invention provides many parameters that are individually settable by the customization program as potential mechanisms for optimizing implant performance for the individual patient. In some embodiments, one or more of the following parameters can be used to encode information on the optical signal: pulse width, peak power, intensity profile over time, stimulation rate, wavelength, polarization, wavelength profile (as a function of spatial location, tissue type, recent-past history of stimulation in a given area, and the like), beam spatial intensity profile, beam angle and the like. In some embodiments, the following parameters can be used to optimize the implant's performance during tuning of the device after implantation: pulse width, amplitude, frequency, wavelength, polarization, wavelength profile, beam profile, beam angle, coding strategy (i.e., N-of-M), signal-processing filter bandwidths, signal-processing filter shapes, audio-signal-processing-filter center frequencies, selection of operational and/or best-functioning channels, and the like. Individual patients may empirically determine a range of comfort levels and settings that provide best performance of the device. The audiologist may adjust the above parameters to provide the patient with best performance. In some embodiments, the patient is provided with a program that they may take home and run on any suitable personal computer, wherein the program is configured to have the computer audibly output a set of calibration tones, tunes, speech or other sounds and to elicit and receive input indications from the patient, and to analyze that input to calculate parameters to be used by the implanted device (and/or the externally-worn device having one or more microphones, power, and sound-processing capability). In some embodiments, "best" performance may be judged by speech recognition, loudness comfort levels, physical comfort, and device battery life.

In some embodiments, the pulse-repetition rate is customized and optimized for the individual during system tuning after implantation. In some embodiments, the peak power of the light signal is customized and optimized for the individual during system tuning after implantation.

In some embodiments, a set of optimal values for pulse-repetition rate, peak power and range of pulse width is determined for each of a number of specific listening environments and sound sources of interest. For example, one set of parameters is optimized for listening to a male voice in a quiet environment. Another set of parameters is optimized for listening to a male voice in a noisy environment (e.g., a crowded room). A third set of parameters is optimized for listening to a female voice in a noisy environment (e.g., a crowded room). Listening environments include, but are not limited to, quiet, many other voices (e.g., a room crowded with people), road noise (e.g., riding in a car or other vehicle), and street noise (e.g., walking along a busy street). Exemplary sound-source environments include, but are not limited to, male or female voice conversations, music, and sounds of nature (e.g., bird calls while bird watching).

In some embodiments, the user of the cochlear implant selects the set of operating parameters (pulse-repetition rate, peak power and pulse width range) to use at any point in time. The selection is made using a device external to the cochlear implant. In some embodiments, the external device is included with an external sound-receiving and signal-processing element that drives the cochlear implant. In other embodiments, a separate device is used that is coupled to the cochlear-implant controller magnetically, via radio frequency signals, via light signals, or via other means. In some embodiments, the controller for the cochlear implant makes an operating-parameter selection based on the controller's analysis of the listening environment. In some embodiments, a collection of sets of operating parameters is provided by the manufacturer of the cochlear implant. In some embodiments, a collection of sets of operating parameters is provided by the audiologist or physician implanting the cochlear implant. In some embodiments, a collection of sets of operating parameters is determined by empirically testing the responses of the wearer of the cochlear implant. In some embodiments, some combination of sources is used to determine the collection of available sets of operating parameters.

Encoding Information in an Optical Cochlear Implant Using Optical-Pulse-Width Modulation Experiments (see Izzo et al.: "Optical Parameter Variability in Laser Nerve Stimulation: a study of pulse duration, repetition rate, and wavelength," 2006; later published in IEEE Trans Biomed Eng. 2007 June; 54(6 Pt 1):1108-14) have shown that neural compound action potentials (CAPs) can be evoked by pulsed optical stimulation and the magnitude of the action potential is a function of the peak power of the incident pulses for pulses shorter than approximately 100 microseconds (μs). As pulses are shortened and peak power is held constant, the CAP reduces. In some embodiments, this effect is utilized to encode loudness information, as the CAP level determines perceived loudness.

In some embodiments, pulse-repetition rate and peak power are held constant, while pulse width is modulated to evoke a sufficient range of CAPs, encoding sound information for the listener. An advantage of this method of encoding is the CAP can be very sensitive to pulse width in this regime, and therefore pulse width is a useful parameter to achieve a large range of stimulation for a small change in pulse width. In one embodiment, the pulse width is customized and optimized for the individual during system tuning after implantation.

In some embodiments, an optimal range of pulse widths is determined (in some such embodiments, the intensity may or may not vary). In some embodiments, the temporal shape of pulses is optimized. In some embodiments, different emitters are used for different portions of pulse.

In some embodiments, the present invention provides an apparatus and method in which pulse-width modulation is applied to the optical-stimulation pulses to the cochlea nerves to obtain an increased dynamic range (a variation in the loudness perceived by the patient). Experiments (Izzo, 2006) have shown that neural compound nerve-action potentials (CNAPs, also called CAPs) can be evoked by pulsed optical stimulation and the magnitude of the action potential is a function of the peak power of the incident pulses for pulses shorter than about 100 microseconds (μs). As pulses are shortened and peak power is held constant, the CAP reduces. This effect can be utilized to encode loudness information, since the CAP level determines perceived loudness. In some embodiments of the present invention, pulse-repetition rate and peak pulse power are held constant, while pulse width is modulated to evoke a sufficient dynamic range of CAPs (i.e., different CAP strengths), thus encoding sound-loudness information for the listener. An advantage of this method of encoding is the CAP can be very sensitive to pulse width in this regime, and therefore optical-pulse width is a useful parameter to vary, and this achieves a large range of stimulation for a small change in pulse width. In some embodiment, the pulse width is adjusted to be optimized for the individual during successive system-tuning sessions after implantation.

Using a Broad Wavelength Profile to Homogenize the Absorption Profile in Optical Stimulation of Nerves In some embodiments, the present invention provides an apparatus and method in which the power-versus-wavelength spectrum of the optical stimulation light is customized to achieve a desired spatial-absorption pattern. In electrical stimulation, one challenging problem is the undesired spreading of the electrical signal through the conductive fluid and tissue in the cochlea. The optical stimulation of the present invention does not suffer this problem and therefore has an advantage in its ability to stimulate in a more specific manner (i.e., to trigger CNAPs for narrower audio frequency ranges (more specific frequencies), for an increased number of different audio frequency ranges (the narrower and more numerous audio frequency ranges result from the optical stimulation that does not spread to adjacent tissues as much as electrical stimulation does), and for a greater range of different loudness levels (increased dynamic range), which leads to higher spectral fidelity for the implantee. A challenge that the present invention solves is to deliver a stimulation signal that triggers CNAPs that are perceived as quite different loudnesses, i.e., as sounds with a substantial dynamic range. The physical extent (the volume) of the stimulated region is limited by the absorption profile of the spiral ganglion cells (or other suitable tissue cells) that are being stimulated, and by the fluence of the optical spot at the tissue interface. The absorption coefficient is wavelength dependent and therefore the spatial absorption profile is wavelength dependent. When a spot of light illuminates the modiolus and reaches the spiral-ganglion-cell interface, the cells absorb light according to their optical absorption coefficient. Because the light experiences exponential decay as it travels through the volume of cells, the absorption profile in the illuminated volume is exponential in nature, and more light is absorbed near the surface and less is absorbed deeper in the tissue (see FIG. 4, FIG. 4A, FIG. 4B, FIG. 4C, FIG. 4D, and FIG. 4E). FIG. 4 is a color-coded plot of a temperature profile of tissue due to absorption of single-wavelength source of infrared light. When a single wavelength is used to stimulate (as in FIG. 4, FIG. 4A, FIG. 4B, and FIG. 4C), there exists a limited range of fluence that can be utilized for stimulation. There is a minimum fluence to reach the hearing threshold and, as the fluence is increased, deeper cells are recruited for stimulation but a limitation is reached when the interface tissue, where the bulk of the absorption is taking place, becomes too hot. The exponential profile of absorption is unwanted if a large dynamic range is desired, which is the case in some embodiments of the present invention. In some embodiments, a broad linewidth source (e.g., see FIG. 3A, FIG. 3C, and FIG. 3E) is used with an optimized wavelength profile that homogenizes the absorption profile in the tissue. In one embodiment, the profile may dynamically change as the power is increased, optimizing the absorption profile. One advantage of this solution is that the dynamic range is extended due to the even spread of absorption in the illuminated volume. As shown in FIG. 3A, FIG. 3C, FIG. 3E, FIG. 4D, and FIG. 4E, in some embodiments, a broad wavelength source is used with a power/wavelength profile that is designed and crafted to homogenize the absorption in the tissue. As shown in FIG. 4F, FIG. 4G and FIG. 4H, in some embodiments, the wavelength source has a power/wavelength profile that is designed and crafted to change over time such that the absorption in the tissue is customized to obtain the desired triggering of NAPs.

In some embodiments, the first predetermined amount of energy is the same as the second predetermined amount of energy, but the power of one is increased and the duration is decreased by a compensating value such that even though the amounts of energy are the same, the peak powers are different. In some embodiments, this is the result of using different pulse shapes, wherein pulse shape is defined as the amount of power as a function of time.

In some embodiments, the first pulsed optical-stimulation signal has a first pulse at the first wavelength that starts at a first starting point in time and a second pulse at the second wavelength that starts at a second starting point in time, and wherein the first starting point of the signal at the first wavelength is different than the second starting point of the signal at the second wavelength and both the first and second pulses contribute to triggering the same NAP or CNAP (i.e., a single NAP or a single CNAP). In other embodiments, the first pulsed optical-stimulation signal has a first pulse at the first wavelength that ends at a first ending point in time and a second pulse at the second wavelength that ends at a second ending point in time, and wherein the first ending point of the signal at the first wavelength is different than the second ending point of the signal at the second wavelength, and both the first and second pulses contribute to triggering the same NAP or CNAP. In either case, the pulses are not simultaneous, but they are partially overlapped, or at least nearby in time so as to be synergistic in triggering one NAP or CNAP.

Further Discussion of Optimization of Individual Performance of an Optical Cochlear Implant In some embodiments, the present invention includes a method, where the method includes generating a plurality of pulsed light signals having one or more successive pulses that, when applied to a neuron of a person, will each stimulate a nerve action potential (NAP) in the neuron, delivering the plurality of light signals to a plurality of locations in the cochlea of the person, and selectively controlling the plurality of light signals to optically stimulate one or more neurons in the cochlea in order to trigger NAPs in the one or more neurons of the cochlea. The selectively controlling includes empirically testing the delivering of the plurality of light signals and determining one or more calibration values, for each of a plurality of optical-stimulation parameters, that is/are most effective for optically stimulating the one or more neurons of the cochlea, and using results of the testing such that the delivering includes delivering the plurality of light signals to the one or more neurons of the cochlea using the one or more calibration values of the plurality of optical-stimulation parameters that was/were determined to be most effective for optically stimulating the one or more neurons of the cochlea.

In some embodiments, the determining of the one or more calibration values most effective for optically stimulating the one or more neurons of the cochlea includes eliciting and receiving input from the person, and based on the input, determining speech-recognition score for each of a plurality of values for each of the plurality of optical-stimulation parameters used during the testing. In other embodiments, the determining of the one or more values most effective for optically stimulating the one or more neurons of the cochlea includes eliciting and receiving feedback from the person as to a loudness-comfort level of the person at each of a plurality of values for each of the plurality of optical-stimulation parameters used during the testing. In other embodiments, the determining of the one or more values most effective for optically stimulating the one or more neurons of the cochlea includes eliciting and receiving feedback from the person as to a physical-comfort level of the person at each of a plurality of values for each of the plurality of optical-stimulation parameters used during the testing.

In some embodiments of the method, the generating of the plurality of light signals includes organizing the plurality of light signals in a plurality of optical-stimulation channels, and wherein the selectively controlling includes determining which of a plurality of optical-stimulation channels are more functional in triggering auditory sensations at each of a plurality of perceived frequencies, and thereafter using certain channels determined to be more functional and not using certain other channels determined to be less functional.

In some embodiments, the method further includes providing a battery operably coupled to power the generating of the plurality of light signals, and the determining of the one or more values most effective for optically stimulating the one or more neurons of the cochlea includes determining a battery-life of the battery at each of a plurality of values for each of the plurality of optical-stimulation parameters used during the testing.

In some embodiments of the method, the selectively controlling includes determining one or more light-signal-pulse-width values that is/are most effective for optically stimulating the one or more neurons of the cochlea. In some embodiments, the selectively controlling includes determining one or more light-signal-peak-intensity values that is/are most effective for optically stimulating the one or more neurons of the cochlea. In some embodiments, the selectively controlling includes determining one or more light-signal-pulse-repetition-rate values that is/are most effective for optically stimulating the one or more neurons of the cochlea. In some embodiments, the selectively controlling includes determining one or more light-signal-wavelength values that is/are most effective for optically stimulating the one or more neurons of the cochlea. In some embodiments, the selectively controlling includes determining one or more light-signal-polarization values that is/are most effective for optically stimulating the one or more neurons of the cochlea. In some embodiments, the selectively controlling includes determining one or more light-signal-wavelength-profile values that is/are most effective for optically stimulating the one or more neurons of the cochlea.

In some embodiments of the method, the selectively controlling includes determining one or more light-signal-spatial-beam-profile values that is/are most effective for optically stimulating the one or more neurons of the cochlea. In some embodiments, the selectively controlling includes determining one or more light-signal-beam-profile values that is/are most effective for optically stimulating the one or more neurons of the cochlea. In some embodiments, the selectively controlling includes determining a light-signal-coding strategy that is most effective for optically stimulating the one or more neurons of the cochlea. In some embodiments, the selectively controlling includes determining one or more signal-processing-filter-bandwidth values that is/are most effective for optically stimulating the one or more neurons of the cochlea. In some embodiments, the selectively controlling includes determining one or more signal-processing-filter-shape values (i.e., the intensity-versus-frequency curve) that is/are most effective for optically stimulating the one or more neurons of the cochlea. In some embodiments, the selectively controlling includes determining one or more signal-processing-filter-center-frequency values that is/are most effective for optically stimulating the one or more neurons of the cochlea.

In some embodiments of the method, the generating of the plurality of light signals includes organizing the plurality of light signals in a plurality of optical-stimulation channels, and wherein the selectively controlling includes determining a number of optical-stimulation channels that are functional.

In some embodiments, the present invention includes an apparatus, where the apparatus includes means for generating a plurality of pulsed light signals having one or more successive pulses that, when applied to a neuron of a person, will each stimulate a nerve action potential (NAP) in the neuron, means for delivering the plurality of light signals to a plurality of locations in the cochlea of the person, and means for selectively controlling the plurality of light signals to optically stimulate one or more neurons in the cochlea in order to trigger NAPs in the one or more neurons of the cochlea, such that the means for selectively controlling includes means for empirically testing the means for delivering of the plurality of light signals and means for determining one or more values, for each of a plurality of optical-stimulation parameters, that is/are most effective for optically stimulating the one or more neurons of the cochlea, and means for using results of the tests such that the means for delivering includes means for delivering the plurality of light signals to one or more neurons of the cochlea using the one or more values of the plurality of optical-stimulation parameters that was/were determined to be most effective for optically stimulating the one or more neurons of the cochlea.

In some embodiments of the apparatus, the means for determining of the one or more values most effective for optically stimulating the one or more neurons of the cochlea includes means for eliciting and receiving input from the person, and based on the input, for determining a speech-recognition score for each of a plurality of values for each of the plurality of optical-stimulation parameters used during the testing. In some embodiments, the means for determining of the one or more values most effective for optically stimulating the one or more neurons of the cochlea includes means for eliciting and receiving feedback from the person as to a loudness-comfort level of the person at each of a plurality of values for each of the plurality of optical-stimulation parameters used during the testing. In some embodiments, the means for determining of the one or more values most effective for optically stimulating the one or more neurons of the cochlea includes means for eliciting and receiving feedback from the person as to a physical-comfort level of the person at each of a plurality of values for each of the plurality of optical-stimulation parameters used during the testing.

In some embodiments, the present invention further includes means for supplying electrical energy operably coupled to power the means for generating of the plurality of light signals, and the means for determining of the one or more values most effective for optically stimulating the one or more neurons of the cochlea includes means for determining an electrical-energy usage rate at each of a plurality of values for each of the plurality of optical-stimulation parameters used during the testing.

In some embodiments, the means for selectively controlling includes means for determining one or more light-signal-pulse-width values that is/are most effective for optically stimulating the one or more neurons of the cochlea. In some embodiments, the means for selectively controlling includes means for determining one or more light-signal-peak-intensity values that is/are most effective for optically stimulating the one or more neurons of the cochlea. In some embodiments, the means for selectively controlling includes means for determining one or more light-signal-pulse-repetition-rate values that is/are most effective for optically stimulating the one or more neurons of the cochlea. In some embodiments, the means for selectively controlling includes means for determining one or more light-signal-wavelength values that is/are most effective for optically stimulating the one or more neurons of the cochlea. In some embodiments, the means for selectively controlling includes means for determining one or more light-signal-polarization values that is/are most effective for optically stimulating the one or more neurons of the cochlea. In some embodiments, the means for selectively controlling includes means for determining one or more light-signal-wavelength-profile values that is/are most effective for optically stimulating the one or more neurons of the cochlea. In some embodiments, the means for selectively controlling includes means for determining one or more light-signal-spatial-beam-profile values that is/are most effective for optically stimulating the one or more neurons of the cochlea. In some embodiments, the means for selectively controlling includes means for determining one or more light-signal-beam-profile values that is/are most effective for optically stimulating the one or more neurons of the cochlea. In some embodiments, the means for selectively controlling includes means for determining a light-signal-coding strategy that is most effective for optically stimulating the one or more neurons of the cochlea. In some embodiments, the means for selectively controlling includes means for determining one or more signal-processing-filter-bandwidth values that is/are most effective for optically stimulating the one or more neurons of the cochlea. In some embodiments, the means for selectively controlling includes means for determining one or more signal-processing-filter-shape values (i.e., the intensity-versus-frequency curve) that is/are most effective for optically stimulating the one or more neurons of the cochlea. In some embodiments, the means for selectively controlling includes means for determining one or more signal-processing-filter-center-frequency values that is/are most effective for optically stimulating the one or more neurons of the cochlea.

In some embodiments, the means for generating of the plurality of light signals includes means for organizing the plurality of light signals in a plurality of optical-stimulation channels, and wherein the selectively controlling includes means for determining a number of optical-stimulation channels that are functional.

The present invention, in some embodiments, includes an apparatus, where the apparatus includes an optical generator that is configured to generate a plurality of pulsed light signals having one or more successive pulses that, when applied to a neuron of a person, will each stimulate a nerve action potential (NAP) in the neuron, an optical guide configured to deliver the plurality of light signals to a plurality of locations in the cochlea of the person, and a controller configured to selectively control the plurality of light signals to optically stimulate one or more neurons in the cochlea in order to trigger NAPs in the one or more neurons of the cochlea. The controller is configured to empirically test the delivery of the plurality of light signals and determine one or more values, for each of a plurality of optical-stimulation parameters, that is/are most effective for optically stimulating the one or more neurons of the cochlea, and use results of the test such that the delivery includes the delivery of the plurality of light signals with the one or more values of the plurality of optical-stimulation parameters that was/were determined to be most effective for optically stimulating the one or more neurons of the cochlea.

In some embodiments, the controller is further configured to elicit and receive input from the person, and based on the input, to determine a speech-recognition score for each of a plurality of values for each of the plurality of optical-stimulation parameters used during the testing and determine the one or more values most effective for optically stimulating the one or more neurons of the cochlea. In some embodiments, the controller is further configured to elicit and receive feedback from the person as to a loudness-comfort level of the person at each of a plurality of values for each of the plurality of optical-stimulation parameters used during the testing and determine the one or more values most effective for optically stimulating the one or more neurons of the cochlea. In some embodiments, the controller is further configured to elicit and receive feedback from the person as to a physical-comfort level of the person at each of a plurality of values for each of the plurality of optical-stimulation parameters used during the testing and determine the one or more values most effective for optically stimulating the one or more neurons of the cochlea includes eliciting and receiving.

In some embodiments, the apparatus further includes a battery operably coupled to power the optical generator, and the controller is further configured to determine a battery-life of the battery at each of a plurality of values for each of the plurality of optical-stimulation parameters used during the testing.

In some embodiments, the controller is further configured to determine one or more light-signal-pulse-width values that is/are most effective for optically stimulating the one or more neurons of the cochlea. In some embodiments, the controller is further configured to determine one or more light-signal-peak-intensity values that is/are most effective for optically stimulating the one or more neurons of the cochlea. In some embodiments, the controller is further configured to determine one or more light-signal-pulse-repetition-rate values that is/are most effective for optically stimulating the one or more neurons of the cochlea. In some embodiments, the controller is further configured to determine one or more light-signal-wavelength values that is/are most effective for optically stimulating the one or more neurons of the cochlea. In some embodiments, the controller is further configured to determine one or more light-signal-polarization values that is/are most effective for optically stimulating the one or more neurons of the cochlea. In some embodiments, the controller is further configured to determine one or more light-signal-wavelength-profile values that is/are most effective for optically stimulating the one or more neurons of the cochlea. In some embodiments, the controller is further configured to determine one or more light-signal-spatial-beam-profile values that is/are most effective for optically stimulating the one or more neurons of the cochlea. In some embodiments, the controller is further configured to determine one or more light-signal-beam-profile values that is/are most effective for optically stimulating the one or more neurons of the cochlea. In some embodiments, the controller is further configured to determine a light-signal-coding strategy that is most effective for optically stimulating the one or more neurons of the cochlea. In some embodiments, the controller is further configured to determine one or more signal-processing-filter-bandwidth values that is/are most effective for optically stimulating the one or more neurons of the cochlea. In some embodiments, the controller is further configured to determine one or more signal-processing-filter-shape values (i.e., the intensity-versus-frequency curve) that is/are most effective for optically stimulating the one or more neurons of the cochlea. In some embodiments, the controller is further configured to determine one or more signal-processing-filter-center-frequency values that is/are most effective for optically stimulating the one or more neurons of the cochlea.

In some embodiments of the present invention, the optical generator is further configured to organize the plurality of light signals in a plurality of optical-stimulation channels, and the controller is further configured to determine a number of optical-stimulation channels that are functional.

In some embodiments, the present invention includes a non-transitory computer readable medium having instructions stored thereon for causing a suitably programmed information processor to perform a method, where the method includes generating a plurality of pulsed light signals having one or more successive pulses that, when applied to a neuron of a person, will each stimulate a nerve action potential (NAP) in the neuron, delivering the plurality of light signals to a plurality of locations in the cochlea of the person, and selectively controlling the plurality of light signals to optically stimulate one or more neurons in the cochlea in order to trigger NAPs in the one or more neurons of the cochlea. The selectively controlling includes empirically testing the delivering of the plurality of light signals and determining one or more calibration values, for each of a plurality of optical-stimulation parameters, that is/are most effective for optically stimulating the one or more neurons of the cochlea, and using results of the testing such that the delivering includes delivering the plurality of light signals to the one or more neurons of the cochlea using the one or more calibration values of the plurality of optical-stimulation parameters that was/were determined to be most effective for optically stimulating the one or more neurons of the cochlea.

In some embodiments, the non-transitory computer readable medium further includes instructions such that the determining of the one or more values most effective for optically stimulating the one or more neurons of the cochlea includes eliciting and receiving input from the person, and based on the input, determining a speech-recognition score for each of a plurality of values for each of the plurality of optical-stimulation parameters used during the testing. In some embodiments, the non-transitory computer readable medium further includes instructions such that the determining of the one or more values most effective for optically stimulating the one or more neurons of the cochlea includes eliciting and receiving feedback from the person as to a loudness-comfort level of the person at each of a plurality of values for each of the plurality of optical-stimulation parameters used during the testing. In some embodiments, the non-transitory computer readable medium further includes instructions such that the determining of the one or more values most effective for optically stimulating the one or more neurons of the cochlea includes eliciting and receiving feedback from the person as to a physical-comfort level of the person at each of a plurality of values for each of the plurality of optical-stimulation parameters used during the testing.

In some embodiments, the non-transitory computer readable medium further includes instructions such that the method further includes providing a battery operably coupled to power the generating of the plurality of light signals, and the determining of the one or more values most effective for optically stimulating the one or more neurons of the cochlea includes determining a battery-life of the battery at each of a plurality of values for each of the plurality of optical-stimulation parameters used during the testing.

In some embodiments, the non-transitory computer readable medium further includes instructions such that the selectively controlling includes determining one or more light-signal-pulse-width values that is/are most effective for optically stimulating the one or more neurons of the cochlea. In some embodiments, the non-transitory computer readable medium further includes instructions such that the selectively controlling includes determining one or more light-signal-peak-intensity values that is/are most effective for optically stimulating the one or more neurons of the cochlea. In some embodiments, the non-transitory computer readable medium further includes instructions such that the selectively controlling includes determining one or more light-signal-pulse-repetition-rate values that is/are most effective for optically stimulating the one or more neurons of the cochlea. In some embodiments, the non-transitory computer readable medium further includes instructions such that the selectively controlling includes determining one or more light-signal-wavelength values that is/are most effective for optically stimulating the one or more neurons of the cochlea.

In some embodiments, the non-transitory computer readable medium further includes instructions such that the selectively controlling includes determining one or more light-signal-polarization values that is/are most effective for optically stimulating the one or more neurons of the cochlea. In some embodiments, the non-transitory computer readable medium further includes instructions such that the selectively controlling includes determining one or more light-signal-wavelength-profile values that is/are most effective for optically stimulating the one or more neurons of the cochlea. In some embodiments, the non-transitory computer readable medium of claim 61, wherein the medium further includes instructions such that the selectively controlling includes determining one or more light-signal-spatial-beam-profile values (e.g., which beam spatial shapes) that is/are most effective for optically stimulating the one or more neurons of the cochlea. In some embodiments, the non-transitory computer readable medium further includes instructions such that the selectively controlling includes determining one or more light-signal-beam-profile values that is/are most effective for optically stimulating the one or more neurons of the cochlea. In some embodiments, the non-transitory computer readable medium further includes instructions such that the selectively controlling includes determining a light-signal-coding strategy that is most effective for optically stimulating the one or more neurons of the cochlea. In some embodiments, the non-transitory computer readable medium further includes instructions such that the selectively controlling includes determining one or more signal-processing-filter-bandwidth values that is/are most effective for optically stimulating the one or more neurons of the cochlea. In some embodiments, the non-transitory computer readable medium further includes instructions such that the selectively controlling includes determining one or more signal-processing-filter-shape values (i.e., the intensity-versus-frequency curve) that is/are most effective for optically stimulating the one or more neurons of the cochlea. In some embodiments, the non-transitory computer readable medium further includes instructions such that the selectively controlling includes determining one or more signal-processing-filter-center-frequency values that is/are most effective for optically stimulating the one or more neurons of the cochlea.

In some embodiments, the non-transitory computer readable medium further includes instructions such that the generating of the plurality of light signals includes organizing the plurality of light signals in a plurality of optical-stimulation channels, and the selectively controlling includes determining a number of optical-stimulation channels that are functional.

In some embodiments, the present invention includes a method for optically stimulating neurons of a cochlea of a person to provide auditory sensations for the person. The method includes entering a calibration mode and performing a calibration that includes: generating a plurality of pulsed light signals having one or more successive pulses that, when applied to a neuron of a person, will each stimulate a nerve action potential (NAP) in the neuron, delivering the plurality of light signals to a plurality of locations in the cochlea of the person, selectively controlling the plurality of light signals to optically stimulate one or more neurons in the cochlea in order to trigger NAPs in the one or more neurons of the cochlea, and empirically testing the delivering of the plurality of light signals and determining one or more calibration values, for each of a plurality of optical-stimulation parameters, that is/are most effective for optically stimulating the one or more neurons of the cochlea. the method further includes entering a first listening mode that includes: receiving an audio signal, generating, based on the received audio signal, a plurality of pulsed light signals having one or more successive pulses and, using results of the testing, having the one or more calibration values of the plurality of optical-stimulation parameters that was/were determined to be most effective for optically stimulating the one or more neurons of the cochlea, and delivering the plurality of light signals to the one or more neurons of the cochlea using the one or more values of the plurality of optical-stimulation parameters that was/were determined to be most effective for optically stimulating the one or more neurons of the cochlea.

In some embodiments, the present invention includes an apparatus for optically stimulating neurons of a cochlea of a person to provide auditory sensations for the person. The apparatus includes means for entering a calibration mode and performing a calibration that includes: means for generating a plurality of pulsed light signals having one or more successive pulses that, when applied to a neuron of a person, will each stimulate a nerve action potential (NAP) in the neuron, means for delivering the plurality of light signals to a plurality of locations in the cochlea of the person, means for selectively controlling the plurality of light signals to optically stimulate one or more neurons in the cochlea in order to trigger NAPs in the one or more neurons of the cochlea, and means for empirically testing the delivering of the plurality of light signals and determining one or more calibration values, for each of a plurality of optical-stimulation parameters, that is/are most effective for optically stimulating the one or more neurons of the cochlea. The apparatus further includes means for entering a first listening mode that includes: a means for receiving an audio signal, means for generating, based on the received audio signal, a plurality of pulsed light signals having one or more successive pulses and, means for using results of the testing, having the one or more calibration values of the plurality of optical-stimulation parameters that was/were determined to be most effective for optically stimulating the one or more neurons of the cochlea, and means for delivering the plurality of light signals to the one or more neurons of the cochlea using the one or more values of the plurality of optical-stimulation parameters that was/were determined to be most effective for optically stimulating the one or more neurons of the cochlea.

In some embodiments, the present invention includes an apparatus for optically stimulating neurons of a cochlea of a person to provide auditory sensations for the person. The apparatus includes a system configured to enter a calibration mode that includes: an optical generator that generates a plurality of pulsed light signals having one or more successive pulses that, when applied to a neuron of a person, will each stimulate a nerve action potential (NAP) in the neuron, an optical guide configured to deliver the plurality of light signals to a plurality of locations in the cochlea of the person, and a controller configured to: selectively control the plurality of light signals to optically stimulate one or more neurons in the cochlea in order to trigger NAPs in the one or more neurons of the cochlea, and empirically test the delivery of the plurality of light signals and determine one or more values, for each of a plurality of optical-stimulation parameters, that is/are most effective for optically stimulating the one or more neurons of the cochlea. the apparatus further includes a system configured to enter a first listening mode that includes: an audio sensor configured to receive an audio signal, the optical generator further configured to generate, based on the received audio signal, a plurality of pulsed light signals having one or more successive pulses and to use the results of the tests, wherein a plurality of pulsed light signals have the one or more values of the plurality of optical-stimulation parameters that was/were determined to be most effective for optically stimulating the one or more neurons of the cochlea, and the optical guide further configured to deliver the plurality of light signals using the one or more values of the plurality of optical-stimulation parameters that was/were determined to be most effective for optically stimulating the one or more neurons of the cochlea.

In some embodiments, the present invention includes a non-transitory computer readable medium having instructions stored thereon for causing a suitably programmed information processor to perform a method for optically stimulating neurons of a cochlea of a person to provide auditory sensations for the person. The method includes entering a calibration mode and performing a calibration that includes: generating a plurality of pulsed light signals having one or more successive pulses that, when applied to a neuron of a person, will each stimulate a nerve action potential (NAP) in the neuron, delivering the plurality of light signals to a plurality of locations in the cochlea of the person, selectively controlling the plurality of light signals to optically stimulate one or more neurons in the cochlea in order to trigger NAPs in the one or more neurons of the cochlea, and empirically testing the delivering of the plurality of light signals and determining one or more calibration values, for each of a plurality of optical-stimulation parameters, that is/are most effective for optically stimulating the one or more neurons of the cochlea. The method further includes entering a first listening mode that includes: receiving an audio signal, generating, based on the received audio signal, a plurality of pulsed light signals having one or more successive pulses and, using results of the testing, having the one or more calibration values of the plurality of optical-stimulation parameters that was/were determined to be most effective for optically stimulating the one or more neurons of the cochlea, and delivering the plurality of light signals to the one or more neurons of the cochlea using the one or more values of the plurality of optical-stimulation parameters that was/were determined to be most effective for optically stimulating the one or more neurons of the cochlea.

It is specifically contemplated that the present invention includes embodiments having combinations and subcombinations of the various embodiments and features that are individually described herein and in patents and applications incorporated herein by reference (i.e., rather than listing every combinatorial of the elements, this specification includes descriptions of representative embodiments and contemplates embodiments that include some of the features from one embodiment combined with some of the features of another embodiment). Further, some embodiments include fewer than all the components described as part of any one of the embodiments described herein.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An implanted apparatus for optically stimulating neurons of a cochlea of a person to provide auditory sensations for the person, the implanted apparatus comprising:
   means for calibrating in a calibration mode, wherein the means for calibrating includes:
   means for generating a plurality of pulsed light signals each having a plurality of successive pulses that, when applied to a neuron of a person, will each stimulate a nerve action potential (NAP) in the neuron,
   means for delivering each one of the plurality of light signals to a different one of a plurality of locations in the cochlea of the person, wherein the means for generating and the means for delivering are configured to be implanted in the cochlea of the person, and
   means for selectively controlling the plurality of light signals to optically stimulate one or more neurons at the respective one of the plurality of locations in the cochlea in order to trigger NAPs in the one or more neurons of the cochlea, and
   means for empirically testing the delivering of the plurality of light signals, wherein the means for empirically testing is configured to vary and determine one or more values, for each of a plurality of variable optical-stimulation parameters, that is most effective for optically stimulating the one or more neurons of the cochlea of the person having the implanted apparatus based on perceived-sensation feedback from the person, wherein the perceived-sensation feedback includes a speech recognition score or a loudness comfort-level, wherein the plurality of varied parameters includes a spectral wavelength and a polarization of the plurality of light signals; and
   means for providing an audio perception in a first listening mode, wherein the means for providing the audio perception includes:
   means for receiving an audio signal, the means for generating, further configured to generate, based on the received audio signal, a plurality of pulsed light signals having one or more successive pulses and, based on results from the means for testing, using the one or more values for each one of the plurality of optical-stimulation parameters that was determined to be most effective for optically stimulating the one or more neurons of the cochlea, and
   the means for delivering, further configured to deliver the plurality of light signals to the one or more neurons of the cochlea using the one or more values for each one of the plurality of optical-stimulation parameters that was determined to be most effective for optically stimulating the one or more neurons of the cochlea.

2. The apparatus of claim 1, wherein the means for empirically testing includes means for eliciting and receiving input from the person, and based on the input, for determining a speech-recognition score for each of a plurality of values for each of the plurality of optical-stimulation parameters used during the testing.

3. The apparatus of claim 1, wherein the means for empirically testing includes means for eliciting and receiving feedback from the person as to a physical-comfort level of the person at each of a plurality of values for each of the plurality of optical-stimulation parameters used during the testing.

4. The apparatus of claim 1, wherein the means for selectively controlling includes means for determining one or more light-signal-pulse-width values that is most effective for optically stimulating the one or more neurons of the cochlea.

5. The apparatus of claim 1, wherein the means for selectively controlling includes means for determining one or more light-signal-pulse-repetition-rate values that is most effective for optically stimulating the one or more neurons of the cochlea.

6. The apparatus of claim 1, wherein the means for selectively controlling includes means for determining one or more audio-signal-processing-filter-bandwidth values, one or more audio-signal-processing-filter-shape values, and one or more audio-signal-processing-filter-center-frequency values that are most effective for optically stimulating the one or more neurons of the cochlea.

7. The apparatus of claim 1, wherein the means for generating the plurality of light signals includes means for grouping one or more of the plurality of light signals into each one of a plurality of optical-stimulation channels, and wherein the selectively controlling includes means for determining which optical-stimulation channels are most effective in triggering auditory sensations at each of a plurality of perceived frequencies, and thereafter using certain channels determined to be most effective and not using certain other channels.

8. The apparatus of claim 1, wherein the means for generating include a vertical-cavity surface-emitting laser.

9. The apparatus of claim 1, wherein the means for selectively controlling includes means for determining one or more light-signal-pulse-beam-profile values that is most effective for optically stimulating the one or more neurons of the cochlea.

10. The apparatus of claim 1, wherein the means for selectively controlling includes means for determining one or more light-signal-pulse-beam-angle values that is most effective for optically stimulating the one or more neurons of the cochlea.

11. An implanted apparatus for optically stimulating neurons of a cochlea of a person to provide auditory sensations for the person, the implanted apparatus comprising:
a calibration system that includes:
a plurality of optical generators that generate a plurality of pulsed light signals each having a plurality of successive pulses that, when applied to a neuron of a person, will each stimulate a nerve action potential (NAP) in the neuron,
an optical guide configured to deliver each one of the plurality of light signals to a different one of a plurality of locations in the cochlea of the person, wherein the plurality of optical generators and the optical guide are configured to be implanted in the cochlea of the person, and a controller configured to:
selectively control the plurality of light signals to optically stimulate one or more neurons at the respective one of the plurality of locations in the cochlea in order to trigger NAPs in the one or more neurons of the cochlea, and
empirically test the delivery of the plurality of light signals by the optical guide and vary and determine one or more values, for each of a plurality of variable optical-stimulation parameters, that is most effective for optically stimulating the one or more neurons of the cochlea of the person having the implanted apparatus based on perceived-sensation feedback from the person, wherein the perceived-sensation feedback includes a speech recognition score or a loudness comfort-level, wherein the plurality of varied parameters includes a spectral wavelength and a polarization of the plurality of light signals; and
a first-listening-mode system that includes:
an audio sensor configured to receive an audio signal, the optical generator further configured to generate, based on the received audio signal, a plurality of pulsed light signals having one or more successive pulses and to use the results of the empirical test, wherein a plurality of pulsed light signals have the one or more values for each one of the plurality of optical-stimulation parameters that was determined to be most effective for optically stimulating the one or more neurons of the cochlea, and the optical guide further configured to deliver the plurality of light signals using the one or more values for each one of the plurality of optical-stimulation parameters that was determined to be most effective for optically stimulating the one or more neurons of the cochlea.

12. The apparatus of claim 11, wherein the calibration system is further configured to elicit and receive input from the person, and based on the input, to determine a speech-recognition score for each of a plurality of values for each of the plurality of optical-stimulation parameters used during the testing and determine the one or more values most effective for optically stimulating the one or more neurons of the cochlea.

13. The apparatus of claim 11, wherein the calibration system is further configured to elicit and receive feedback from the person as to a loudness-comfort level of the person at each of a plurality of values for each of the plurality of optical-stimulation parameters used during the testing and determine the one or more values most effective for optically stimulating the one or more neurons of the cochlea.

14. The apparatus of claim 11, wherein the calibration system is further configured to determine one or more light-signal-pulse-width values that is most effective for optically stimulating the one or more neurons of the cochlea.

15. The apparatus of claim 11, wherein the calibration system is further configured to determine one or more light-signal-pulse-repetition-rate values that is most effective for optically stimulating the one or more neurons of the cochlea.

16. The apparatus of claim 11, wherein the calibration system is further configured to determine one or more signal-processing-filter-bandwidth values and one or more signal-processing-filter-shape values that are most effective for optically stimulating the one or more neurons of the cochlea.

17. The apparatus of claim 11, wherein the calibration system is further configured to determine one or more light-signal-pulse-amplitude values that is most effective for optically stimulating the one or more neurons of the cochlea.

18. The apparatus of claim 11, wherein the plurality of optical generators include a vertical-cavity surface-emitting laser.

19. The apparatus of claim 11, wherein the calibration system is further configured to determine one or more light-signal-pulse-beam-profile values that is most effective for optically stimulating the one or more neurons of the cochlea.

20. The apparatus of claim 11, wherein the calibration system is further configured to determine one or more light-signal-pulse-beam-angle values that is most effective for optically stimulating the one or more neurons of the cochlea.

* * * * *